(12) United States Patent
Martin

(10) Patent No.: US 9,726,673 B2
(45) Date of Patent: Aug. 8, 2017

(54) METHODS AND COMPOSITIONS RELATED TO B CELL ASSAYS

(75) Inventor: Flavius Martin, Hayward, CA (US)

(73) Assignee: Genentech, Inc., South San Fracisco, CA (US)

( * ) Notice: Subject to any disclaimer, the term of this patent is extended or adjusted under 35 U.S.C. 154(b) by 352 days.

(21) Appl. No.: 11/602,728

(22) Filed: Nov. 21, 2006

(65) Prior Publication Data

US 2007/0212733 A1 Sep. 13, 2007

Related U.S. Application Data

(60) Provisional application No. 60/739,266, filed on Nov. 23, 2005, provisional application No. 60/857,925, filed on Nov. 10, 2006.

(51) Int. Cl.
*A61K 39/395* (2006.01)
*G01N 33/68* (2006.01)
*G01N 33/50* (2006.01)
*G01N 33/53* (2006.01)

(52) U.S. Cl.
CPC ..... *G01N 33/6863* (2013.01); *G01N 33/5052* (2013.01); *G01N 2333/525* (2013.01); *G01N 2333/70578* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 4,179,337 A | 12/1979 | Davis et al. |
| 4,301,144 A | 11/1981 | Iwashita et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,816,567 A | 3/1989 | Cabilly et al. |
| 4,861,579 A | 8/1989 | Meyer et al. |
| 5,182,196 A | 1/1993 | Allet et al. |
| 5,262,309 A | 11/1993 | Nakamura et al. |
| 5,422,104 A | 6/1995 | Fiers et al. |
| 5,428,130 A | 6/1995 | Capon et al. |
| 5,486,463 A | 1/1996 | Lesslauer et al. |
| 5,500,362 A | 3/1996 | Robinson et al. |
| 5,519,119 A | 5/1996 | Yamada et al. |
| 5,540,926 A | 7/1996 | Aruffo et al. |
| 5,587,457 A | 12/1996 | Rathjen et al. |
| 5,595,721 A | 1/1997 | Kaminski et al. |
| 5,610,279 A | 3/1997 | Brockhaus et al. |
| 5,641,663 A | 6/1997 | Garvin et al. |
| 5,652,353 A | 7/1997 | Fiers et al. |
| 5,677,180 A | 10/1997 | Robinson et al. |
| 5,721,108 A | 2/1998 | Robinson et al. |
| 5,736,137 A | 4/1998 | Anderson et al. |
| 5,776,456 A | 7/1998 | Anderson et al. |
| 5,808,029 A | 9/1998 | Brockhaus et al. |
| 5,821,337 A | 10/1998 | Carter et al. |
| 5,843,398 A | 12/1998 | Kaminski et al. |
| 5,843,439 A | 12/1998 | Anderson et al. |
| 5,849,898 A | 12/1998 | Seed et al. |
| 5,969,102 A | 10/1999 | Bram et al. |
| 6,015,542 A | 1/2000 | Kaminski et al. |
| 6,090,365 A | 7/2000 | Kaminski et al. |
| 6,120,767 A | 9/2000 | Robinson et al. |
| 6,171,586 B1 | 1/2001 | Lam et al. |
| 6,171,787 B1 | 1/2001 | Wiley |
| 6,194,551 B1 | 2/2001 | Idusogie et al. |
| 6,224,866 B1 | 5/2001 | Barbera-Guillem |
| 6,242,195 B1 | 6/2001 | Idusogie et al. |
| 6,287,537 B1 | 9/2001 | Kaminski et al. |
| 6,297,022 B1 | 10/2001 | McDonnell et al. |
| 6,297,367 B1 | 10/2001 | Tribouley |
| 6,306,393 B1 | 10/2001 | Goldenberg |
| 6,316,222 B1 | 11/2001 | Bram et al. |
| 6,355,782 B1 | 3/2002 | Zohaha et al. |
| 6,368,596 B1 | 4/2002 | Ghetie et al. |
| 6,399,061 B1 | 6/2002 | Anderson et al. |
| 6,403,770 B1 | 6/2002 | Yu et al. |
| 6,410,391 B1 | 6/2002 | Zelsacher |
| 6,440,694 B1 | 8/2002 | Bienkowski et al. |
| 6,455,043 B1 | 9/2002 | Grillo-Lopez |
| 6,475,986 B1 | 11/2002 | Aggarwal |
| 6,475,987 B1 | 11/2002 | Shu |
| 6,500,428 B1 | 12/2002 | Bram et al. |
| 6,506,882 B2 | 1/2003 | Yu et al. |

(Continued)

FOREIGN PATENT DOCUMENTS

EP 0 307 247 A2 3/1989
EP 0 330 199 A1 8/1989

(Continued)

OTHER PUBLICATIONS

Cheema et al (Arthritis and Rheumatism, 44(6):1313-1319, Jun. 2001).*
Breedveld et al . Ann Rheum Disease, 65(Suppl II):179, 2006.*
Cambridge et al Arthritis and Rheumatism, 48(8):2146-2154, Aug. 2003.*
Cope et al, Current Opinion in Immunology, 16:780-786, 2004.*
Cambridge et al, Arthritis and Rheutamism, 54(3):723-732, 2006.*
Rastetter et al Annu. Rev. Med, 55:477-503, 2004.*
Ghielmini et al (Blood, 103(12):4416-4423, 2004; published on line Feb. 19, 2004).*
De Vita et al (Arthritis & Rheumatism, 46(8):2029-2033, 2002).*
U.S. Appl. No. 60/182,938, filed Feb. 16, 2000, Ashkenazi et al.
U.S. Appl. No. 60/226,986, filed Aug. 22, 2000, Ashkenazi et al.
U.S. Appl. No. 09/724,341, filed Nov. 28, 2000, Ashkenazi et al.
U.S. Appl. No. 60/310,114, filed Aug. 3, 2001, Grewal et al.
U.S. Appl. No. 60/377,171, filed Apr. 30, 2002, Dixit et al.
Allen et al., "CD40 ligand gene defects responsible for X-linked hyper-IgM syndrome," *Science* 259:990-3 (1993).
Amakawa et al., "The Hodgkin disease antigen CD30 is crucial for antigen induced death of developing T cells," *Cold Spring Harbor Laboratory Symposium on Programmed Cell Death*, Abstract No. 10 (1995).

(Continued)

*Primary Examiner* — Patricia Duffy
(74) *Attorney, Agent, or Firm* — Clark & Elbing LLP; Karen L. Elbing

(57) ABSTRACT

The present invention relates to novel methods for treating diseases and monitoring B cell levels in subjects and kit and compositions relating thereto by measuring serum BAFF levels in the subjects.

21 Claims, 6 Drawing Sheets

(56) References Cited

U.S. PATENT DOCUMENTS

| | | |
|---|---|---|
| 6,509,170 B1 | 1/2003 | Yu et al. |
| 6,528,624 B1 | 3/2003 | Idusogie et al. |
| 6,538,124 B1 | 3/2003 | Idusogie et al. |
| 6,541,224 B2 | 4/2003 | Yu et al. |
| 6,551,795 B1 | 4/2003 | Rubenfield et al. |
| 6,565,827 B1 | 5/2003 | Kaminski et al. |
| 6,652,852 B1 | 11/2003 | Robinson et al. |
| 6,682,734 B1 | 1/2004 | Anderson et al. |
| 6,869,605 B2 | 3/2005 | Browning et al. |
| 6,875,846 B2 | 4/2005 | Rennert et al. |
| 7,083,785 B2 | 8/2006 | Browning et al. |
| 2001/0018041 A1 | 8/2001 | Hanna et al. |
| 2002/0004587 A1 | 1/2002 | Miller et al. |
| 2002/0006404 A1 | 1/2002 | Hanna et al. |
| 2002/0009427 A1 | 1/2002 | Wolin et al. |
| 2002/0009444 A1 | 1/2002 | Grillo-Lopez |
| 2002/0012665 A1 | 1/2002 | Hanna |
| 2002/0037852 A1 | 3/2002 | Browning et al. |
| 2002/0041847 A1 | 4/2002 | Goldenberg |
| 2002/0058029 A1 | 5/2002 | Hanna |
| 2002/0081296 A1 | 6/2002 | Theill et al. |
| 2002/0086018 A1 | 7/2002 | Theill et al. |
| 2002/0128488 A1 | 9/2002 | Yamakawa et al. |
| 2002/0136719 A1 | 9/2002 | Shenoy et al. |
| 2002/0165156 A1 | 11/2002 | Browning et al. |
| 2002/0172674 A1 | 11/2002 | Jeffrey et al. |
| 2002/0197255 A1 | 12/2002 | Anderson et al. |
| 2002/0197256 A1 | 12/2002 | Grewal |
| 2003/0012783 A1 | 1/2003 | Kindsvogel |
| 2003/0021781 A1 | 1/2003 | Anderson et al. |
| 2003/0023038 A1 | 1/2003 | Rennert et al. |
| 2003/0026801 A1 | 2/2003 | Weiner et al. |
| 2003/0059937 A1 | 3/2003 | Ruben et al. |
| 2003/0068664 A1 | 4/2003 | Albitar et al. |
| 2003/0082172 A1 | 5/2003 | Anderson et al. |
| 2003/0082175 A1 | 5/2003 | Schneider et al. |
| 2003/0092164 A1 | 5/2003 | Gross et al. |
| 2003/0095963 A1 | 5/2003 | Anderson et al. |
| 2003/0095967 A1 | 5/2003 | MacKay et al. |
| 2003/0099990 A1 | 5/2003 | Hsu |
| 2003/0103971 A1 | 6/2003 | Hariharan et al. |
| 2003/0133930 A1 | 7/2003 | Goldenberg et al. |
| 2003/0147885 A1 | 8/2003 | Anderson et al. |
| 2003/0157108 A1 | 8/2003 | Presta |
| 2003/0180292 A1 | 9/2003 | Hanna et al. |
| 2003/0185796 A1 | 10/2003 | Wolin et al. |
| 2003/0194743 A1 | 10/2003 | Beltzer et al. |
| 2003/0219433 A1 | 11/2003 | Hansen et al. |
| 2003/0219818 A1 | 11/2003 | Bohen et al. |
| 2004/0093621 A1 | 5/2004 | Shitara et al. |
| 2004/0103404 A1 | 5/2004 | Naumovich et al. |
| 2005/0095243 A1 | 5/2005 | Chan et al. |
| 2006/0240517 A1 | 10/2006 | Ambrose et al. |
| 2006/0240519 A1 | 10/2006 | Ambrose et al. |
| 2006/0240520 A1 | 10/2006 | Ambrose et al. |
| 2007/0269443 A1* | 11/2007 | Kalled .............. A61K 38/177 424/153.1 |
| 2008/0268480 A1* | 10/2008 | Hsu et al. .................. 435/7.92 |

FOREIGN PATENT DOCUMENTS

| | | |
|---|---|---|
| EP | 0 332 865 A2 | 9/1989 |
| EP | 0 417 563 B1 | 7/1990 |
| EP | 0 869 180 A1 | 10/1998 |
| EP | 0 870 827 A2 | 10/1998 |
| EP | 0 911 633 A1 | 4/1999 |
| JP | 2004-509615 A | 4/2004 |
| JP | 2005-517025 A | 6/2005 |
| WO | WO 95/03770 A1 | 2/1995 |
| WO | WO 97/01633 A1 | 1/1997 |
| WO | WO 97/25428 A1 | 7/1997 |
| WO | WO 97/33902 A1 | 9/1997 |
| WO | WO 98/18921 A1 | 5/1998 |
| WO | WO 98/27114 A2 | 6/1998 |
| WO | WO 98/28426 A2 | 7/1998 |
| WO | WO 98/32856 A1 | 7/1998 |
| WO | WO 98/35986 A1 | 8/1998 |
| WO | WO 98/39361 A1 | 9/1998 |
| WO | WO 98/41629 A2 | 9/1998 |
| WO | WO 98/46643 A1 | 10/1998 |
| WO | WO 98/46751 A1 | 10/1998 |
| WO | WO 98/51793 A1 | 11/1998 |
| WO | WO 98/55620 A1 | 12/1998 |
| WO | WO 98/55621 A1 | 12/1998 |
| WO | WO 98/56418 A1 | 12/1998 |
| WO | WO 98/58964 A1 | 12/1998 |
| WO | WO 99/00518 A1 | 1/1999 |
| WO | WO 99/02653 A1 | 1/1999 |
| WO | WO 99/04001 A1 | 1/1999 |
| WO | WO 99/07738 A1 | 2/1999 |
| WO | WO 99/09165 A1 | 2/1999 |
| WO | WO 99/11791 A2 | 3/1999 |
| WO | WO 99/12964 A2 | 3/1999 |
| WO | WO 99/12965 A2 | 3/1999 |
| WO | WO 99/19490 A1 | 4/1999 |
| WO | WO 99/22764 A1 | 5/1999 |
| WO | WO 99/28462 A2 | 6/1999 |
| WO | WO 99/33980 A2 | 7/1999 |
| WO | WO 99/33988 A1 | 7/1999 |
| WO | WO 99/35170 A2 | 7/1999 |
| WO | WO 99/50416 A1 | 10/1999 |
| WO | WO 99/51642 A1 | 10/1999 |
| WO | WO 00/09160 A1 | 2/2000 |
| WO | WO 00/20864 A1 | 4/2000 |
| WO | WO 00/24811 A1 | 5/2000 |
| WO | WO 00/26244 A2 | 5/2000 |
| WO | WO 00/27428 A1 | 5/2000 |
| WO | WO 00/27433 A1 | 5/2000 |
| WO | WO 00/39295 A1 | 7/2000 |
| WO | WO 00/40716 A2 | 7/2000 |
| WO | WO 00/42072 A2 | 7/2000 |
| WO | WO 00/43032 A2 | 7/2000 |
| WO | WO 00/44788 A1 | 8/2000 |
| WO | WO 00/45836 A1 | 8/2000 |
| WO | WO 00/50597 A2 | 8/2000 |
| WO | WO 00/50633 A1 | 8/2000 |
| WO | WO 00/58362 A1 | 10/2000 |
| WO | WO 00/67034 A1 | 11/2000 |
| WO | WO 00/67795 A1 | 11/2000 |
| WO | WO 00/67796 A1 | 11/2000 |
| WO | WO 00/68378 A1 | 11/2000 |
| WO | WO 00/74718 A1 | 12/2000 |
| WO | WO 00/76542 A1 | 12/2000 |
| WO | WO 01/03734 A1 | 1/2001 |
| WO | WO 01/10460 A1 | 2/2001 |
| WO | WO 01/10461 A1 | 2/2001 |
| WO | WO 01/10462 A1 | 2/2001 |
| WO | WO 01/12812 A2 | 2/2001 |
| WO | WO 01/13945 A1 | 3/2001 |
| WO | WO 01/24811 A1 | 4/2001 |
| WO | WO 01/25256 A2 | 4/2001 |
| WO | WO 01/34194 A1 | 5/2001 |
| WO | WO 01/58949 A2 | 8/2001 |
| WO | WO 01/60397 A1 | 8/2001 |
| WO | WO 01/72333 A1 | 10/2001 |
| WO | WO 01/74388 A1 | 10/2001 |
| WO | WO 01/77342 A1 | 10/2001 |
| WO | WO 01/80844 A2 | 11/2001 |
| WO | WO 01/81417 A2 | 11/2001 |
| WO | WO 01/85782 A2 | 11/2001 |
| WO | WO 01/87977 A2 | 11/2001 |
| WO | WO 01/87979 A2 | 11/2001 |
| WO | WO 01/96528 A2 | 12/2001 |
| WO | WO 01/97858 A2 | 12/2001 |
| WO | WO 02/02641 A1 | 1/2002 |
| WO | WO 02/04021 A1 | 1/2002 |
| WO | WO 02/16312 A2 | 2/2002 |
| WO | WO 02/16412 A2 | 2/2002 |
| WO | WO 02/18620 A2 | 3/2002 |
| WO | WO 02/24909 A2 | 3/2002 |
| WO | WO 02/34790 A1 | 5/2002 |
| WO | WO 02/38766 A2 | 5/2002 |
| WO | WO 02/060485 A2 | 8/2002 |

(56) References Cited

FOREIGN PATENT DOCUMENTS

| WO | WO 02/060955 A2 | 8/2002 |
|---|---|---|
| WO | WO 02/066516 A2 | 8/2002 |
| WO | WO 02/079255 A1 | 10/2002 |
| WO | WO 02/092620 A2 | 11/2002 |
| WO | WO 02/094192 A2 | 11/2002 |
| WO | WO 02/094852 A2 | 11/2002 |
| WO | WO 02/096948 A2 | 12/2002 |
| WO | WO 02/102312 A2 | 12/2002 |
| WO | WO 03/002607 A1 | 1/2003 |
| WO | WO 03/014294 A2 | 2/2003 |
| WO | WO 03/024991 A2 | 3/2003 |
| WO | WO 03/033658 A2 | 4/2003 |
| WO | WO 03/035846 A2 | 5/2003 |
| WO | WO 03/045421 A1 | 6/2003 |
| WO | WO 03/049694 A2 | 6/2003 |
| WO | WO 03/055979 A2 | 7/2003 |
| WO | WO 03/061694 A1 | 7/2003 |
| WO | WO-03/067221 A2 | 8/2003 |
| WO | WO 03/068821 A2 | 8/2003 |
| WO | WO-2004/003142 A2 | 1/2004 |
| WO | WO 2004/011611 A2 | 2/2004 |
| WO | WO 2004/032828 A2 | 4/2004 |
| WO | WO 2004/035607 A2 | 4/2004 |
| WO | WO 2004/056312 A2 | 7/2004 |
| WO | WO 2004/074511 | 9/2004 |
| WO | WO 2004/081043 A2 | 9/2004 |
| WO | WO-2004/104185 A1 | 12/2004 |
| WO | WO 2005/000351 A2 | 1/2005 |
| WO | WO 2005/005462 A2 | 1/2005 |
| WO | WO-2005/108986 A1 | 11/2005 |
| WO | WO 2006/073941 A2 | 7/2006 |

OTHER PUBLICATIONS

Anderson et al., "Expression of human B cell-associated antigens on leukemias and lymphomas: a model of human B cell differentiation," *Blood* 63:1424-33 (1984).
Anderson et al., "A homologue of the TNF receptor and its ligand enhance T-cell growth and dendritic-cell function," *Nature* 390:175-9 (1997).
Anolik and Aringer, "New treatments for SLE: cell-depleting and anti-cytokine therapies," *Best Pract. Res. Clin. Rheumatol.* 19:859-78 (2005).
Armitage et al., "Molecular and biological characterization of a murine ligand for CD40," *Nature* 357:80-2 (1992).
Aruffo et al., "CD44 is the principal cell surface receptor for hyaluronate," *Cell* 61:1303-13 (1990).
Aruffo et al., "The CD40 ligand, gp39, is defective in activated T cells from patients with X-linked hyper-IgM syndrome," *Cell* 72:291-300 (1993).
Ashkenazi and Dixit, "Death receptors: signaling and modulation," *Science* 281:1305-8 (1998).
Ashkenazi et al., "Protection against endotoxic shock by a tumor necrosis factor receptor immunoadhesin," *Proc. Natl. Acad. Sci. USA* 88:10535-9 (1991).
Bachmann et al., "TRANCE, a tumor necrosis factor family member critical for CD40 ligand-independent T helper cell activation," *J. Exp. Med.* 189:1025-31 (1999).
Baldwin, "The NF-κB and IκB proteins: new discoveries and insights," *Annu. Rev. Immunol.* 14:649-83 (1996).
Banner et al., "Crystal structure of the soluble human 55 kd TNF receptor-human TNFβ complex: implications for TNF receptor activation," *Cell* 73:431-45 (1993).
Barbas et al., "In vitro evolution of a neutralizing human antibody to human immunodeficiency virus type 1 to enhance affinity and broaden strain cross-reactivity," *Proc. Natl. Acad. Sci. USA* 91:3809-13 (1994).
Batten et al., "BAFF mediates survival of peripheral immature B lymphocytes", *J. Exp. Med.* 192:1453-65 (2000).
Bodmer et al., "TRAMP, a novel apoptosis-mediating receptor with sequence homology to tumor necrosis factor receptor 1 and Fas(Apo-1/CD95)," *Immunity* 6:79-88 (1997).

Bodmer et al., "The molecular architecture of the TNF superfamily," *Trends Biochem. Sci.* 27:19-26 (2002).
Bost and Pascual, "Antibodies against a peptide sequence within the HIV envelope protein crossreacts with human interleukin-2," *Immunol. Invest.* 17:577-86 (1988).
Brockhaus et al., "Identification of two types of tumor necrosis factor receptors on human cell lines by monoclonal antibodies," *Proc. Natl. Acad. Sci. USA* 87:3127-31 (1990).
Brojatsch et al., "CAR1, a TNFR-related protein, is a cellular receptor for cytopathic avian leukosis-sarcoma viruses and mediates apoptosis," *Cell* 87:845-55 (1996).
Browning et al., "Lymphotoxin β, a novel member of the TNF family that forms a heteromeric complex with lymphotoxin on the cell surface," *Cell* 72:847-56 (1993).
Callard et al., "CD40 ligand and its role in X-linked hyper-IgM syndrome," *Immunol. Today* 14:559-64 (1993).
Cathcart et al., "Experimental arthritis in a nonhuman primate. I. Induction by bovine type II collagen," *Lab. Invest.* 54:26-31 (1986).
Chamow and Ashkenazi, "Immunoadhesins: principles and applications," *Trends Biotechnol.* 14:52-60 (1996).
Cheema et al., "Elevated serum B lymphocyte stimulator levels in patients with systemic immune-based rheumatic diseases," *Arthritis Rheum.* 44:1313-9 (2001).
Chicheportiche et al., "TWEAK, a new secreted ligand in the tumor necrosis factor family that weakly induces apoptosis," *J. Biol. Chem.* 272:32401-10 (1997).
Chinnaiyan et al., "Signal transduction by DR3, a death domain-containing receptor related to TNFR-1 and CD95," *Science* 274:990-2 (1996).
Clark and Ledbetter, "Structure, function, and genetics of human B cell-associated surface molecules," *Adv. Cancer Res.* 52:81-149 (1989).
Courtenay et al., "Immunisation against heterologous type II collagen induces arthritis in mice," *Nature* 283:666-8 (1980).
Cragg et al., "Complement-mediated lysis by anti-CD20 mAb correlates with segregation into lipid rafts," *Blood* 101:1045-52 (2003).
Craxton et al., "A role for zTNF4/APRIL in the co-stimulation of B cell proliferation by macrophages," *Experimental Biology 2002: Meeting Abstracts*, Abstract 516.51:A704-5 (2002).
Cyster, "B cells on the front line," *Nat. Immunol.* 1:9-10 (2000).
Dealtry et al., "DNA fragmentation and cytotoxicity caused by tumor necrosis factor is enhanced by interferon-γ," *Eur. J. Immunol.* 17:689-93 (1987).
Degli-Esposti et al., "The novel receptor TRAIL-R4 induces NF-κB and protects against TRAIL-mediated apoptosis, yet retains an incomplete death domain," *Immunity* 7:813-20 (1997).
Degli-Esposti et al., "Cloning and characterization of TRAIL-R3, a novel member of the emerging TRAIL receptor family," *J. Exp. Med.* 186:1165-70 (1997).
De Vita et al., "Efficacy of selective B cell blockade in the treatment of rheumatoid arthritis: evidence for a pathogenetic role of B cells," *Arthritis Rheum.* 46:2029-33 (2002).
Do et al., "Attenuation of apoptosis underlies B lymphocyte stimulator enhancement of humoral immune response," *J. Exp. Med.* 192:953-64 (2000).
Domingues, "Rational design strategies to improve cytokine foldability and minimization of a functional motif: the IL-4 case," Thesis, University of Utrecht, p. 48, line 25 through p. 51, line 6; p. 94, Table III (May 26, 1999).
Durie et al., "Prevention of collagen-induced arthritis with an antibody to gp39, the ligand for CD40," *Science* 261:1328-30 (1993).
Durie et al., "The role of CD40 in the regulation of humoral and cell-mediated immunity," *Immunol. Today* 15:406-11 (1994).
Edwards et al., "Sustained improvement in rheumatoid arthritis following a protocol designed to deplete B lymphocytes," *Rheumatology* 40:205-11 (2001).
Edwards et al., "B-lymphocyte depletion therapy in rheumatoid arthritis and other autoimmune disorders," *Biochemical Society Transactions* 30:824-8 (2002).

(56) References Cited

OTHER PUBLICATIONS

Edwards et al., "Efficacy and safety of rituximab, a B-cell targeted chimeric monoclonal antibody: a randomized, placebo controlled trial in patients with rheumatoid arthritis," *Arthritis Rheum.* 46:S197 (2002).
Emery et al., "Osteoprotegerin is a receptor for the cytotoxic ligand TRAIL," *J. Biol. Chem.* 273:14363-7 (1998).
Flanagan and Leder, "The kit ligand: a cell surface molecule altered in steel mutant fibroblasts," *Cell* 63:185-94 (1990).
Foy et al., "gp39-CD40 interactions are essential for germinal center formation and the development of B cell memory," *J. Exp. Med.* 180:157-63 (1994).
Foy et al., "Immune regulation by CD40 and its ligand GP39," *Annu. Rev. Immunol.* 14:591-617 (1996).
Francisco et al., "In vivo efficacy and toxicity of a single-chain immunotoxin targeted to CD40," *Blood* 89:4493-500 (1997).
Fütterer et al., "The lymphotoxin β receptor controls organogenesis and affinity maturation in peripheral lymphoid tissues," *Immunity* 9:59-70 (1998).
GenBank accession No. AF046888.
GenBank accession No. AF136293.
GenBank accession No. AK008142.
GenBank accession No. AI250289, XP002206618.
GenBank accession No. Z99716.4, XP002206619.
Glennie and van de Winkel, "Renaissance of cancer therapeutic antibodies," *Drug Discov. Today* 8:503-10 (2003).
Golstein, "Cell death: TRAIL and its receptors," *Curr. Biol.* 7:R750-3 (1997).
Goodwin et al., "Molecular and biological characterization of a ligand for CD27 defines a new family of cytokines with homology to tumor necrosis factor," *Cell* 73:447-56 (1993).
Goodwin et al., "Molecular cloning and expression of the type 1 and type 2 murine receptors for tumor necrosis factor," *Mol. Cell. Biol.* 11:3020-6 (1991).
Goodwin et al., "Molecular cloning of a ligand for the inducible T cell gene 4-1BB: a member of an emerging family of cytokines with homology to tumor necrosis factor," *Eur. J. Immunol.* 23:2631-41 (1993).
Gordon et al., "BAFF/BLyS receptor 3 comprises a minimal TNF receptor-like module that encodes a highly focused ligand-binding site," *Biochemistry* 42:5977-83 (2003).
Gorman et al., "B cell depletion in autoimmune disease," *Arthritis Res. Ther.* 5:S17-21 (2003).
Gras et al., "BCMAp: an integral membrane protein in the Golgi apparatus of human mature B lymphocytes," *Int. Immunol.* 7:1093-106 (1995).
Gray, "Recruitment of virgin B cells into an immune response is restricted to activation outside lymphoid follicles," *Immunology* 65:73-9 (1988).
Green and Flavell, "TRANCE-RANK, a new signal pathway involved in lymphocyte development and T cell activation," *J. Exp. Med.* 189:1017-20 (1999).
Grewal et al., "Requirement for CD40 ligand in costimulation induction, T cell activation, and experimental allergic encephalomyelitis," *Science* 273:1864-7 (1996).
Groom et al., "Association of BAFF/BLyS overexpression and altered B cell differentiation with Sjögren's syndrome," *J. Clin. Invest.* 109:59-68 (2002).
Gross et al., "TACI and BCMA are receptors for a TNF homologue implicated in B-cell autoimmune disease," *Nature* 404:995-9 (2000).
Gruss and Dower, "Tumor necrosis factor ligand superfamily: involvement in the pathology of malignant lymphomas," *Blood* 85:3378-404 (1995).
Hahne et al., "APRIL, a new ligand of the tumor necrosis factor family, stimulates tumor cell growth," *J. Exp. Med.* 188:1185-90 (1998).

Hale et al., "Demonstration of in vitro and in vivo efficacy of two biologically active human soluble TNF receptors expressed in *E. coli*," *J. Cell. Biochem.* (abstract only) Supplement 15F:113 (P424) (1991).
Han et al., "Cellular interaction in germinal centers: roles of CD40 ligand and B7-2 in established germinal centers," *J. Immunol.* 155:556-67 (1995).
Hansen et al., "Genetic profile of insertion mutations in mouse leukemias and lymphomas," *Genome Res.* 10:237-43 (2000).
Harbury et al., "A switch between two-, three-, and four-stranded coiled coils in GCN4 leucine zipper mutants," *Science* 262:1401-7 (1993).
Hathcock et al., "Identification of an alternative CTLA-4 ligand costimulatory for T cell activation," *Science* 262:905-7 (1993).
Hawkins et al., "Selection of phage antibodies by binding affinity: mimicking affinity maturation," *J. Mol. Biol.* 226:889-96 (1992).
Higashida et al., "Treatment of DMARD-refractory rheumatoid arthritis with rituximab," Presented at the Annual Scientific Meeting of the American College of Rheumatology, New Orleans, LA (2002).
Hoag et al., "A quantitative-trait locus controlling peripheral B-cell deficiency maps to mouse Chromosome 15," *Immunogenetics* 51:924-9 (2000).
Hohmann et al., "Two different cell types have different major receptors for human tumor necrosis factor (TNFα)," *J. Biol. Chem.* 264:14927-34 (1989).
Holmdahl et al., "Role of T lymphocytes in murine collagen induced arthritis," *Agents Actions* 19:295-305 (1986).
Holmes et al., "Structure and functional expression of a human interleukin-8 receptor," *Science* 253:1278-80 (1991).
Hoogenboom et al., "Construction and expression of antibody-tumor necrosis factor fusion proteins," *Mol. Immunol.* 28:1027-37 (1991).
Hymowitz et al., "Triggering cell death: the crystal structure of Apo2L/TRAIL in a complex with Death Receptor 5," *Mol. Cell* 14:563-71 (1999).
Idusogie et al., "Mapping of the C1q binding site on rituxan, a chimeric antibody with a human IgG1 Fc," *J. Immunol.* 164:4178-84 (2000).
International Search Report for International Application No. PCT/US00/32378, mailed Jun. 11, 2001.
International Search Report for International Application No. PCT/US01/28006, mailed Mar. 28, 2003.
International Search Report for International Application No. PCT/US02/23487, mailed Jan. 31, 2006.
Itoh et al., "The polypeptide encoded by the cDNA for human cell surface antigen Fas can mediate apoptosis," *Cell* 66:233-43 (1991).
Jackson et al., "In vitro antibody maturation: improvement of a high affinity, neutralizing antibody against IL-1β," *J. Immunol.* 154:3310-9 (1995).
Johnson et al., "Expression and structure of the human NGF receptor," *Cell* 47:545-54 (1986).
Johnson and Chiswell, "Human antibody engineering," *Curr. Opin. Struc. Biol.* 3:564-71 (1993).
Joosten et al., "Anticytokine treatment of established type II collagen-induced arthritis in DBA/1 mice: a comparative study using anti-TNFα, anti-IL-1α/β, and IL-1Ra," *Arthritis Rheum.* 39:797-809 (1996).
Josien et al., "TRANCE, a tumor necrosis factor family member, enhances the longevity and adjuvant properties of dendritic cells in vivo," *J. Exp. Med.* 191:495-501 (2000).
Josien et al., "TRANCE, a TNF family member, is differentially expressed on T cell subsets and induces cytokine production in dendritic cells," *J. Immunol.* 162:2562-8 (1999).
Kalled et al., "BAFF: B cell survival factor and emerging therapeutic target for autoimmune disorders," *Expert Opin. Ther. Targets* 7:115-23 (2003).
Kashii et al., "Constitutive expression and role of the TNF family ligands in apoptotic killing of tumor cells by human NK cells," *J. Immunol.* 163:5358-66 (1999).
Kato et al., "Affinity maturation in Lyn kinase-deficient mice with defective germinal center formation," *J. Immunol.* 160:4788-95 (1998).

(56) References Cited

OTHER PUBLICATIONS

Kawabe et al., "The immune responses in CD40-deficient mice: impaired immunoglobulin class switching and germinal center formation," *Immunity* 1:167-78 (1994).
Kayagaki et al., "BAFF/BLyS receptor 3 binds the B cell survival factor BAFF ligand through a discrete surface loop and promotes processing of NF-κB2," *Immunity* 10:515-24 (2002).
Kelly et al., "APRIL/TRDL-1, a tumor necrosis factor-like ligand, stimulates cell death," *Cancer Res.* 60:1021-7 (2000).
Khare et al., "Severe B cell hyperplasia and autoimmune disease in TALL-1 transgenic mice," *Proc. Natl. Acad. Sci. USA* 97:3370-5 (2000).
Khare and Hsu, "The role of TALL-1 and APRIL in immune regulation," *Trends Immunol.* 22:61-3 (2001).
Kiesel et al., "Removal of cells from a malignant B-cell line from bone marrow with immunomagnetic beads and with complement and immunoglobulin switch variant mediated cytolysis," *Leuk. Res.* 11:1119-25 (1987).
Kim et al., "Detection of human leukemia inhibitory factor by monoclonal antibody based ELISA," *J. Immunol. Methods* 156:9-17 (1992).
Kitson et al., "A death-domain-containing receptor that mediates apoptosis," *Nature* 384:372-5 (1996).
Kohno et al., "A second tumor necrosis factor receptor gene product can shed a naturally occurring tumor necrosis factor inhibitor," *Proc. Natl. Acad. Sci. USA* 87:8331-5 (1990).
Kong et al., "OPGL is a key regulator of osteoclastogenesis, lymphocyte development and lymph-node organogenesis," *Nature* 397:315-23 (1999).
Kong et al., "Activated T cells regulate bone loss and joint destruction in adjuvant arthritis through osteoprotegerin ligand," *Nature* 402:304-9 (1999).
Krammer et al., "Regulation of apoptosis in the immune system," *Curr. Opin. Immunol.* 6:279-89 (1994).
Kwon et al., "Single amino acid substitutions of $\alpha_1$-antitrypsin that confer enhancement in thermal stability," *J. Biol. Chem.* 269:9627-31 (1994).
Kwon et al., "Functions of newly identified members of the tumor necrosis factor receptor/ligand superfamilies in lymphocytes," *Curr. Opin. Immunol.* 11:340-5 (1999).
Laabi and Strasser, "Lymphocyte survival—ignorance is BLyS," *Science* 289:883-4 (2000).
Laabi et al., "A new gene, BCM, on chromosome 16 is fused to the interleukin 2 gene by a t(4;16)(q26;p13) translocation in a malignant T cell lymphoma," *EMBO J.* 11:3897-904 (1992).
Laabi et al., "The BCMA gene, preferentially expressed during B lymphoid maturation, is bidirectionally transcribed," *Nucleic Acids Res.* 22:1147-54 (1994).
Lacey et al., "Osteoprotegerin ligand is a cytokine that regulates osteoclast differentiation and activation," *Cell* 93:165-76 (1998).
Lane et al., "B cell function in mice transgenic for mCTLA-Hγ1: lack of germinal centers correlated with poor affinity maturation and class switching despite normal priming of CD4+ T cells," *J. Exp. Med.* 179:819-30 (1994).
Leandro et al., "An open study of B lymphocyte depletion in systemic lupus erythematosus," *Arthritis Rheum.* 46:2673-7 (2002).
Leandro et al., "B lymphocyte depletion in rheumatoid arthritis: early evidence for safety, efficacy and dose response," *Arthritis Rheum.* 44:S370 (2001).
Leandro et al., "Clinical outcome in 22 patients with rheumatoid arthritis treated with B lymphocyte depletion," *Ann. Rheum. Dis.* 61:883-8 (2002).
Ledbetter et al., "Agonistic activity of a CD40-specific single-chain Fv constructed from the variable regions of mAb G28-5," *Crit. Rev. Immunol.* 17:427-35 (1997).
Lenschow et al., "CD28/B7 system of T cell costimulation," *Annu. Rev. Immunol.* 14:233-58 (1996).
Lentz et al., "Bcmd governs recruitment of new B cells into the stable peripheral B cell pool in the A/WySnJ mouse," *J. Immunol.* 157:598-606 (1996).
Lentz et al., "Bcmd decreases the life span of B-2 but not B-1 cells in A/WySnJ mice," *J. Immunol.* 160:3743-7 (1998).
Lesley et al., "Reduced competitiveness of autoantigen-engaged B cells due to increased dependence on BAFF," *Immunity* 20:441-53 (2004).
Levine and Pestronk, "IgM antibody-related polyneuropathies: B-cell depletion chemotherapy using rituximab," *Neurology* 52:1701-4 (1999).
Lewis et al., "Cloning and expression of cDNAs for two distinct murine tumor necrosis factor receptors demonstrate one receptor is species specific," *Proc. Natl. Acad. Sci. USA* 88:2830-4 (1991).
Linsley et al., "Immunosuppression in vivo by a soluble form of the CTLA-4 T cell activation molecule," *Science* 257:792-5 (1992).
Locksley et al., "The TNF and TNF receptor superfamilies: integrating mammalian biology," *Cell* 104:487-501 (2001).
Loetscher et al., "Molecular cloning and expression of the human 55 kd tumor necrosis factor receptor," *Cell* 61:351-9 (1990).
Lotz et al., "The nerve growth factor/tumor necrosis factor receptor family," *J. Leukocyte Biol.* 60:1-7 (1996).
MacFarlane et al., "Identification and molecular cloning of two novel receptors for the cytotoxic ligand TRAIL," *J. Biol. Chem.* 272:25417-20 (1997).
Mackay and Browning, "BAFF: a fundamental survival factor for B cells," *Nature Rev. Immunol.* 2:465-75 (2002).
McKay et al., "Belimumab, a fully human monoclonal antibody to B-lymphocyte stimulator (BLyS), combined with standard of care therapy reduces the signs and symptoms of rheumatoid arthritis in a heterogeneous subject population," 69th Annual Scientific Meeting of the American College of Rheumatology/Associate of Rheumatology Heath Professionals, Oral Presentation #1920 (Nov. 16, 2005).
Mackay et al., "Mice transgenic for BAFF develop lymphocytic disorders along with autoimmune manifestations," *J. Exp. Med.* 190:1697-710 (1999).
Mackay et al., "BAFF and APRIL: a tutorial on B cell survival," *Annu. Rev. Immunol.* 21:231-64 (2003).
MacLennan, "Germinal centers," *Annu. Rev. Immunol.* 12:117-39 (1994).
Madry et al., "The characterization of murine BCMA gene defines it as a new member of the tumor necrosis factor receptor superfamily," *Int. Immunol.* 10:1693-702 (1998).
Maini et al., "Monodonal anti-TNFα antibody as a probe of pathogenesis and therapy of rheumatoid disease," *Immunol. Rev.* 144:195-223 (1995).
Mallett et al., "Characterization of the MRC OX40 antigen of activated CD4 positive T lymphocytes—a molecule related to nerve growth factor receptor," *EMBO J.* 9:1063-8 (1990).
Mandala et al., "Alteration of lymphocyte trafficking by sphingosine-1-phosphate receptor agonists," *Science* 296:346-9 (2002).
Marsters et al., "Apo-3, a new member of the tumor necrosis factor receptor family, contains a death domain and activates apoptosis and NF-κB," *Curr. Biol.* 6:1669-76 (1996).
Marsters et al., "Herpesvirus entry mediator, a member of the tumor necrosis factor receptor (TNFR) family, interacts with members of the TNFR-associated factor family and activates transcription factors NF-κB and AP-1," *J. Biol. Chem.* 272:14029-32 (1997).
Marsters et al., "Activation of apoptosis by Apo-2 ligand is independent of FADD but blocked by CrmA," *Curr. Biol.* 6:750-2 (1996).
Marsters et al., "A novel receptor for Apo2L/TRAIL contains a truncated death domain," *Curr. Biol.* 7:1003-6 (1997).
Marsters et al., "Identification of a ligand for the death-domain-containing receptor Apo3," *Curr. Biol.* 8:525-8 (1998).
Marsters et al., "Interaction of the TNF homologues BLyS and APRIL with the TNF receptor homologues BCMA and TACI," *Curr. Biol.* 10:785-8 (2000).
Matsumoto et al., "Affinity maturation without germinal centres in lymphotoxin-α-deficient mice," *Nature* 382:462-6 (1996).
Matthews, "Medical heretics," *New Scientist* 170:34-7 (2001).
Mauri et al., "LIGHT, a new member of the TNF superfamily, and lymphotoxin α are ligands for herpesvirus entry mediator," *Immunity* 8:21-30 (1998).

(56) References Cited

OTHER PUBLICATIONS

McCafferty et al., "Phage antibodies: filamentous phage displaying antibody variable domains," *Nature* 348:552-4 (1990).
Mongkolsapaya et al., "Cutting edge: lymphocyte inhibitor of TRAIL (TNF-related apoptosis-inducing ligand): a new receptor protecting lymphocytes from the death ligand TRAIL," *J. Immunol.* 160:3-6 (1998).
Montgomery et al., "Herpes simplex virus-1 entry into cells mediated by a novel member of the TNF/NGF receptor family," *Cell* 87:427-36 (1996).
Moore et al., "BLyS: member of the tumor necrosis factor family and B lymphocyte stimulator," *Science* 285:260-3 (1999).
Morimoto et al., "Abnormalities in CD4+ T-lymphocyte subsets in inflammatory rheumatic diseases," *Am. J. Med.* 84:817-25 (1988).
Mukhopadhyay et al., "Identification and characterization of a novel cytokine, THANK, a TNF homologue that activates apoptosis, nuclear factor-κB, and c-Jun $NH_2$-terminal kinase," *J. Biol. Chem.* 274:15978-81 (1999).
Nagata and Golstein, "The Fas death factor," *Science* 267:1449-56 (1995).
Nagata, "Apoptosis by death factor," *Cell* 88:355-65 (1997).
Nardelli et al., "Synthesis and release of B-lymphocyte stimulator from myeloid cells," *Blood* 97:198-204 (2001).
Nocentini et al., "A new member of the tumor necrosis factor/nerve growth factor receptor family inhibits T cell receptor-induced apoptosis," *Proc. Natl. Acad. Sci. USA* 94:6216-21 (1997).
Nophar et al., "Soluble forms of tumor necrosis factor receptors (TNF-Rs). The cDNA for the type I TNF-R, cloned using amino acid sequence data of its soluble form, encodes both the cell surface and a soluble form of the receptor," *EMBO J.* 9:3269-78 (1990).
Pan et al., "TRUNDD, a new member of the TRAIL receptor family that antagonizes TRAIL signalling," *FEBS Lett.* 424:41-5 (1998).
Pan et al., "Identification and functional characterization of DR6, a novel death domain-containing TNF receptor," *FEBS Lett.* 431:351-6 (1998).
Pan et al., "The receptor for the cytotoxic ligand TRAIL," *Science* 276:111-3 (1997).
Pan et al., "An antagonist decoy receptor and a death domain-containing receptor for TRAIL," *Science* 277:815-8 (1997).
Pennica et al., "Human tumour necrosis factor: precursor structure, expression and homology to lymphotoxin," *Nature* 312:724-9 (1984).
Perrotta and Abuel, "Response of chronic relapsing ITP of 10 years duration to rituximab," *Blood* (Abstract 3360) 92(10 Suppl. 1 Pt. 1-2):88b (1998).
Pitti et al., "Induction of apoptosis by Apo-2 ligand, a new member of the tumor necrosis factor cytokine family," *J. Biol. Chem.* 271:12687-90 (1996).
Pitti et al., "Genomic amplification of a decoy receptor for Fas ligand in lung and colon cancer," *Nature* 396:699-703 (1998).
Pitzalis et al., "The preferential accumulation of helper-inducer T lymphocytes in inflammatory lesions: evidence for regulation by selective endothelial and homotypic adhesion," *Eur. J. Immunol.* 18:1397-404 (1988).
Potocnik et al., "Expression of activation antigens on T cells in rheumatoid arthritis patients," *Scand. J. Immunol.* 31:213-24 (1990).
Press et al., "Monoclonal antibody 1F5 (anti-CD20) serotherapy of human B cell lymphomas," *Blood* 69:584-91 (1987).
Radeke et al., "Gene transfer and molecular cloning of the rat nerve growth factor receptor," *Nature* 325:593-7 (1987).
Ravetch and Kinet, "Fc receptors," *Annu. Rev. Immunol.* 9:457-92 (1991).
Reff et al., "Depletion of B cells in vivo by a chimeric mouse human monoclonal antibody to CD20," *Blood* 83:435-45 (1994).
Rennert et al., "A soluble form of B cell maturation antigen, a receptor for the tumor necrosis factor family member APRIL, inhibits tumor cell growth," *J. Exp. Med.* 192:1677-83 (2000).
Renshaw et al., "Humoral immune responses in CD40 ligand-deficient mice," *J. Exp. Med.* 180:1889-900 (1994).
Ridley et al., "Monocyte activation in rheumatoid arthritis: evidence for in situ activation and differentiation in joints," *Br. J. Rheumatol.* 29:84-8 (1990).
Scapini et al., "G-CSF-stimulated neutrophils are a prominent source of functional BLyS," *J. Exp. Med.* 197:297-302 (2003).
Schall et al., "Molecular cloning and expression of a receptor for human tumor necrosis factor," *Cell* 61:361-70 (1990).
Schein, "Production of soluble recombinant proteins in bacteria," *Bio-Technol.* 7:1141-9 (1989).
Schiemann et al., "An essential role for BAFF in the normal development of B cells through a BCMA-independent pathway," *Science* 293:2111-4 (2001).
Schier et al., "Identification of functional and structural amino-acid residues by parsimonious mutagenesis," *Gene* 169:147-55 (1996).
Schmid et al., "DNA fragmentation: manifestation of target cell destruction mediated by cytotoxic T-cell lines, lymphotoxin-secreting helper T-cell clones, and cell-free lymphotoxin-containing supernatant," *Proc. Natl. Acad. Sci. USA* 83:1881-5 (1986).
Schneider et al., "Characterization of two receptors for TRAIL," *FEBS Lett.* 416:329-34 (1997).
Schneider et al., "BAFF, a novel ligand of the tumor necrosis factor family, stimulates B cell growth," *J. Exp. Med.* 189:1747-56 (1999).
Screaton et al., "LARD: a new lymphoid-specific death domain containing receptor regulated by alternative pre-mRNA splicing," *Proc. Natl. Acad. Sci. USA* 94:4615-9 (1997).
Screaton et al., "TRICK2, a new alternatively spliced receptor that transduces the cytotoxic signal from TRAIL," *Curr. Biol.* 7:693-6 (1997).
Search Report issued by the Eurasian Patent Office for Eurasian Patent Application No. 200400262, mailed Apr. 14, 2005.
Seki et al., "Type II collagen-induced murine arthritis: induction of arthritis depends on antigen-presenting cell function as well as susceptibility of host to an anticollagen immune response," *J. Immunol.* 148:3093-9 (1992).
Sheridan et al., "Control of TRAIL-induced apoptosis by a family of signaling and decoy receptors," *Science* 277:818-21 (1997).
Shields et al., "High resolution mapping of the binding site on human IgG1 for FcγRI, FcγRII, FcγRIII, and FcRn and design of IgG1 variants with improved binding to the FcγR*," *J. Biol. Chem.* 276:6591-604 (2001).
Shu et al., "TALL-1 is a novel member of the TNF family that is down-regulated by mitogens," *J. Leukocyte Biol.* 65:680-3 (1999).
Shu and Johnson, "B cell maturation protein is a receptor for the tumor necrosis factor family member TALL-1," *Proc. Natl. Acad. Sci. USA* 97:9156-61 (2000).
Simonet et al., "Osteoprotegerin: a novel secreted protein involved in the regulation of bone density," *Cell* 89:309-19 (1997).
Smith et al., "T2 open reading frame from the Shope Fibroma Virus encodes a soluble form of the TNF receptor," *Biochem. Biophys. Res. Commun.* 176:335-42 (1991).
Smith et al., "The TNF receptor superfamily of cellular and viral proteins: activation, costimulation, and death," *Cell* 76:959-62 (1994).
Smith et al., "CD30 antigen, a marker for Hodgkin's lymphoma, is a receptor whose ligand defines an emerging family of cytokines with homology to TNF," *Cell* 73:1349-60 (1993).
Smith et al., "A receptor for tumor necrosis factor defines an unusual family of cellular and viral proteins," *Science* 248:1019-23 (1990).
Somer et al., "Improvement in Sjögren's syndrome following therapy with rituximab for marginal zone lymphoma," *Arthritis. Rheum.* 49:394-8 (2003).
Srivastava et al., "The Tabby phenotype is caused by mutation in a mouse homologue of the EDA gene that reveals novel mouse and human exons and encodes a protein (ectodysplasin-A) with collagenous domains," *Proc. Natl. Acad. Sci. USA* 94:13069-74 (1997).
Stamenkovic et al., "A B-lymphocyte activation molecule related to the nerve growth factor receptor and induced by cytokines in carcinomas," *EMBO J.* 8:1403-10 (1989).
Stamenkovic et al., "The B lymphocyte adhesion molecule CD22 interacts with leukocyte common antigen CD45RO on T cells and α2-6 sialyltransferase, CD75, on B cells," *Cell* 66:1133-44 (1991).

(56) References Cited

OTHER PUBLICATIONS

Stasi et al., "Rituximab chimeric anti-CD20 monoclonal antibody treatment for adults with chronic idiopathic thrombocytopenic purpura," *Blood* 98:952-7 (2001).
Supplementary European Search Report for European Patent Application No. 02756618, mailed May 16, 2007.
Tartaglia et al., "Identification and expression cloning of a leptin receptor, OB-R," *Cell* 83:1263-71 (1995).
Tedder et al., "The B cell surface molecule B1 is functionally linked with B cell activation and differentiation," *J. Immunol.* 135:973-9 (1985).
Tewari and Dixit, "Recent advances in tumor necrosis factor and CD40 signaling," *Curr. Opin. Genet. Develop.* 6:39-44 (1996).
Thomas and Quinn, "Functional differentiation of dendritic cells in rheumatoid arthritis: role of CD86 in the synovium," *J. Immunol.* 156:3074-86 (1996).
Thomas et al., "Rheumatoid synovium is enriched in mature antigen-presenting dendritic cells," *J. Immunol.* 152:2613-23 (1994).
Thompson et al., "BAFF binds to the tumor necrosis factor receptor-like molecule B cell maturation antigen and is important for maintaining the peripheral B cell population," *J. Exp. Med.* 192:129-35 (2000).
Thompson et al., "BAFF-R, a newly identified TNF receptor that specifically interacts with BAFF," *Science* 293:2108-11 (2001).
Tuscano et al., "Successful treatment of Infliximab-refractory rheumatoid arthritis with rituximab," Presented at the Annual Scientific Meeting of the American College of Rheumatology, New Orleans, LA (2002).
Upton et al., "Tumorigenic poxviruses: genomic organization and DNA sequence of the telomeric region of the Shope Fibroma Virus genome," *Virology* 160:20-30 (1987).
Upton et al., "Myxoma virus expresses a secreted protein with homology to the tumor necrosis factor receptor gene family that contributes to viral virulence," *Virology* 184:370-82 (1991).
Valentine et al., "Phosphorylation of the CD20 phosphoprotein in resting B lymphocytes: regulation by protein kinase C," *J. Biol. Chem.* 264:11282-7 (1989).
Valentine et al., "Structure and function of the B-cell specific 35-37 kDa CD20 protein," *Leukocyte Typing III*, McMichael, Ed., Oxford University Press, pp. 440-443 (1987).
Van Regenmortel, "Mapping epitope structure and activity: from one-dimensional prediction to four-dimensional description of antigenic specificity," *Methods* 9:465-72 (1996).
Verma et al., "Rel/NF-κB/IκB family: intimate tales of association and dissociation," *Gene Dev.* 9:2723-35 (1995).
von Bülow and Bram, "NF-AT activation induced by a CAML-interacting member of the tumor necrosis factor receptor superfamily," *Science* 278:138-41 (1997).
von Bülow et al., "Regulation of the T-independent humoral response by TACI," *Immunity* 14:573-82 (2001).
Walczak et al., "TRAIL-R2: a novel apoptosis-mediating receptor for TRAIL," *EMBO J.* 16:5386-97 (1997).
Waldschmidt and Noelle, "Long live the mature B cell—a BAFFling mystery resolved," *Science* 293:2012-3 (2001).
Wang et al., "TACI-ligand interactions are required for T cell activation and collagen-induced arthritis in mice," *Nat. Immunol.* 2:632-7 (2001).
Ward and Mulligan, "Blocking of adhesion molecules in vivo as anti-inflammatory therapy," *Ther. Immunol.* 1:165-71 (1994).
Ware, "APRIL and BAFF connect autoimmunity and cancer," *J. Exp. Med.* 192:F35-7 (2000).
Wernick et al., "IgG and IgM rheumatoid factor synthesis in rheumatoid synovial membrane cell cultures," *Arthritis Rheum.* 28:742-52 (1985).
Wiley et al., "Identification and characterization of a new member of the TNF family that induces apoptosis," *Immunity* 3:673-82 (1995).
Wilson et al., "cDNA cloning of the B cell membrane protein CD22: a mediator of B-B cell interactions," *J. Exp. Med.* 173:137-46 (1991).
Wilson et al., "Genomic structure and chromosomal mapping of the human CD22 gene," 150:5013-24 (1993).
Wilson-Rawls et al., "The signal-anchor domain of adenovirus E3-6.7 K, a type III integral membrane protein, can direct adenovirus E3-gp19K, a type I integral membrane protein, into the membrane of the endoplasmic reticulum," *Virology* 201:66-76 (1994).
Wong et al., "TRANCE (tumor necrosis factor [TNF]-related activation-induced cytokine), a new TNF family member predominantly expressed in T cells, is a dendritic cell-specific survival factor," *J. Exp. Med.* 186:2075-80 (1997).
Wong et al., "TRANCE is a TNF family member that regulates dendritic cell and osteoclast function," *J. Leukocyte Biol.* 65:715-24 (1999).
Wood et al., "Prolines and amyloidogenicity in fragments of the Alzheimers's peptide β/A4," *Biochemistry* 34:724-30 (1995).
Wu and Wu, "Receptor-mediated in vitro gene transformation by a soluble DNA carrier system," *J. Biol. Chem.* 262:4429-32 (1987).
Wu et al., "Tumor necrosis factor (TNF) receptor superfamily member TACI is a high affinity receptor for TNF family members APRIL and BLyS," *J. Biol. Chem.* 275:35478-85 (2000).
Wu et al., "KILLER/DR5 is a DNA damage-inducible p53-regulated death receptor gene," *Nat. Genet.* 17:141-3 (1997).
Xia et al., "TACI is a TRAF-interacting receptor for TALL-1, a tumor necrosis factor family member involved in B cell regulation," *J. Exp. Med.* 192:137-43 (2000).
Xu et al., "Mice deficient for the CD40 ligand," *Immunity* 1:423-31 (1994).
Xu and Lam, "B-cell maturation protein, which binds the tumor necrosis factor family members BAFF and APRIL, is dispensible for humoral immune responses," *Mol. Cell. Biol.* 21:4067-74 (2001).
Yan et al., "Activation and accumulation of B cells in TACI-deficient mice," *Nat. Immunol.* 2:638-43 (2001).
Yan et al., "Identification of a novel receptor for B lymphocyte stimulator that is mutated in a mouse strain with severe B cell deficiency," *Curr. Biol.* 11:1547-52 (2001).
Yan et al., "Identification of a receptor for BLyS demonstrates a crucial role in humoral immunity," *Nat. Immunol.* 1:37-41 (2000).
Yasuda et al., "Identity of osteoclastogenesis inhibitory factor (OCIF) and osteoprotegerin (OPG): a mechanism by which OPG/OCIF inhibits osteoclastogenesis in vitro," *Endocrinology* 139:1329-37 (1998).
Yelton et al., "Affinity maturation of the BR96 anti-carcinoma antibody by codon-based mutagenesis," *J. Immunol.* 155:1994-2004 (1995).
Yonehara et al., "A cell-killing monoclonal antibody (anti-Fas) to a cell surface antigen co-downregulated with the receptor of tumor necrosis factor," *J. Exp. Med.* 169:1747-56 (1989).
Yu et al., "APRIL and TALL-1 and receptors BCMA and TACI: system for regulating humoral immunity," *Nat. Immunol.* 1:252-6 (2000).
Yun et al., "OPG/FDCR-1, a TNF receptor family member, is expressed in lymphoid cells and is up-regulated by ligating CD40," *J. Immunol.* 161:6113-21 (1998).
Zhang et al., "Cutting edge: a role for B lymphocyte stimulator in systemic lupus erythematosus," *J. Immunol.* 166:6-10 (2001).
Zheng et al., "Induction of apoptosis in mature T cells by tumour necrosis factor," *Nature* 377:348-51 (1995).
Eisenberg et al., "The therapeutic potential of anti-CD20: what do B-cells do?" *Clin. Immunol.* 117:207-213 (2005).
Novak et al., "Expression of BLyS and its receptors in B-cell non-Hodgkin lymphoma: correlation with disease activity and patient outcome," *Blood* 104:2247-2253 (2004).
Vallerskog et al., "Differential effects on BAFF and APRIL levels in rituximab-treated patients with systemic lupus erythematosus and rheumatoid arthritis," *Arthritis Res. Ther.* 8:R167 (2006).
Supplemental European Search Report (EP 06838235.7), mailed May 26, 2009 (search completed Apr. 27, 2009).
International Preliminary Report on Patentability (PCT/US06/45148), issued Nov. 4, 2008.

(56) References Cited

OTHER PUBLICATIONS

Written Opinion of the International Searching Authority (PCT/US06/45148), mailed Sep. 22, 2008 (opinion completed Sep. 16, 2008).
Hasegawa, "B lymphocyte," *Japanese Journal of Clinical Immunology* 28:300-308 (2005). (English abstract included).
Notice of Reasons for Rejection for Japanese Patent Application No. 2008-542424, dated May 7, 2013.
Blum et al., "Lymphocyte numbers and subsets in the human blood Do they mirror the situation in all organs?" *Immunology Letters* 108:45-51 (2007).
International Search Report (PCT/US06/45148) mailed Sep. 22, 2008.
Gorman et al., "B cell depletion in autoimmune disease," Arthritis Res Ther. 5 Suppl 4:S17-21 (2003).
Examination Report for European Patent Application No. 06838235.7, dated Jun. 19, 2015 (6 pages).
Gong et al., "Importance of cellular microenvironment and circulatory dynamics in B cell immunotherapy," J Immunol. 174(2):817-26 (2005).
Notice of Reasons for Rejection for Japanese Patent Application No. 2008-542424, issued Mar. 15, 2016 (6 pages).
Notice of Reasons for Rejection for Japanese Patent Application No. 2014-228007, issued Oct. 27, 2015 (6 pages).

\* cited by examiner

METHODS AND COMPOSITIONS RELATED TO B CELL ASSAYS

CROSS-REFERENCE TO RELATED APPLICATIONS

This application claims the benefit of U.S. Provisional Application No. 60/739,266, filed Nov. 23, 2005, and U.S. Provisional Application No. 60/857,925, entitled "Methods and Compositions Related to B Cell Assays," filed on Nov. 10, 2006, both hereby incorporated by reference.

FIELD OF THE INVENTION

The present invention relates to novel methods for treating diseases and monitoring B cell levels in subjects and kit and compositions relating thereto.

BACKGROUND OF THE INVENTION

Therapies targeted to deplete B cells have been shown to be useful in treating a wide variety of B cell mediated diseases. For example, rituximab, the RITUXAN® antibody, which is a genetically engineered chimeric murine/human monoclonal antibody directed against human CD20 antigen (commercially available from Genentech, Inc., South San Francisco, Calif., U.S.) is used for the treatment of patients with relapsed or refractory low-grade or follicular, CD20 positive, B cell non-Hodgkin's lymphoma. Results from rituximab clinical trials and case studies (Biogen Idec, Cambridge, Mass., USA and Genentech, South San Francisco, Calif., USA) report therapeutic benefits not only in patients with systemic lupus erythematosus (SLE), rheumatoid arthritis (RA), and Sjögren's syndrome (SS), but also in patients with less common autoimmune diseases such as refractory dermatomyositis, type II mixed cryoglobulinemia, Wegener's granulomatosis, autoimmune hemalytic anemia, idiopathic thrombocytopenia, and immunoglobulin M (IgM) polyneuropathies (Gorman C, et al., (2003) Arthritis Res Ther 5:S17-S21; Somer B G, et al., (2003) Arthritis Rheum 49:394-398).

Currently, the activity of B cell depleting therapies in subjects is sometimes monitored by measuring actual B cell levels in the blood during B cell depletion and repletion (recovery). Alternatively or additionally, the activity of B cell depleting therapies have been evaluated by monitoring markers in blood traditionally associated with the disease. For example, for certain autoimmune diseases, autoantibodies such as double-stranded DNA antibodies have been monitored. None of these methods give a clear, contemporaneous view of the B cell population in other areas of the subject. Obtaining biopsies of tissues (e.g., spleen, lymph nodes and joints) of patients or evaluating other bodily fluid (e.g., spinal fluid, synovial fluid) is often not an option, or at the very least, inconvenient.

One polypeptide that is elevated in several autoimmune diseases, such as systemic lupus erythematosus, rheumatoid arthritis, and Sjögren's syndrome, is the BAFF polypeptide (Cheema, G. S, et al., (2001) Arthritis Rheum. 44:1313-1319; Groom, J., et al, (2002) J. Clin. Invest. 109:59-68; Zhang, J., et al., (2001) J. Immunol. 166:6-10). BAFF (also known as BLyS, TALL-1, THANK, TNFSF13B, or zTNF4) is a member of the TNF ligand superfamily that is essential for B cell survival and maturation (reviewed in Mackay & Browning (2002) Nature Rev. Immunol. 2:465-475). BAFF can be found in secreted from or on the cell-surface of monocytes, macrophages, dendritic cells, and neutrophils, but not B cells (Nardelli B, et al. (2000) Blood 97: 198-204; Scapini P, et al. (2003) J Exp Med 197:297-302). BAFF overexpression in transgenic mice leads to B cell hyperplasia and development of severe autoimmune disease (Mackay, et al. (1999) J. Exp. Med. 190:1697-1710; Gross, et al. (2000) Nature 404:995-999; Khare, et al. (2000) Proc. Natl. Acad. Sci. U.S.A. 97:3370-33752-4).

Furthermore, BAFF levels correlate with disease severity, suggesting that BAFF may play a direct role in the pathogenesis of these illnesses. BAFF binds to three members of the TNF receptor superfamily, TACI, BCMA, and BR3 (also known as BAFF-R) (Gross, et al., supra; Thompson, J. S., et al., (2001) Science 293, 2108-2111; Yan, M., et al. (2001) Curr. Biol. 11:1547-1552; Yan, M., et al., (2000) Nat. Immunol. 1:37-41; Schiemann, B., et al., (2001) Science 293:2111-2114). Of the three, only BR3 is specific for BAFF; the other two receptors also bind the related TNF family member, APRIL. Comparison of the phenotypes of BAFF and receptor knockout or mutant mice indicates that signaling through BR3 mediates the B cell survival functions of BAFF (Thompson, et al., supra; Yan, (2002), supra; Schiemann, supra). In contrast, TACI appears to act as an inhibitory receptor (Yan, M., (2001) Nat. Immunol. 2, 638-643), while the role of BCMA is less clear (Schiemann, supra).

Currently, a blocking mAb targeting BAFF (Lymphostat-B™, Human Genome Sciences, Rockville, Md.) is in clinical trials in RA and SLE patients, TACI-Fc (ZymoGenetics, Seattle, Wash. and Serono, Geneva, CH) is in clinical trials in SLE patients and BAFF-R:Fc (also called BR3-Fc) (Biogen Idec, Cambridge, Mass. and Genentech, South San Francisco, Calif.) is in clinical development. Reports of the data from the phase II trial with Lymphostat-B™ in rheumatoid arthritis stated that patients experienced a reduction in select B cell populations (McKay, J., et al., 69th Annual Scientific Meeting of the American College of Rheumatology/Association of Rheumatology Health Professionals. Oral Presentation #1920 (Nov. 16, 2005)).

The rationale for using inhibitors of BAFF to treat B cell mediated diseases is clear. However, understanding the scope of the use of BAFF as a marker, not as a target for a therapeutic agent, and understanding when and how to use it as a marker in treatment regimens is less clear. The answer to these questions and others are described below.

SUMMARY OF THE INVENTION

The present invention relates to the discovery that serum BAFF levels is an indicator of B cell levels in subjects, including an early indicator of tissue B cell levels in subjects treated with B cell depletion or proliferating therapeutic agents, and use therefore in kits or in any methods of treatment or evaluation of subjects that would benefit from knowing the B cell levels in the subject. Furthermore, the present invention relates to the discovery that serum BAFF levels are inversely related to the levels of B cells in the tissue in a patient after treatment with a B cell therapeutic agent and the use of that knowledge in treating patients.

The present invention provides methods for monitoring B cell levels in a subject comprising the steps of determining the serum BAFF levels in a test sample of the subject, determining the serum BAFF levels in a control sample, and calculating the B cell levels in the subject relative to the control, which calculation comprises the step of comparing the serum BAFF level in the test sample to the serum BAFF level in the control sample (e.g., dividing the serum BAFF level in the test sample to the serum BAFF level in the control sample). In one embodiment, the control sample is from the subject before treatment with a therapeutic agent and the test sample is from the subject after treatment with the therapeutic agent. In another embodiment, the test sample is from the subject who is suffering from a disease and the control sample is from a subject that is not suffering from the disease. According to one embodiment, the B cells are CD19 positive and/or CD20 positive B cells. This method is useful for determining B cell levels in any subject for whom the knowledge of the B cell levels in the subject would be helpful to treat a disease. Therefore, this method can be useful for monitoring or treating subjects for any disease in which B cells are affected or should be monitored or in which the disease is treated with a B cell promoting agent or a B cell depleting agent. Thus, this method is useful for monitoring B cells in a variety of subjects, including those subjects who are not suffering from an autoimmune disease immunodeficiency, a lymphoma or a leukemia.

The present invention provides methods for treating a subject suffering from a disease comprising the steps of (1) administering a therapeutically effective amount of a therapeutic agent to the subject, (2) determining the serum BAFF levels in a test sample of the subject, (3) calculating the B cell level in the test sample relative to a control sample and (3) administering a therapeutically effective amount of the same or different therapeutic agent at a time point dependent on the serum BAFF level in the subject. In another embodiment, the invention provides methods for treating a subject suffering from a disease comprising the steps of (1) administering a therapeutically effective amount of a therapeutic agent to the subject, (2) determining the serum BAFF levels in a test sample of the subject, and (3) administering a therapeutically effective amount of the same or different therapeutic agent at a time point dependent on the serum BAFF level in the test sample. According to one embodiment, the time point is during or after the phase of maximum B cell depletion. According to another embodiment, the time point is during the B cell recovery phase. According to one preferred embodiment, the time point is before or during tissue B cell recovery that is prior to peripheral blood B cell recovery. According to one specific embodiment, the B cell recovery phase is characterized by decreasing serum BAFF levels. According to one specific embodiment, the maximum B cell depletion phase is characterized by maximum levels of BAFF in the sera of a subject.

The present invention provides methods of maintenance therapy for a subject previously treated with a B cell depletion agent comprising the step of determining the serum BAFF levels in the subject and treating the subject with a B cell depletion agent (same or different agent) or another therapeutic agent at a time point dependent on the serum BAFF level in the test sample, e.g., at maximum B cell depletion or after maximum B cell depletion and while serum BAFF levels are decreasing. According to one preferred embodiment, the time point is before or during tissue B cell recovery that is prior to peripheral blood B cell recovery.

According to this some embodiments of this invention, the therapeutic agent is selected from the group consisting of B cell promoting agent and a B cell depletion agent. According preferred embodiments, the therapeutic agent is not a BAFF antagonist that binds to BAFF. According to other embodiments, the therapeutic agent does not block BAFF from binding to BCMA, TACI or BR3 by binding to BAFF to block the interaction. According to one embodiment, the therapeutic agent is a B cell depletion agent that targets a B cell surface antigen selected from the group consisting of CD10, CD19, CD20, CD21, CD22, CD23, CD24, CD37, CD40, CD52, D53, CD72, CD73, CD74, CDw75, CDw76, CD77, CDw78, CD79a, CD79b, CD80, CD81, CD82, CD83, CDw84, CD85, CD86, CD180 (RP105), FcRH2 (IRTA4), CD79A, C79B, CR2, CCR6, CD72, P2x5, HLA-DOB, CXCR5 (BLR1), FCER2, BR3 (aka BAFF-R), TACI, BTLA, NAG14 (aka LRRC4), SLGC16270 (ala LOC283663), FcRH1 (IRTA5), FcRH5 (IRTA2), ATWD578 (aka MGC15619), FcRH3 (IRTA3), FcRH4 (IRTA1), FcRH6 (aka LOC343413) and BCMA (aka TNFRSF17), HLA-DO, HLA-Dr10 and MHC ClassII. According to one embodiment, the B cell depleting agent that targets a B cell surface antigen is a monoclonal antibody or a peptibody. According to one specific embodiment, the monoclonal antibody is a human, humanized, chimeric or otherwise engineered antibody.

According to one embodiment of this invention, the disease is an immunological disorder or a cancer. According to another embodiment, the immunological disorder is a lymphoma, leukemia or multiple myeloma. In another embodiment, the disease is a B cell lymphoma or leukemia. According to another embodiment of this invention, the disease is selected from the group consisting of an autoimmune disease, a B cell neoplasm, a B cell lymphoproliferative disorder or an immunodeficiency disease. According to one embodiment, the autoimmune disease is elected from the group consisting of rheumatoid arthritis including juvenile rheumatoid arthritis, lupus including systemic lupus erythematosus (SLE), Wegener's disease, inflammatory bowel disease, including Crohn's disease and ulcerative colitis, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome, glomerulonephritis, dermatomyositis/polymyositis, ANCA-associated vasculitis (AAV), Aplastic anemia, Autoimmune hemolytic anemia (AIHA), factor VIII deficiency, hemophilia A, Autoimmune neutropenia, Castleman's syndrome, Goodpasture's syndrome, solid organ transplant rejection, graft versus host disease (GVHD), IgM mediated, thrombotic thrombocytopenic purpura (TTP), Hashimoto's Thyroiditis, autoimmune hepatitis, lymphoid interstitial pneumonitis (LIP), bronchiolitis obliterans (non-transplant) vs. NSIP, Guillain-Barre Syndrome, large vessel vasculitis, giant cell (Takayasu's) arteritis, medium vessel vasculitis, Kawasaki's Disease, polyarteritis nodosa, Neuromyelitis Optica (NMO), IgG neuropathy and Myasthenia Gravis and pemphigus vulgaris. According to another embodiment, the lymphoma or leukemia is a B cell lymphoma or leukemia. According to one specific embodiment, the disease is selected from the group consisting of non-Hodgkin's lymphoma (NHL) or lymphocyte predominant Hodgkin's disease (LPHD), chronic lymphocytic leukemia (CLL), acute lymphocytic leukemia (ALL), small lymphocytic lymphoma (SLL), and multiple myeloma.

According to some embodiments, the B cell depleting agent is selected from the group consisting of an anti-CD20 antibody, an anti-BR3 antibody, an anti-CD22 antibody and an anti-CD52 antibody. In any of the embodiments of the methods, compositions and articles of manufacture of the invention, the anti-CD20 antibody can be a chimeric, human, humanized otherwise engineered antibody. According to one embodiment, the anti-BR3 antibody comprises a VH and a VL domain described herein.

Specific embodiments of the anti-CD20 antibody include rituximab (RITUXAN®), m2H7 (murine 2H7), hu2H7 (humanized 2H7) and all its functional variants, hu2H7.v16 (v stands for version), v31, v96, v114 and v115, (e.g., see, WO 2004/056312). According to other embodiments, the B cell promoting agent is selected from the group consisting of a cytokine or antibody that stimulates B cell proliferation or survival. The B cell promoting agent is preferably not BAFF.

The present invention also provides kits and articles of manufacture comprising instructions for assaying serum BAFF levels in a subject after administration of a therapeutic agent and uses of the assay results for setting up retreatment regimes. The present invention also provides kits comprising instructions for assaying serum BAFF levels in a subject and uses of the assay results to monitor both the efficiency of B cell depletion and/or the kinetics of B cell repletion in the subject after administration of a therapeutic agent. A kit comprising a BAFF binding reagent and a package insert comprising instructions for determining serum BAFF levels using the BAFF binding reagent and for relating serum BAFF levels to B cell levels in the patient after treatment with a B cell depleting or promoting agent.

DETAILED DESCRIPTION OF THE INVENTION

Figure 1:
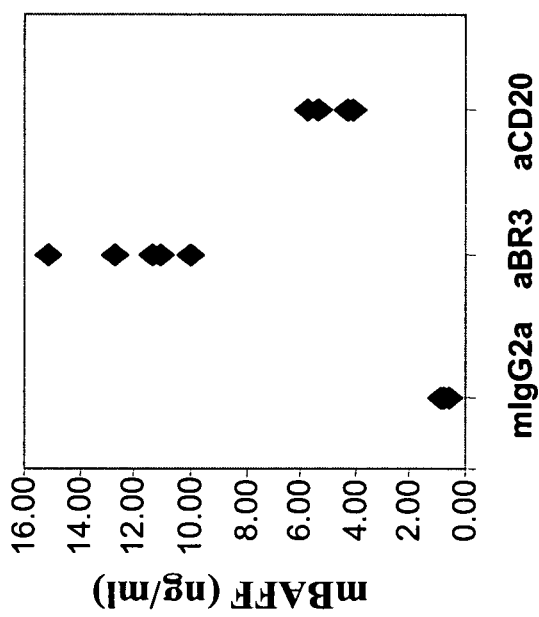
FIG. 1: Serum BAFF is upregulated after B cell depletion in mice.

The clinical response of a subject to therapeutic agents that effect B cells is often measured by evaluating B cell depletion in the subject's blood. However, the results do not fully correlate with levels of B cell depletion observed in the tissue (spleen, lymph node, autoimmune sites like joints, spinal fluid etc). In actuality, clinical response for B cell depletion therapies correlates more with target organ B cell depletion than blood B cell depletion, especially in oncology. Therefore, searching for a better marker to indicate tissue B cell depletion as well as B cell recovery (repletion) is important for optimizing B cell depleting therapies.

The present application discloses that serum BAFF levels are more appropriate markers for reflecting the total B cell load in a subject. As such, evaluation of serum BAFF levels can be used determine B cell levels in subjects, regardless of whether the therapeutic agent targets B cells for inhibition or stimulation of cell growth or survival. Evaluation of serum BAFF levels in patients can be particularly useful in monitoring the efficacy of B cell therapies such as B cell depleting agents or B cell promoting agents. Further, reevaluation of serum BAFF levels during B cell recovery after B cell depletion can be useful for determining retreatment regimes for the B cell depletion agent or when to resume treatment with any other therapeutic agent that modulates the immune system (e.g., DMARDS, T cell depleting agents, immunosuppressive agents, vaccines, etc.). Serum BAFF levels can also be an early marker for determining patients who respond well to B cell therapy versus those who do not and need immediate alternative treatment. Evaluation of serum BAFF levels can be useful in maintenance therapies, wherein the therapy is carried out to maintain the status of a disease after treatment with a therapeutic agent. For example, maintenance therapy can be desired to maintain the remission stage of an autoimmune disease or a cancer.

The term "BAFF" refers to a polypeptide, also known as BLyS, TALL-1, THANK, TNFSF13B, or zTNF4 (e.g., SEQ ID NO:102), that is a member of the TNF ligand superfamily having a role in B cell survival, and homologs, isoforms, fragments and variants thereof having BAFF activity. The term BAFF includes those polypeptides described in Shu et al., J. Leukocyte Biol., 65:680 (1999); GenBank Accession No. AF136293; WO98/18921 published May 7, 1998; EP 869,180 published Oct. 7, 1998; WO98/27114 published Jun. 25, 1998; WO99/12964 published Mar. 18, 1999; WO99/33980 published Jul. 8, 1999; Moore et al., Science, 285:260-263 (1999); Schneider et al., J. Exp. Med., 189: 1747-1756 (1999); Mukhopadhyay et al., J. Biol. Chem., 274:15978-15981 (1999).

A receptor for BAFF according to this invention includes TACI, BR43×2, hTACI(265), BCMA and BR3, and any homologs, isoforms, fragments and variants thereof having BAFF-binding activity and through which BAFF can cell signal. "BR3" is also sometimes referred to as BAFF-R in the art. Examples of BR3, include those described in PCT Publications WO 02/24909 and WO 03/014294 e.g., human BR3 (SEQ ID NO:103), human BR3 extracellular domain (SEQ ID NO:104), and mouse BR3 extracellular domain (SEQ ID NO:105). Examples of TACI, BR43×2, hTACI (265), include those described in Gross et al., (200) Nature 404:995-999, WO 98/39361, WO 00/40716 and WO 01/60397. Examples of BCMA include those described in Laabi et al., (1992) EMBO J. 11(11):3897-3904.

The term "anti-BAFF receptor antibody" or "BAFF receptor binding antibody" refers to any antibody that specifically binds to at least one epitope of a receptor for BAFF. Examples of anti-BR3 antibodies include, but are not limited to, those described in WO 02/24909 (e.g., 9.1 and 2.1) and WO 2006/073941 (e.g., Examples of anti-TACI antibodies include, but are not limited to, those described in WO 2004/011611. Examples of anti-BCMA antibodies include, but are not limited to, those described in Thompson et al., (2001) 293(5537):2108-2111 (e.g., C4.E2.1) and the Vicky-1 antibody (Abcam, Inc., Cambridge, Ma). The anti-BAFF receptor antibodies are preferably monoclonal antibodies. The use of either anti-BAFF receptor antibodies that inhibit the binding of BAFF to a receptor or anti-BAFF receptor antibodies that do not inhibit the binding of BAFF to a receptor as therapeutics are contemplated as in the methods of this invention. Human, humanized, chimerized or otherwise enhanced forms of anti-BAFF receptor antibodies useful for treatment in humans, including enhanced forms of those listed above, are contemplated as therapeutics in the methods of this invention. In one preferred embodiment, the anti-BAFF receptor antibody will bind a BAFF receptor with a Kd of <10 nM. In other preferred embodiments, the binding is at a Kd of <7.5 nM, more preferably <5 nM, even more preferably at between 1-5 nM, most preferably, <1 nM.

The term "BAFF antagonist" as used herein is used in the broadest sense, and includes any molecule that (1) binds a BAFF polypeptide or binds a receptor of BAFF to partially or fully block BAFF interaction with a BAFF receptor, and (2) partially or fully blocks or inhibits BAFF signaling through the BAFF receptor. BAFF antagonists may be proteinaceous (e.g., antibodies, receptor fusion proteins, peptides, peptibodies, dominant negative BAFF mutants) or non proteinaceous molecules (e.g., small organic molecules (≤500 Da)), including siRNA and aptamers, etc. Methods for assessing neutralizing biological activity of BAFF antagonists include, those are known described in the art. Examples of BAFF antagonists include polypeptides comprising a BAFF-binding portion of a BAFF receptor or a BAFF-binding variant thereof (e.g., WO 01/12812, WO 02/24909, WO 00/40716, WO 03/024991), anti-BAFF antibodies (e.g., WO 03/33658), BAFF-binding peptibodies (e.g., WO 02/092620), anti-BAFF-R antibodies (e.g., WO 02/24909) and BAFF-binding peptides (e.g., WO 02/16412). According to one embodiment, the BAFF antagonist is selected from the group consisting of BCMA-Fc (e.g., WO 01/12812), BAFF-R-Fc (e.g., WO 02/24909), TACI-Ig (e.g., WO 00/40716), an anti-BAFF antibody (e.g, WO 03/33658), an anti-BAFF-R antibody (e.g., WO 02/24909), a BAFF-binding peptibodies (e.g., WO 02/092620), a dominant negative BAFF (e.g., WO 04/081043). According a further embodiment, anti-BAFF antibodies and anti-BAFF receptor antibodies are human, humanized, chimerized or otherwise enhanced for treatment in humans. Examples of an anti-BAFF antibody include belimumab and BAFF-binding antibodies described in WO02/02641 and WO 03/55979. Examples of BAFF-binding peptide-Fc fusion protein include BAFF-binding fusion proteins described in WO 02/24909.

A "B cell surface marker" or "B cell surface antigen" herein is an antigen expressed on the surface of a B cell which can be targeted with an antagonist which binds thereto. Exemplary B cell surface markers include, but are not limited to, CD10, CD19, CD20, CD21, CD22, CD23, CD24, CD37, CD40, CD52, D53, CD72, CD73, CD74, CDw75, CDw76, CD77, CDw78, CD79a, CD79b, CD80, CD81, CD82, CD83, CDw84, CD85, CD86, CD180 (RP105), FcRH2 (IRTA4), CD79A, C79B, CR2, CCR6, CD72, P2x5, HLA-DOB, CXCR5 (BLR1), FCER2, BR3 (aka BAFF-R), TACI, BTLA, NAG14 (aka LRRC4), SLGC16270 (ala LOC283663), FcRH1 (IRTA5), FcRH5 (IRTA2), ATWD578 (aka MGC15619), FcRH3 (IRTA3), FcRH4 (IRTA1), FcRH6 (aka LOC343413) and BCMA (aka TNFRSF17), HLA-DO, HLA-Dr10 and MHC ClassII.

In one preferred embodiment, the B cell surface marker of particular interest is expressed on B cells compared to other non-B cell tissues of a mammal and may be expressed on both precursor B cells and mature B cells. Examples of preferred B cell surface markers include, but are not limited to, CD19, CD20 and CD22.

The "CD19" antigen refers to an antigen identified, for example, by the HD237-CD19 or B4 antibody (Kiesel et al. Leukemia Research II, 12: 1119 (1987)). CD19 is found on Pro-B, pre-B, immature and mature, activated and memory B cells, up to a point just prior to terminal differentiation into plasma cells. Neither CD19 nor CD20 is expressed on hematopoietic stem cell or plasma cell. Binding of an antagonist to CD19 may cause internalization of the CD19 antigen. The amino acid sequence of human CD19 is shown in The Leukocyte Antigen Facts Book, Barclay et al. supra, page 180, and also EMBL Genbank accession no. M28170 and Swissprot P11836.

The "CD22" antigen, also known as BL-CAM or Lyb8, is a type 1 integral membrane glycoprotein with molecular weight of about 130 (reduced) to 140 kD (unreduced). It is expressed in both the cytoplasm and cell membrane of B-lymphocytes. CD22 antigen appears early in B-cell lymphocyte differentiation at approximately the same stage as the CD19 antigen. Unlike other B-cell markers, CD22 membrane expression is limited to the late differentiation stages comprised between mature B cells (CD22+) and plasma cells (CD22−). The CD22 antigen is described, for example, in Wilson et al. J. Exp. Med. 173:137 (1991) and Wilson et al. J. Immunol. 150:5013 (1993).

The "CD20" antigen is a non-glycosylated, transmembrane phosphoprotein with a molecular weight of approximately 35 kD that is found on the surface of greater than 90% of B cells from peripheral blood or lymphoid organs. CD20 is expressed during early pre-B cell development and remains until plasma cell differentiation; it is not found on human stem cells, lymphoid progenitor cells or normal plasma cells. CD20 is present on both normal B cells as well as malignant B cells. Other names for CD20 in the literature include "B-lymphocyte-restricted differentiation antigen" and "Bp35". The CD20 antigen is described in, for example, Clark and Ledbetter, Adv. Can. Res. 52:81-149 (1989) and Valentine et al. J. Biol. Chem. 264(19):11282-11287 (1989).

CD20 binding antibody and anti-CD20 antibody are used interchangeably herein and encompass all antibodies that bind CD20 with sufficient affinity such that the antibody is useful as a therapeutic agent in targeting a cell expressing the antigen, and do not significantly cross-react with other proteins such as a negative control protein in the assays described below. Bispecific antibodies wherein one arm of the antibody binds CD20 are also contemplated. Also encompassed by this definition of CD20 binding antibody are functional fragments of the preceding antibodies. The CD20 binding antibody will bind CD20 with a Kd of <10 nM. In preferred embodiments, the binding is at a Kd of <7.5 nM, more preferably <5 nM, even more preferably at between 1-5 nM, most preferably, <1 nM.

Examples of antibodies which bind the CD20 antigen include: "C2B8" which is now called "Rituximab" ("RITUXAN®") (U.S. Pat. No. 5,736,137, expressly incorporated herein by reference); the yttrium-[90]-labeled 2B8 murine antibody designated "Y2B8" or "Ibritumomab Tiuxetan" ZEVALIN® (U.S. Pat. No. 5,736,137, expressly incorporated herein by reference); murine IgG2a "B1," also called "Tositumomab," (Beckman Coulter) optionally labeled with $^{131}$I to generate the "131I-B1" antibody (iodine I131 tositumomab, BEXXAR™) (U.S. Pat. No. 5,595,721, expressly incorporated herein by reference); murine monoclonal antibody "1F5" (Press et al. Blood 69(2):584-591 (1987) and variants thereof including "framework patched" or humanized 1F5 (WO03/002607, Leung, S.); ATCC deposit HB-96450); murine 2H7 and chimeric 2H7 antibody (U.S. Pat. No. 5,677,180, expressly incorporated herein by reference); humanized 2H7; huMax-CD20 (Genmab, Denmark); AME-133 (Applied Molecular Evolution); A20 antibody or variants thereof such as chimeric or humanized A20 antibody (cA20, hA20, respectively) (US 2003/0219433, Immunomedics); and monoclonal antibodies L27, G28-2, 93-1B3, B-C1 or NU-B2 available from the International Leukocyte Typing Workshop (Valentine et al., In: Leukocyte Typing III (McMichael, Ed., p. 440, Oxford University Press (1987)).

The terms "rituximab" or "RITUXAN®" herein refer to the genetically engineered chimeric murine/human monoclonal antibody directed against the CD20 antigen and designated "C2B8" in U.S. Pat. No. 5,736,137 expressly incorporated herein by reference, including fragments thereof which retain the ability to bind CD20.

In a specific embodiment, the anti-CD20 antibodies bind human and primate CD20. In specific embodiments, the antibodies that bind CD20 are humanized or chimeric. CD20 binding antibodies include rituximab (RITUXAN®), m2H7 (murine 2H7), hu2H7 (humanized 2H7) and all its functional variants, including without limitation, hu2H7.v16 (v stands for version), v31, v73, v75, as well as fucose deficient variants, and other 2H7 variants described in WO2004/056312. Unless indicated, the sequences disclosed herein of the humanized 2H7v.16 and variants thereof are of the mature polypeptide, i.e., without the leader sequence.

Patents and patent publications concerning CD20 antibodies include U.S. Pat. Nos. 5,776,456, 5,736,137, 5,843,439, 6,399,061, and 6,682,734, as well as US patent appln Nos. US 2002/0197255A1, US 2003/0021781A1, US 2003/0082172 A1, US 2003/0095963 A1, US 2003/0147885 A1 (Anderson et al.); U.S. Pat. No. 6,455,043B1 and WO00/09160 (Grillo-Lopez, A.); WO00/27428 (Grillo-Lopez and White); WO00/27433 (Grillo-Lopez and Leonard); WO00/44788 (Braslawsky et al.); WO01/10462 (Rastetter, W.); WO01/10461 (Rastetter and White); WO01/10460 (White and Grillo-Lopez); US2001/0018041A1, US2003/0180292A1, WO01/34194 (Hanna and Hariharan); U.S. appln No. US2002/0006404 and WO02/04021 (Hanna and Hariharan); U.S. appln No. US2002/0012665 A1 and WO01/74388 (Hanna, N.); U.S. appln No. US 2002/0058029 A1 (Hanna, N.); U.S. appln No. US 2003/0103971 A1 (Hariharan and Hanna); U.S. appln No. US2002/0009444A1, and WO01/80884 (Grillo-Lopez, A.); WO01/97858 (White, C.); U.S. appln No. US2002/0128488A1 and WO02/34790 (Reff, M.); WO02/060955 (Braslawsky et al.); WO2/096948 (Braslawsky et al.); WO02/079255 (Reff and Davies); U.S. Pat. No. 6,171,586B1, and WO98/56418 (Lam et al.); WO98/58964 (Raju, S.); WO99/22764 (Raju, S.); WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.); WO00/42072 (Presta, L.); WO00/67796 (Curd et al.); WO01/03734 (Grillo-Lopez et al.); U.S. appln No. US 2002/0004587A1 and WO01/77342 (Miller and Presta); U.S. appln No. US2002/0197256 (Grewal, I.); U.S. Appln No. US 2003/0157108 A1 (Presta, L.); U.S. Pat. Nos. 6,565,827B1, 6,090,365B1, 6,287,537B1, 6,015,542, 5,843,398, and 5,595,721, (Kaminski et al.); U.S. Pat. Nos. 5,500,362, 5,677,180, 5,721,108, 6,120,767, 6,652,852B1 (Robinson et al.); U.S. Pat. No. 6,410,391B1 (Raubitschek et al.); U.S. Pat. No. 6,224,866B1 and WO00/20864 (Barbera-Guillem, E.); WO01/13945 (Barbera-Guillem, E.); WO00/67795 (Goldenberg); U.S. Appl No. US 2003/0133930 A1 and WO00/74718 (Goldenberg and Hansen); WO00/76542 (Golay et al.); WO01/72333 (Wolin and Rosenblatt); U.S. Pat. No. 6,368,596B1 (Ghetie et al.); U.S. Pat. No. 6,306,393 and U.S. Appln No. US2002/0041847 A1, (Goldenberg, D.); U.S. Appln No. US2003/0026801A1 (Weiner and Hartmann); WO02/102312 (Engleman, E.); U.S. Patent Application No. 2003/0068664 (Albitar et al.); WO03/002607 (Leung, S.); WO 03/049694, US2002/0009427A1, and US 2003/0185796 A1 (Wolin et al.); WO03/061694 (Sing and Siegall); US 2003/0219818 A1 (Bohen et al.); US 2003/0219433 A1 and WO 03/068821 (Hansen et al.); US2003/0219818A1 (Bohen et al.); US2002/0136719A1 (Shenoy et al.); WO2004/032828 (Wahl et al.), each of which is expressly incorporated herein by reference. See, also, U.S. Pat. No. 5,849,898 and EP appln no. 330,191 (Seed et al.); U.S. Pat. No. 4,861,579 and EP332,865A2 (Meyer and Weiss); U.S. Pat. No. 4,861,579 (Meyer et al.); WO95/03770 (Bhat et al.); US 2003/0219433 A1 (Hansen et al.).

The CD20 antibodies can be naked antibody or conjugated to a cytotoxic compound such as a radioisotope, or a toxin. Such antibodies include the antibody Zevalin™ which is linked to the radioisotope, Yttrium-90 (IDEC Pharmaceuticals, San Diego, Calif.), and Bexxar™ which is conjugated to 1-131 (Corixa, Wash.). The humanized 2H7 variants include those that have amino acid substitutions in the FR and affinity maturation variants with changes in the grafted CDRs. The substituted amino acids in the CDR or FR are not limited to those present in the donor or acceptor antibody. In other embodiments, the anti-CD20 antibodies of the invention further comprise changes in amino acid residues in the Fc region that lead to improved effector function including enhanced CDC and/or ADCC function and B-cell killing (also referred to herein as B-cell depletion). In particular, three mutations have been identified for improving CDC and ADCC activity: S298A/E333A/K334A (also referred to herein as a triple Ala mutant or variant; numbering in the Fc region is according to the EU numbering system; Kabat et al., supra) as described (Idusogie et al., supra (2001); Shields et al., supra).

Other anti-CD20 antibodies of the invention include those having specific changes that improve stability. In one embodiment, the chimeric anti-CD20 antibody has murine V regions and human C region. One such specific chimeric anti-CD20 antibody is Rituxan® (Rituximab®; Genentech, Inc.). Rituximab and hu2H7 can mediate lysis of B-cells through both complement-dependent cytotoxicity (CDC) and antibody-dependent cellular cytotoxicity (ADCC). Antibody variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

"Therapeutic agents" refers to agents that are useful in alleviating a disease or the symptoms of a disease. Therapeutic agents can be proteinaceous (e.g., antibodies, receptor fusion proteins, peptides, peptibodies, immunoadhesins) or non proteinaceous molecules (e.g., small organic molecules ($\leq$500 Da)), including siRNA and aptamers, etc.

"B cell promoting agents" refers to agents that stimulate B cell proliferation or survival. Examples of B cell promoting agents include cytokines and antibodies that stimulate B cell proliferation or survival. Examples of cytokines that are B cell promoting agents include, but are not limited to, IL-2, IL-4, IL-5, IL-6, IL-10, IL-14, IL-15 and IL-21.

As used herein, "B cell depletion" refers to a reduction in peripheral blood B cell levels in an animal or human after drug or antibody treatment, as compared to the level before treatment. B cell levels are measurable using well known assays such as by getting a complete blood count or by FACS analysis for known B cell markers (e.g., B220 or CD19 in mice, or CD19 and CD20 in humans). B cell depletion can be partial or complete. In one embodiment, the depletion of CD20 expressing peripheral B cells is at least 25%. In another embodiment, the depletion of CD20 expressing peripheral B cells is at least 30%, 40%, 50%, 60%, 70%, 80% or 90%. Not to be limited by any one mechanism, possible mechanisms of B cell depletion include ADCC, CDC, apoptosis, modulation of calcium flux or a combination of two or more of the preceding.

"B cell depletion agents" or "B cell depleting agents" refers to agents that reduce peripheral B cells by at least 25%. In another embodiment, the depletion of peripheral B cells is at least 30%, 40%, 50%, 60%, 70%, 80% or 90%. In one preferred embodiment, the B cell depletion agent specifically binds to a white blood cell and not other cells types. In another embodiment, the B cell depletion specifically binds to a B cell and not other cell types. In one embodiment, the B cell depletion agent is an antibody. In one preferred embodiment, the antibody is a monoclonal antibody. In another embodiment, the antibody is conjugated to a chemotherapeutic agent or a cytotoxic agent. Specific examples of B cell depletion agents include, but are not limited to, the aforementioned anti-CD20 antibodies, Alemtuzumab (anti-CD52 antibody), and Epratuzumab or CMC-544 (Wyeth) (anti-CD22 antibodies) or anti-BR3 antibodies described herein.

"B cell recovery phase" is the stage of B cell repletion in a subject after treatment with a therapeutic agent has reduced B cells levels in the subject to its lowest levels. "Tissue B cell recovery phase" is the stage of B cell repletion in the tissue in a subject after treatment with a therapeutic agent has reduced tissue B cells levels in the subject to its lowest levels. "Peripheral B cell recovery phase" is the stage of B cell repletion in the peripheral blood in a subject after treatment with a therapeutic agent has reduced peripheral blood B cells levels in the subject to its lowest levels.

"Maximum B cell depletion phase" is the stage of maximum B cell depletion in a subject after treatment with a therapeutic agent that reduces B cells levels.

"T cell depletion agents" refers to agents that reduce T cells by at least 25% in the peripheral blood. In another embodiment, the depletion of peripheral T cells is at least 30%, 40%, 50%, 60%, 70%, 80% or 90%. In one preferred embodiment, the T cell depletion agent specifically binds to a T cell and not other cells types. In one embodiment, the T cell depletion agent is an antibody or a chemical compound. In one preferred embodiment, the antibody is a monoclonal antibody. In another embodiment, the antibody is conjugated to a chemotherapeutic agent or a cytotoxic agent.

"DMARDS" or "disease-modifying anti-rheumatic drugs" are drugs that slow down the biological processes that are the driving force behind persistent inflammation. DMARDS include, but are not limited to, methotrexate, hydroxycloroquine, sulfasalazine, methotrexate, leflunomide, etanercept, infliximab, azathioprine, D-penicillamine, Gold (oral), Gold (intramuscular), minocycline, cyclosporine, Staphylococcal protein A immunoadsorption.

"Immunosuppressive agent" as used herein refers to substances that act to suppress or mask the immune system of a patient. Such agents would include substances that suppress cytokine production, down regulate or suppress self-antigen expression, or mask the MHC antigens. Examples of such agents include steroids such as glucocorticosteroids, e.g., prednisone, methylprednisolone, and dexamethasone; 2-amino-6-aryl-5-substituted pyrimidines (see U.S. Pat. No. 4,665,077), azathioprine (or cyclophosphamide, if there is an adverse reaction to azathioprine); bromocryptine; glutaraldehyde (which masks the MHC antigens, as described in U.S. Pat. No. 4,120,649); anti-idiotypic antibodies for MHC antigens and MHC fragments; cyclosporin A; cytokine or cytokine receptor antagonists including anti-interferon-γ, -β, or -α antibodies; anti-tumor necrosis factor-α antibodies; anti-tumor necrosis factor-β antibodies; anti-interleukin-2 antibodies and anti-IL-2 receptor antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; TGF-β; streptodornase; RNA or DNA from the host; FK506; RS-61443; deoxyspergualin; rapamycin; T-cell receptor (U.S. Pat. No. 5,114,721); T-cell receptor fragments (Offner et al., *Science* 251:430-432 (1991); WO 90/11294; and WO 91/01133); and T cell receptor antibodies (EP 340,109) such as T10B9.

The term "immunological disorder" refers to disorders and conditions in which an immune response is aberrant. The aberrant response can be due to (a) abnormal proliferation, maturation, survival, differentiation, or function of immune cells such as, for example, T and/or B cells. Examples of immunological disorders include, but are not limited to, hyperproliferative immune disorders, antibody mediated pathologies, autoimmune disorders, B cell disorders including plasma cell disorders, B cell lymphoproliferative disorders such as B cell neoplasias and B cell hyperplasias, antibody mediated pathologies, transplant rejection, allergies. According to one embodiment, the immunological disorder exhibits, in part, elevated serum BAFF levels or decreased serum BAFF levels compared to a control (e.g., compared to serum BAFF levels of a normal, healthy subject).

An "immunodeficiency disease" is a disorder or condition where the immune response is reduced (e.g., severe combined immunodeficiency (SCID)-X linked, SCID-autosomal, adenosine deaminase deficiency (ADA deficiency), X-linked agammaglobulinemia (XLA). Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia telangiectasia (cerebellar ataxia, oculocutaneous telangiectasia and immunodeficiency), short limbed dwarfism, X-linked lymphoproliferative syndrome (XLP), Nezelof syndrome-cumbined immunodeficiency with Igs, purine nucleotide phosphorylase deficiency (PNP), MHC Class II deficiency (Bare Lymphocyte Syndrome) and severe combined immunodeficiency), or conditions associated with an immunodeficiency, Janus Associated Kinase 3 (JAK3) deficiency, DiGeorge's syndrome (isolated T cell deficiency) and Associated syndromes e.g., Down syndrome, chronic mucocutaneous candidiasis, hyper-IgE syndrome, chronic granulomatous disease, partial albinism and WHIM syndrome (warts, hypogammaglobulinemia, infection, and myelokathexis [retention of leukocytes in a hypercellular marrow]).

An "autoimmune disease" herein is a disease or disorder arising from and directed against an individual's own tissues or organs or a co-segregate or manifestation thereof or resulting condition therefrom. In many of these autoimmune and inflammatory disorders, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues. Without being limited to any one theory regarding B-cell mediated autoimmune disease, it is believed that B cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis. Each of these pathways may participate to different degrees in the pathology of autoimmune diseases.

"Autoimmune disease" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.). Preferred such diseases include autoimmune rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Specific examples of other autoimmune diseases as defined herein, which in some cases encompass those listed above, include, but are not limited to, arthritis (acute and chronic, rheumatoid arthritis including juvenile-onset rheumatoid arthritis and stages such as rheumatoid synovitis, gout or gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylosing spondylitis/rheumatoid spondylitis), autoimmune lymphoproliferative disease, inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, hives, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, gastrointestinal inflammation, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, graft-versus-host disease, angioedema such as hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN (RPGN), proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, food allergies, drug allergies, insect allergies, rare allergic disorders such as mastocytosis, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, SLE, such as cutaneous SLE or subacute cutaneous SLE, neonatal lupus syndrome (NLE), and lupus erythematosus disseminatus, juvenile onset (Type I) diabetes mellitus, including pediatric IDDM, adult onset diabetes mellitus (Type II diabetes), autoimmune diabetes, idiopathic diabetes insipidus, diabetic retinopathy, diabetic nephropathy, diabetic colitis, diabetic large-artery disorder, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia(s), cytopenias such as pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, antiglomerular basement membrane disease, anti-phospholipid antibody syndrome, motoneuritis, allergic neuritis, Behçet's disease/syndrome, Castleman's syndrome, Goodpasture's syndrome, Reynaud's syndrome, Sjögren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury due to an autoimmune condition, preeclampsia, an immune complex disorder such as immune complex nephritis, antibody-mediated nephritis, neuroinflammatory disorders, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia including, for example, idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes, for example, type I (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, pneumonitis such as lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia such as mixed cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, fibrosing mediastinitis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis (systemic inflammatory response syndrome (SIRS)), endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, conjunctivitis, such as vernal catarrh, keratoconjunctivitis sicca, and epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders (cerebral vascular insufficiency) such as arteriosclerotic encephalopathy and arteriosclerotic retinopathy, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, lymphofollicular thymitis, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndromes, including polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, allergic sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, spondyloarthropathies, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism such as chronic arthrorheumatism, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis.

Examples of hyperproliferative immune disorders include, but are not limited to, non-Hodgkin's lymphoma (NHL), chronic lymphocytic leukemia (CLL), acute lymphocytic leukemia (ALL), mantle cell lymphoma, marginal zone related tumors, follicular lymphoma (FL), large cell lymphoma such as diffuse large B-cell lymphoma, Burkitt's lymphoma, plasma cell disorders such as multiple myeloma.

Examples of antibody mediated pathologies include, but are not limited to, ITP, myasthenia gravis, autoimmune hemolytic anemia (erythrocyte autoantibodies), Hashimoto's thyroiditis (thyroid autoantibodies), myasthenia gravis (acetylcholine receptor autoantibodies), Grave's disease characterized by diffuse goiter and hyperthyroidism (thyrotropin receptor autoantibodies) and Goodpasture's syndrome comprising anti-GBM autoantibodies.

B cell neoplasms include Hodgkin's disease including lymphocyte predominant Hodgkin's disease (LPHD); non-Hodgkin's lymphoma (NHL); follicular center cell (FCC) lymphomas; acute lymphocytic leukemia (ALL); chronic lymphocytic leukemia (CLL); and Hairy cell leukemia. The non-Hodgkins lymphoma include low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, plasmacytoid lymphocytic lymphoma, mantle cell lymphoma, AIDS-related lymphoma and Waldenstrom's macroglobulinemia. Treatment of relapses of these cancers are also contemplated. LPHD is a type of Hodgkin's disease that tends to relapse frequently despite radiation or chemotherapy treatment. CLL is one of four major types of leukemia. A cancer of mature B-cells called lymphocytes, CLL is manifested by progressive accumulation of cells in blood, bone marrow and lymphatic tissues. Indolent lymphoma is a slow-growing, incurable disease in which the average patient survives between six and 10 years following numerous periods of remission and relapse.

The term "non-Hodgkin's lymphoma" or "NHL", as used herein, refers to a cancer of the lymphatic system other than Hodgkin's lymphomas. Hodgkin's lymphomas can generally be distinguished from non-Hodgkin's lymphomas by the presence of Reed-Stemberg cells in Hodgkin's lymphomas and the absence of said cells in non-Hodgkin's lymphomas. Examples of non-Hodgkin's lymphomas encompassed by the term as used herein include any that would be identified as such by one skilled in the art (e.g., an oncologist or pathologist) in accordance with classification schemes known in the art, such as the Revised European-American Lymphoma (REAL) scheme as described in Color Atlas of Clinical Hematology, Third Edition; A. Victor Hoffbrand and John E. Pettit (eds.) (Harcourt Publishers Limited 2000) (see, in particular FIG. 11.57, 11.58 and/or 11.59). More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B cell chronic lymphacytic leukemia and/or prolymphocytic leukemia and/or small lymphocytic lymphoma, B-cell prolymphocytic lymphoma, immunocytoma and/or lymphoplasmacytic lymphoma, marginal zone B cell lymphoma, splenic marginal zone lymphoma, extranodal marginal zone—MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) T-cell lymphoblastic leukemia and/or lymphoma, adult T-cell lymphoma and/or leukemia, T cell chronic lymphocytic leukemia and/or prolymphacytic leukemia, large granular lymphocytic leukemia, mycosis fungoides and/or Sezary syndrome, extranodal natural killer/T-cell (nasal type) lymphoma, enteropathy type T-cell lymphoma, hepatosplenic T-cell lymphoma, subcutaneous panniculitis like T-cell lymphoma, skin (cutaneous) lymphomas, anaplastic large cell lymphoma, angiocentric lymphoma, intestinal T cell lymphoma, peripheral T-cell (not otherwise specified) lymphoma and angioimmunoblastic T-cell lymphoma.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; multiple myeloma and post-transplant lymphoproliferative disorder (PTLD).

As used herein, the term "immunoadhesin" designates molecules which combine the binding specificity of a heterologous protein (an "adhesin") with the effector functions of immunoglobulin constant domains. Structurally, the immunoadhesins comprise a fusion of an amino acid sequence with a desired binding specificity, which amino acid sequence is other than the antigen recognition and binding site of an antibody (i.e., is "heterologous"), and an immunoglobulin constant domain sequence (e.g., $CH_2$ and/or $CH_3$ sequence of an IgG). Exemplary adhesin sequences include contiguous amino acid sequences that comprise a portion of a receptor or a ligand that binds to a protein of interest. Adhesin sequences can also be sequences that bind a protein of interest, but are not receptor or ligand sequences (e.g., adhesin sequences in peptibodies). Such polypeptide sequences can be selected or identified by various methods, include phage display techniques and high throughput sorting methods. The immunoglobulin constant domain sequence in the immunoadhesin can be obtained from any immunoglobulin, such as IgG-1, IgG-2, IgG-3, or IgG-4 subtypes, IgA (including IgA-1 and IgA-2), IgE, IgD, or IgM.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of an antibody or immunoadhesin, or by recombinantly engineering the Fc region to remove the K447. Accordingly, a composition of antibodies or immunoadhesins, e.g., as recited herein, may comprise populations with all K447 residues removed, populations with no K447 residues removed, and populations having a mixture of antibodies with and without the K447 residue.

Unless indicated otherwise, herein the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody.

The term "antibody" is used in the broadest sense and specifically covers, for example, single monoclonal antibodies (including agonist, antagonist, and neutralizing antibodies), antibody compositions with polyepitopic specificity, polyclonal antibodies, single chain anti-antibodies, and fragments of antibodies (see below) as long as they specifically bind a native polypeptide and/or exhibit a biological activity or immunological activity of this invention. According to one embodiment, the antibody binds to an oligomeric form of a target protein, e.g., a trimeric form. According to another embodiment, the antibody specifically binds to a protein, which binding can be inhibited by a monoclonal antibody of this invention (e.g., a deposited antibody of this invention, etc.). The phrase "functional fragment or analog" of an antibody is a compound having a qualitative biological activity in common with an antibody to which it is being referred. For example, a functional fragment or analog of an antibody of this invention can be one which can specifically bind to a B cell surface antigen. The term "immunoglobulin" (Ig) is used interchangeably with "antibody" herein.

An "isolated antibody" is one which has been identified and separated and/or recovered from a component of its natural environment. Contaminant components of its natural environment are materials which would interfere with diagnostic or therapeutic uses for the antibody, and can include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a *-sheet configuration, connected by three hypervariable regions, which form loops connecting, and in some cases forming part of, the *-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature*, 256:495 (1975); Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681, (Elsevier, N.Y., 1981)), recombinant DNA methods (see, e.g., U.S. Pat. No. 4,816,567), phage display technologies (see, e.g., Clackson et al., *Nature*, 352:624-628 (1991); Marks et al., *J. Mol. Biol.*, 222:581-597 (1991); Sidhu et al., *J. Mol. Biol.* 338(2):299-310 (2004); Lee et al., *J. Mol. Biol.* 340(5): 1073-1093 (2004); Fellouse, *Proc. Nat. Acad. Sci. USA* 101(34):12467-12472 (2004); and Lee et al. *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA*, 90:2551 (1993); Jakobovits et al., *Nature*, 362:255-258 (1993); Bruggemann et al., *Year in Immuno.*, 7:33 (1993); U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569, 825; 5,625,126; 5,633,425; and 5,661,016; Marks et al., *Bio/Technology*, 10: 779-783 (1992); Lonberg et al., *Nature*, 368: 856-859 (1994); Morrison, *Nature*, 368: 812-813 (1994); Fishwild et al., *Nature Biotechnology*, 14: 845-851 (1996); Neuberger, *Nature Biotechnology*, 14: 826 (1996); and Lonberg and Huszar, *Intern. Rev. Immunol.*, 13: 65-93 (1995).

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains can be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments or other techniques.

The expression "linear antibodies" generally refers to the antibodies described in Zapata et al., Protein Eng., 8(10): 1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by di sulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "cross-over" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

A "species-dependent antibody" is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

An agent "which binds" an antigen of interest is one that binds the antigen with sufficient affinity such that a polypeptide, antibody, antagonist or composition is useful as a diagnostic and/or therapeutic agent in targeting a cell or tissue expressing the antigen, and does not significantly cross-react with other proteins (unless otherwise specified). In such embodiments, the extent of binding of the agent to a "non-target" protein will be less than about 10% of the binding of the polypeptide, antibody, antagonist or composition to its particular target protein, which can be determined by fluorescence activated cell sorting (FACS) analysis or radioimmunoprecipitation (RIA). With regard to the binding of a polypeptide agent to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al. (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells can be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), can be performed.

A subject to be treated according to this invention is a mammal. The mammal could be, for example, a primate (e.g., a human), a rodent (e.g., a rat or a mouse), or a mammal of another species. In each one of the above methods, the mammal may be one that suffers from an immunological disorder.

A mammal "in need" of treatment can include, but are not limited to, mammals that have immunological disorders, mammals that have had immunological disorders, mammals with symptoms of immunological disorders or mammals that have elevated or decreased BAFF levels.

An "effective amount" of an agent as disclosed herein is an amount sufficient to carry out a specifically stated purpose. An "effective amount" can be determined empirically and by known methods relating to the stated purpose.

The term "therapeutically effective amount" refers to an amount of a therapeutic agent of this invention effective to "treat" a disease or disorder in a mammal (aka patient). In one instance, the therapeutically effective amount may be a growth inhibitory amount or a cytotoxic amount for one or several cell types. In autoimmune diseases, a therapeutically effective amount may be the amount that alleviates one or more symptoms of the disease or the amount necessary to keep a disease in remission. In the case of cancer, the therapeutically effective amount of the drug active for any one of the following: reducing the number of cancer cells; reducing the tumor size; inhibiting (i.e., slow to some extent and preferably stop) cancer cell infiltration into peripheral organs; inhibiting (i.e., slow to some extent and preferably stop) tumor metastasis; inhibiting, to some extent, tumor growth; and/or relieve to some extent one or more of the symptoms associated with the cancer. To the extent the drug can prevent growth and/or kill existing cancer cells, it can be cytostatic and/or cytotoxic. A "treatment" or a "therapeutically effective amount" refers to a course of administration of the therapeutic agent, which course may include several dosings spread over a period of time to achieve a desired effect.

A "growth inhibitory amount" of a therapeutic agent an amount capable of inhibiting the growth of a cell, especially tumor, e.g., cancer cell, either in vitro or in vivo. A "growth inhibitory amount" of a polypeptide, antibody, antagonist or composition of this invention can be determined empirically or for example, by methods known in the art.

A "cytotoxic amount" of a therapeutic agent is an amount capable of causing the destruction of a cell, especially tumor, e.g., cancer cell, either in vitro or in vivo. A "cytotoxic amount" of therapeutic agent can be determined empirically or, for example, by methods known in the art.

The term "determining" is intended to include any method for evaluating the amounts of a substance. In general, the particular technique used for detection is not critical for practice of the invention.

Examples of comparative controls include, but are not limited to, sera from normal healthy patients, non-malignant tissue and pre-treatment or post-treatment samples. In one embodiment, BAFF polypeptide levels in sera from mammals with immunological disorders are compared to sera from normal mammals.

Production of Antibodies (i) Polyclonal Antibodies

Polyclonal antibodies can be raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. For example, the animal can be boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that may contain one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In one embodiment, the myeloma cells are those that fuse efficiently, support stable high-level production of antibody by the selected antibody-producing cells, and are sensitive to a medium such as HAT medium. Among these, preferred myeloma cell lines include murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. In one embodiment, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a one source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130:151-188 (1992).

In a further embodiment, antibodies or antibody fragments can be isolated from antibody phage libraries generated using the techniques described in e.g., McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Examples of methods for humanizing non-human antibodies have been described. Generally, a humanized antibody has one or more amino acid residues in it from a source which is non-human. These non-human amino acid residues are often referred to as "import" residues, which are typically taken from an "import" variable domain (e.g., Jones et al., *Nature*, 321:522-525 (1986); Riechmann et al., *Nature*, 332:323-327 (1988); Verhoeyen et al., *Science*, 239:1534-1536 (1988)). Often, humanized antibodies are human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is often important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(iv) Human Antibodies

As an alternative to humanization, human antibodies can be generated. For example, it is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and U.S. Pat. Nos. 5,591,669, 5,589,369 and 5,545,807.

Alternatively, phage display technology (e.g., McCafferty et al., *Nature* 348:552-553 (1990)) can be used to produce human antibodies and antibody fragments in vitro, from immunoglobulin variable (V) domain gene repertoires from unimmunized donors. In one embodiment, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

Human antibodies may also be generated by in vitro activated B cells (see U.S. Pat. Nos. 5,567,610 and 5,229,275).

(v) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the B cell surface marker. Other such antibodies may bind a first B cell marker and further bind a second B cell surface marker. Alternatively, an anti-B cell marker binding arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the B cell. Bispecific antibodies may also be used to localize cytotoxic agents to the B cell. These antibodies possess a B cell marker-binding arm and an arm which binds the cytotoxic agent (e.g. saporin, anti-interferon-, vinca alkaloid, ricin A chain, methotrexate or radioactive isotope hapten). Bispecific antibodies can be prepared as full length antibodies or antibody fragments (e.g. F(ab')$_2$ bispecific antibodies).

Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion can be with an immunoglobulin heavy chain constant domain, comprising at least part of the hinge, CH2, and CH3 regions. According to one embodiment, the first heavy-chain constant region (CH1) containing the site necessary for light chain binding is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach described in U.S. Pat. No. 5,731,168, the interface between a pair of antibody molecules can be engineered to maximize the percentage of heterodimers which are recovered from recombinant cell culture. The interface can comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (V$_H$) connected to a light-chain variable domain (V$_L$) by a linker which is too short to allow pairing between the two domains on the same chain. Accordingly, the V$_H$ and V$_L$ domains of one fragment are forced to pair with the complementary V$_L$ and V$_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Amino acid sequence modification(s) of protein or peptide antagonists and antibodies described herein are contemplated. For example, it may be desirable to improve the binding affinity and/or other biological properties of the original molecule (e.g., B cell depleting agent, etc.). Amino acid sequence variants of the antagonist are prepared by introducing appropriate nucleotide changes into the antagonist nucleic acid, or by peptide synthesis. Such modifications include, for example, deletions from, and/or insertions into and/or substitutions of, residues within the amino acid sequences of the antagonist. Any combination of deletion, insertion, and substitution is made to arrive at the final construct, provided that the final construct possesses the desired characteristics. The amino acid changes also may alter post-translational processes of the antagonist, such as changing the number or position of glycosylation sites.

A useful method for identification of certain residues or regions that are preferred locations for mutagenesis is called "alanine scanning mutagenesis" as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most often preferably alanine or polyalanine) to affect the interacantation of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an polypeptides with an N-terminal methionyl residue or polypeptides fused to a cytotoxic polypeptide. Other insertional variants include the fusion of an enzyme or a polypeptide which increases the serum half-life of a molecule to the N- or C-terminus of the original molecule.

Another type of variant is an amino acid substitution variant. These variants have at least one amino acid residue in the original molecule replaced by different residue. The sites of greatest interest for substitutional mutagenesis of antibody antagonists include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |

TABLE 1-continued

| Original Residue | Exemplary Substitutions | Preferred Substitutions |
|---|---|---|
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the original molecule are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.
Non-conservative substitutions will entail exchanging a member of one of these classes for another class.

Any cysteine residue not involved in maintaining the proper conformation of the original molecule also may be substituted, generally with serine, to improve the oxidative stability of the molecule and prevent aberrant crosslinking. Conversely, cysteine bond(s) may be added to the original molecule to improve its stability (particularly where the original molecule is an antibody fragment such as an Fv fragment).

One preferred type of substitutional variant involves substituting one or more hypervariable region residues of a parent antibody. Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant alters the original glycosylation pattern of the antagonist. By altering is meant deleting one or more carbohydrate moieties found in the original molecule, and/or adding one or more glycosylation sites that are not present in the original molecule.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the original molecule is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original molecule (for O-linked glycosylation sites).

Nucleic acid molecules encoding amino acid sequence variants of the original molecule can be prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the original molecule.

It may be desirable to modify an antibody of the invention with respect to effector function, e.g. so as to enhance antigen-dependent cell-mediated cyotoxicity (ADCC) and/or complement dependent cytotoxicity (CDC) of the original molecule. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

To increase the serum half life of the original molecule, one may incorporate a salvage receptor binding epitope into the original molecule (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Dosing

Depending on the indication to be treated and factors relevant to the dosing that a physician of skill in the field would be familiar with, the therapeutic agents of the invention will typically be administered at a dosage that is efficacious for the treatment of that indication while minimizing toxicity and side effects. As necessary, treatment sessions can be intermittent. For example, patients can receive weekly doses followed by cessation for a period of time and then treatment can be resumed. Treatment for oncological diseases with B cell depletion agents can be combined with chemotherapy such as with CHOP or fludarabine and cytoxan. Treatment of autoimmune diseases with depletion agents can be combined with therapeutic agents useful in those diseases, e.g., methotrexate.

In one example, the treatment of patients suffering from B-cell neoplasm such as non-Hodgkins lymphoma, the anti-CD20 antibodies of the invention can be administered to a human patient at a dosage range of 1 mg/kg to 20 mg/kg body weight, preferably at 2.5 mg/kg to 10 mg/kg. In one embodiment for treating an NHL, the anti-CD20 antibody is administered at a dosage of 10 mg/kg or 375 mg/m$^2$.

According to one embodiment, for treating autoimmune diseases, anti-CD20 therapies are administered at 250-1000 mg per dose for 2-4 doses every other week or every third week. For example, for treating rheumatoid arthritis, in one embodiment, Rituxan™ which is a chimeric antibody is administered at 500 mg per dose every other week for a total of 2 doses. A humanized anti-CD20 antibody, e.g., hu2H7v.16 or any other variant of hu 2H7 as disclosed herein, can be administered at less than 500 mg per dose such as at between about 200-500 mg per dose, between about 250 mg-450 mg, or 300-400 mg per dose, for 2-4 doses every other week or every 3rd week.

According to one embodiment, anti-BR3 therapies are administered at 100 mg/m2-1500 mg/m2 weekly or 1 m/kg to 20 mg/kg body weight as necessary.

The treatment methods of the invention comprises a combination of concurrently and sequentially administering the anti-CD20 antibody and the BAFF antagonist (both referred to herein as the drugs). In sequential administration, the drugs can be administered in either order, i.e., BAFF antagonist first followed by anti-CD20 antibody. The patient is treated with one drug and monitored for efficacy before treatment with the one drug. Alternatively, the patient can be initially administered both drugs and subsequent dosing can be with only one or the other drug.

To condition the patient to tolerate the drugs and/or to reduce the occurrence of adverse effects such as infusion-related symptoms which arise from the initial and subsequent administrations of the therapeutic compound, the mammal in need thereof can be administered a first or initial conditioning dose of one or both drugs and then administered at least a second therapeutically effective dose of one or both drugs wherein the second and any subsequent doses are higher than the first dose. The first dose serves to condition the mammal to tolerate the higher second therapeutic dose. In this way, the mammal is able to tolerate higher doses of the therapeutic compound than could be administered initially. A "conditioning dose" is a dose which attenuates or reduces the frequency or the severity of first dose adverse side effects associated with administration of a therapeutic compound. The conditioning dose may be a therapeutic dose, a sub-therapeutic dose, a symptomatic dose or a sub-symptomatic dose. A therapeutic dose is a dose which exhibits a therapeutic effect on the patient and a sub-therapeutic dose is a dose which dose not exhibit a therapeutic effect on the patient treated. A symptomatic dose is a dose which induces at least one adverse effect on administration and a sub-symptomatic dose is a dose which does not induce an adverse effect. Some adverse effects are fever, headache, nausea, vomiting, breathing difficulties, myalgia, and chills.

Route of Administration

The B cell depleting or promoting agents and other therapeutic agents can be administered to a human patient by a variety of methods, such as by intravenous administration, e.g., as a bolus or by continuous infusion over a period of time, by subcutaneous, intramuscular, intraperitoneal, intracerebrospinal, intra-articular, intrasynovial, intrathecal, or inhalation routes. The anti-CD20 antibody will generally be administered by intravenous or subcutaneous administration. The drugs can be administered by the same or different route.

Kits

Another embodiment of the invention is a kit comprising a BAFF binding reagent, such as an anti-BAFF antibody or other polypeptide that can bind BAFF for use in determining serum BAFF levels, and a label or package insert instructing how serum BAFF levels relate to total B cells levels or tissue B cell levels in a patient after treatment with a B cell promoting or depleting agent. Optionally, the kit comprises the B cell promoting or B cell depleting agent. In a further embodiment, the kit further comprises instructions for retreating the patient with the B cell depleting agent or other therapeutic agent based on the patient's serum BAFF levels. The package insert can contain instructions to retreat the patient when serum BAFF levels are highest or as serum BAFF levels are decreasing (e.g, B cell recovery phase). The instructions can indicate retreatment at or before the tissue B cell recovery phase before the peripheral B cell recovery phase.

The kit comprises at least one container and a label or package insert on or associated with the container. Suitable containers include, for example, bottles, vials, syringes, etc. The containers may be formed from a variety of materials such as glass or plastic. The container can have a sterile access port for extracting a therapeutic agent (for example the container may be an intravenous solution bag or a vial having a stopper pierceable by a hypodermic injection needle). The label or package insert can indicate that the composition is used for treating the particular condition, e.g., non-Hodgkin's lymphoma or rheumatoid arthritis. Additionally, the kit may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Examples of Specific Anti-BR3 Antibodies

Antibodies of this invention specifically include antibodies comprising the variable heavy chain sequence of any one of the antibodies disclosed in Table 2 (below), and BR3-binding fragments thereof that has not been produced by a hybridoma cell. Antibodies of this invention specifically include antibodies comprising a variable heavy chain sequence of any one of the antibodies in Table 2, anti-BR3 antibodies that can be competitively inhibited by an antibody in Table 2, and BR3-binding fragments thereof. According to a further embodiment, an antibody of this invention comprises the variable heavy and the variable light chain region of any one of the antibodies disclosed in Table 2, and BR3-binding fragments thereof.

TABLE 2

Examples of Anti-BR3 Antibody Sequences

| ANTIBODY | VH domain of SEQ ID NO: | VL domain of SEQ ID NO: |
|---|---|---|
| 9.1 | 1 (VL) | 2 (VH) |
| Hu9.1-graft | 3 (VL) | 4 (VH) |
| Hu9.1-73 | 5 (VL) | 6 (VH) |
| Hu9.1-70 | 7 (VL) | 8 (VH) |
| Hu9.1-56 | 3 (VL) | 9 (VH) |
| Hu9.1-51 | 3 (VL) | 10 (VH) |
| Hu9.1-59 | 3 (VL) | 11 (VH) |
| Hu9.1-61 | 3 (VL) | 12 (VH) |
| Hu9.1-A | 3 (VL) | 13 (VH) |
| Hu9.1-B | 3 (VL) | 14 (VH) |
| Hu9.1-C | 3 (VL) | 15 (VH) |
| Hu9.1-66 | 3 (VL) | 16 (VH) |
| Hu9.1-RF | 3 (VL) | 17 (VH) |
| Hu9.1-48 | 3 (VL) | 18 (VH) |
| Hu9.1-RL | 3 (VL) | 19 (VH) |
| Hu9.1-91 | 3 (VL) | 20 (VH) |
| Hu9.1-90 | 3 (VL) | 21 (VH) |
| Hu9.1-75 | 3 (VL) | 22 (VH) |
| Hu9.1-88 | 3 (VL) | 23 (VH) |
| Hu9.1RL-9 | 3 (VL) | 24 (VH) |
| Hu9.1RL-44 | 3 (VL) | 25 (VH) |
| Hu9.1RL-13 | 3 (VL) | 26 (VH) |
| Hu9.1RL-47 | 3 (VL) | 27 (VH) |
| Hu9.1RL-28 | 3 (VL) | 28 (VH) |
| Hu9.1RL-43 | 3 (VL) | 29 (VH) |
| Hu9.1RL-16 | 3 (VL) | 30 (VH) |
| Hu9.1RL-70 | 3 (VL) | 31 (VH) |
| Hu9.1RL-30 | 3 (VL) | 32 (VH) |
| Hu9.1RL-32 | 3 (VL) | 33 (VH) |
| Hu9.1RL-37 | 3 (VL) | 34 (VH) |
| Hu9.1RL-29 | 3 (VL) | 35 (VH) |
| Hu9.1RL-10 | 3 (VL) | 36 (VH) |
| Hu9.1RL-24 | 3 (VL) | 37 (VH) |
| Hu9.1RL-39 | 3 (VL) | 38 (VH) |
| Hu9.1RL-31 | 3 (VL) | 39 (VH) |
| Hu9.1RL-18 | 3 (VL) | 40 (VH) |
| Hu9.1RL-23 | 3 (VL) | 41 (VH) |
| Hu9.1RL-41 | 3 (VL) | 42 (VH) |
| Hu9.1RL-95 | 3 (VL) | 43 (VH) |
| Hu9.1RL-14 | 3 (VL) | 44 (VH) |
| Hu9.1RL-57 | 3 (VL) | 45 (VH) |
| Hu9.1RL-15 | 3 (VL) | 46 (VH) |
| Hu9.1RL-54 | 3 (VL) | 47 (VH) |
| Hu9.1RL-12 | 3 (VL) | 48 (VH) |
| Hu9.1RL-34 | 3 (VL) | 49 (VH) |
| Hu9.1RL-25 | 3 (VL) | 50 (VH) |
| Hu9.1RL-71 | 3 (VL) | 51 (VH) |
| Hu9.1RL-5 | 3 (VL) | 52 (VH) |
| Hu9.1RL-79 | 3 (VL) | 53 (VH) |
| Hu9.1RL-66 | 3 (VL) | 54 (VH) |
| Hu9.1RL-69 | 3 (VL) | 55 (VH) |
| 9.1RF-IgG | 56 (LC) | 57 (HC) |
| V3-Fab | 58 (LC) | 59 (HC) |
| V24 | 58 (LC) | 60 (VH) |
| V44 | 58 (LC) | 61 (VH) |
| V89 | 58 (LC) | 62 (VH) |
| V96 | 58 (LC) | 63 (VH) |
| V46 | 58 (LC) | 64 (VH) |
| V51 | 58 (LC) | 65 (VH) |
| V75 | 58 (LC) | 66 (VH) |
| V58 | 58 (LC) | 67 (VH) |
| V60 | 58 (LC) | 68 (VH) |
| V3-1 | 69 (VL) | 70 (VH) |
| V3-11 | 71 (VL) | 72 (VH) |
| V3-12 | 73 (VL) | 74 (VH) |
| V3-13 | 75 (VL) | 76 (VH) |
| V3-3 | 77 (VL) | 78 (VH) |
| V3-5 | 79 (VL) | 80 (VH) |
| V3-9 | 81 (VL) | 70 (VH) |
| V3-16 | 69 (VL) | 81 (VH) |
| V3-19 | 69 (VL) | 82 (VH) |
| V3-24 | 83 (VL) | 84 (VH) |
| V3-27 | 85 (VL) | 86 (VH) |
| V3-34 | 87 (VL) | 88 (VH) |
| V3-35 | 89 (VL) | 90 (VH) |
| V3-37 | 91 (VL) | 92 (VH) |
| V3-41 | 93 (VL) | 94 (VH) |
| V3-46 | 95 (VL) | 96 (VH) |
| V3-46a | 95 (VL) | 97 (VH) |
| V3-46q | 95 (VL) | 98 (VH) |
| V3-46s | 95 (VL) | 99 (VH) |
| V3-46sFab | 100 (LC) | 101 (HC) |
| V3-46s-1 | 108 (LC) | 99 (VH) |
| V3-46s-7 | 109 (LC) | 99 (VH) |
| V3-46s-9 | 110 (LC) | 99 (VH) |
| V3-46s-10 | 111 (LC) | 99 (VH) |
| V3-46s-12 | 112 (LC) | 107 (VH) |
| V3-46s-13 | 113 (LC) | 99 (VH) |
| V3-46s-29 | 114 (LC) | 99 (VH) |
| V3-46s-31 | 115 (LC) | 99 (VH) |
| V3-46s-33 | 116 (LC) | 99 (VH) |
| V3-46s-34 | 117 (LC) | 99 (VH) |
| V3-46s-37 | 118 (LC) | 99 (VH) |
| V3-46s-40 | 119 (LC) | 99 (VH) |
| V3-46s-42 | 120 (LC) | 99 (VH) |
| V3-46s-45 | 121 (LC) | 99 (VH) |

Antibodies of this invention include BR3-binding antibodies having an H3 sequence that is at least about 70% amino acid sequence identity, alternatively at least about 71%, 72%, 73%, 74%, 75%, 76%, 77%, 78%, 79%, 80%, 81%, 82%, 83%, 84%, 85%, 86%, 87%, 88%, 89%, 89%, 90%, 91%, 92%, 93%, 94%, 95%, 96%, 97%, 98%, or 99% amino acid sequence identity, to the H3 sequence of any one of the sequences of Table 2, and BR3 binding fragments of those antibodies.

Antibodies of this invention include BR3-binding antibodies having H1, H2 and H3 sequences that are at least 70% identical to the CDRs of any one of the antibodies sequences described in the Table 2, or alternatively having at least about 71%, 72%, 73%, 74%, 75%, 76%, 77%, 78%, 79%, 80%, 81%, 82%, 83%, 84%, 85%, 86%, 87%, 88%, 89%, 89%, 90%, 91%, 92%, 93%, 94%, 95%, 96%, 97%, 98%, or 99% amino acid sequence identity. According to one embodiment the H1, H2 and H3 are each at least 70% identical to SEQ ID NOs: 124, 123 and 122, respectively, and the antibody optionally comprises a VL comprising SEQ ID NO:3 or a VL that is at least 70% identical to SEQ ID NO:3.

Antibodies of this invention include BR3-binding antibodies having L1, L2 and L3 sequences that are at least 70% identical to the CDRs of any one of the antibodies described in Table 2 or alternatively having at least about 71%, 72%, 73%, 74%, 75%, 76%, 77%, 78%, 79%, 80%, 81%, 82%, 83%, 84%, 85%, 86%, 87%, 88%, 89%, 89%, 90%, 91%, 92%, 93%, 94%, 95%, 96%, 97%, 98%, or 99% amino acid sequence identity. According to one embodiment the L1, L2 and L3 are each at least 70% identical to SEQ ID NOs: 133, 134 and 135, respectively, and the antibody optionally comprises a VH comprising SEQ ID NO: 17 or a VH that is at least 70% identical to SEQ ID NO: 17.

Antibodies of this invention include BR3-binding antibodies having a VH domain with at least 70% homology to a VH domain of any one of the antibodies of Table 2, or alternatively having at least about 71%, 72%, 73%, 74%, 75%, 76%, 77%, 78%, 79%, 80%, 81%, 82%, 83%, 84%, 85%, 86%, 87%, 88%, 89%, 89%, 90%, 91%, 92%, 93%, 94%, 95%, 96%, 97%, 98%, or 99% amino acid sequence identity. In a further embodiment, in addition to said VH domain sequence, said antibody further comprises a VL domain with at least 70% homology to the VL domain of the corresponding antibody of Table 2, or alternatively having at least about 71%, 72%, 73%, 74%, 75%, 76%, 77%, 78%, 79%, 80%, 81%, 82%, 83%, 84%, 85%, 86%, 87%, 88%, 89%, 89%, 90%, 91%, 92%, 93%, 94%, 95%, 96%, 97%, 98%, or 99% amino acid sequence identity. In one embodiment, the antibody comprises the VH and VL of 9.1RF, or a anti-BR3 binding variant thereof that comprises a VH that is at least 70% identical to SEQ ID NO:17 and a VL that is at least 70% identical to SEQ ID NO:3.

According to one preferred embodiment, the antibodies of this invention specifically bind to a sequence of a native human BR3 polypeptide. According to yet another embodiment, an antibody of this invention has improved ADCC function in the presence of human effector cells compared to the antibody known as 9.1-RF Ig. According to yet another embodiment, an antibody of this invention has decreased ADCC function in the presence of human effector cells compared to the antibody known as 9.1-RF Ig. According to another embodiment, the antibody made by the process of expressing nucleic acid sequences encoding an antibody of this invention from a cell selected from the group consisting of a mammalian cell, a bacterial cell, a fungal cell, a yeast cell, an insect cell and a plant cell.

It is understood that all antibodies of this invention include antibodies lacking a signal sequence and antibodies lacking the K447 residue of the Fc region.

Examples of Specific Anti-CD20 Antibodies

CD20 antibodies include: "C2B8," which is now called "rituximab" ("RITUXAN®") (U.S. Pat. No. 5,736,137); the yttrium-[90]-labelled 2B8 murine antibody designated "Y2B8" or "Ibritumomab Tiuxetan" (ZEVALIN®) commercially available from IDEC Pharmaceuticals, Inc. (U.S. Pat. No. 5,736,137; 2B8 deposited with ATCC under accession no. HB11388 on Jun. 22, 1993); murine IgG2a "B1," also called "Tositumomab," optionally labelled with $^{131}$I to generate the "131I-B1" or "iodine I131 tositumomab" antibody (BEXXAR™) commercially available from Corixa (see, also, U.S. Pat. No. 5,595,721); murine monoclonal antibody "1F5" (Press et al. Blood 69(2):584-591 (1987) and variants thereof including "framework patched" or humanized 1F5 (WO 2003/002607, Leung, S.; ATCC deposit HB-96450); murine 2H7 and chimeric 2H7 antibody (U.S. Pat. No. 5,677,180); a humanized 2H7 (WO 2004/056312 Lowman et al.) and as set forth below); HUMAX-CD20™ fully human antibody (Genmab, Denmark; see, for example, Glennie and van de Winkel, Drug Discovery Today 8: 503-510 (2003) and Cragg et al., Blood 101: 1045-1052 (2003)); the human monoclonal antibodies set forth in WO 2004/035607 (Teeling et al.); the antibodies having complex N-glycoside-linked sugar chains bound to the Fc region described in US 2004/0093621 (Shitara et al.); CD20 binding molecules such as the AME series of antibodies, e.g., AME-133™ antibodies as set forth in WO 2004/103404 (Watkins et al., Applied Molecular Evolution); A20 antibody or variants thereof such as chimeric or humanized A20 antibody (cA20, hA20, respectively) (US 2003/0219433, Immunomedics); and monoclonal antibodies L27, G28-2, 93-1B3, B-C1 or NU-B2 available from the International Leukocyte Typing Workshop (Valentine et al., In: *Leukocyte Typing* III (McMichael, Ed., p. 440, Oxford University Press (1987)). The preferred CD20 antibodies herein are humanized, chimeric, or human CD20 antibodies, more preferably, a humanized 2H7 antibody, rituximab, chimeric or humanized A20 antibody (Immunomedics), and HUMAX-CD20™ human CD20 antibody (Genmab).

For the purposes herein, "humanized 2H7" refers to an intact antibody or antibody fragment comprising the variable light (V$_L$) sequence:

```
                                    (SEQ ID NO: 136)
DIQMTQSPSSLSASVGDRVTITCRASSSVSYMHWYQQKPGKAPKPLIYA

PSNLASGVPSRFSGSGSGTDFTLTISSLQPEDFATYYCQQWSFNPPTFG

QGTKVEIKR;
```
and variable heavy (V$_H$) sequence:

```
                                    (SEQ ID NO: 137)
EVQLVESGGGLVQPGGSLRLSCAASGYTFTSYNMHWVRQAPGKGLEWVGA

IYPGNGDTSYNQKFKGRFTISVDKSKNTLYLQMNSLRAEDTAVYYCARVV

YYSNSYWYFDVWGQGTLVTVSS
```

Where the humanized 2H7 antibody is an intact antibody, preferably it comprises the v16 light chain amino acid sequence:

```
                                    (SEQ ID NO: 138)
DIQMTQSPSSLSASVGDRVTITCRASSSVSYMHWYQQKPGKAPKPLIYAP

SNLASGVPSRFSGSGSGTDFTLTISSLQPEDFATYYCQQWSFNPPTFGQG

TKVEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC;
```
and heavy chain amino acid sequence:

```
                                    (SEQ ID NO: 139)
EVQLVESGGGLVQPGGSLRLSCAASGYTFTSYNMHWVRQAPGKGLEWVGA

IYPGNGDTSYNQKFKGRFTISVDKSKNTLYLQMNSLRAEDTAVYYCARVV

YYSNSYWYFDVWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE
```

-continued
PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLS

LSPG.

The V region of all other variants based on version 16 will have the amino acid sequences of v16 except at the positions of amino acid substitutions which are indicated in Table 3 below. Unless otherwise indicated, the 2H7 variants will have the same L chain as that of v16. Humanized antibody 2H7v.16 is also referred to as rhuMAb2H7 or Ocrelizumab.

TABLE 3

| 2H7 version | Light chain ($V_L$) changes | Heavy chain ($V_H$) changes | Fc changes |
|---|---|---|---|
| 16 for reference | — | — | — |
| 31 | — | — | S298A, E333A, K334A |
| 73 | M32L | N100A | |
| 75 | M32L | N100A | S298A, E333A, K334A |
| 96 | S92A | D56A, N100A | |
| 114 | M32L, S92A | D56A, N100A | S298A, E333A, K334A |
| 115 | M32L, S92A | D56A, N100A | S298A, E333A, K334A, E356D, M358L |
| 116 | M32L, S92A | D56A, N100A | S298A, K334A, K322A |
| 138 | M32L, S92A | D56A, N100A | S298A, E333A, K334A, K326A |
| 477 | M32L, S92A | D56A, N100A | S298A, E333A, K334A, K326A, N434W |
| 375 | — | — | K334L |
| 588 | — | — | S298A, E333A, K334A, K326A |
| 511 | M32L, S92A | D56A, N100Y, S100aR | S298A, E333A, K334A, K326A |

TABLE 4

| 2H7 version | $V_L$ SEQ ID NO. | $V_H$ SEQ ID NO. | Full L chain SEQ ID NO. | Full H chain SEQ ID NO. |
|---|---|---|---|---|
| 16 | 136 | 137 | 138 | 139 |
| 114 | 144 | 145 | 140 | 141 |
| 138 | 144 | 145 | 140 | 142 |
| 511 | 144 | 146 | 140 | 143 |

Residue numbering is according to Kabat et al., Sequences of Immunological Interest. 5th Ed. Public Health Service, National Institutes of Health, Bethesda, Md. (1991), with insertions shown as a, b, c, d, and e, and gaps shown as dashes in the sequence figures. In the CD20 binding antibodies that comprise Fc region, the C-terminal lysine (residue 447 according to the EU numbering system) of the Fc region may be removed, for example, during purification of the Ab or by recombinant engineering the nucleic acid encoding the antibody polypeptide. Accordingly, a CD20 binding antibody composition useful in this invention can comprise antibody with K447, with all K447 removed, or a mixture of antibody with and without the K447 residue.

The N-glycosylation site in IgG is at Asn297 in the CH2 domain. CD20-binding and BR3-binding antibodies useful in the treatment methods of the present invention include compositions of any of the preceding antibodies having a Fc region, wherein about 80-100% (and preferably about 90-99%) of the antibody in the composition comprises a mature core carbohydrate structure which lacks fucose, attached to the Fc region of the glycoprotein.

CD20 binding antibodies encompasss bispecific CD20 binding antibodies wherein one arm of the antibody has a H and L chain of a CD20 binding antibody such as a H and L chain of the humanized 2H7 antibody of the invention, and the other arm has V region binding specificity for a second antigen. In specific embodiments, the second antigen is selected from the group consisting of CD3, CD64, CD32A, CD16, NKG2D or other NK activating ligands.

Assay Methods

Serum BAFF levels can be measured by a variety of techniques. The most convenient techniques for assaying serum BAFF levels include western blot, dot blot, ELISA, immunoprecipitation or any other immunoassays or techniques using anti-BAFF antibodies or molecules that specifically bind BAFF. For example, a sandwich ELISA for measurement of the soluble form of BAFF can performed as described below or in Example 1. See also Zhang, J., et al., (2001) J. Immunol. 166:6-10. Briefly, 96 well plates can be coated with a purified murine anti-BAFF monoclonal antibody (clone 3D4, mIgG1) at 2 µg/ml in phosphate buffered saline (PBS) at 4° C. overnight and blocked with 1% bovine serum albumin (BSA)/PBS. All specimens can be diluted 1:10 in 3% BSA/PBS and incubated in the ELISA plate at 37° C. for four hours. After washing, the plate can be incubated first with 0.2 µg/ml biotin conjugated polyclonal anti-BAFF antibody and then with 1:30,000 diluted HRP conjugated streptavidin (Southern Biotechnology, Birmingham, Ala.). To avoid any confounding effect of rheumatoid factor activity, an mIgG1 isotype can be used as a background control for the capture antibody with each specimen. The reaction can be developed with trimethylbenzidine substrate (Sigma, St Louis, Mo.) and read in an E-Max plate reader (Molecular Devices, Sunnyvale, Calif.). In this assay, the absorbance values in the mIgG1 control wells can be subtracted from the corresponding anti-BAFF capture wells and were typically <10% of total absorbance. A standard curve using serial dilutions of recombinant BAFF can be incorporated into each assay.

All publications (including patents and patent applications) cited herein are hereby incorporated in their entirety by reference. Also incorporated herein in their entirety are U.S. Provisional Patent Application No. 60/739,266, filed Nov. 23, 2005, and the U.S. Provisional Patent Application entitled METHODS AND COMPOSITIONS RELATED TO B CELL ASSAYS, filed Nov. 10, 2006 (Inventor: Flavius Martin).

Commercially available reagents referred to in the Examples were generally used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture,* 1987; Coligan et al., *Current Protocols in Immunology,* 1991.

Throughout this specification and claims, the word "comprise," or variations such as "comprises" or "comprising," will be understood to imply the inclusion of a stated integer or group of integers but not the exclusion of any other integer or group of integers.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1—Serum BAFF is Upregulated Upon B Cell Depletion in Mice

Mice were injected with 200 ug of control (mouse IgG2a), anti-BR3 antibody or anti-CD20 antibody (N=5 mice/group). Seven days after injection, the mice were tested for B cell depletion and BAFF levels. Typically, BAFF serum levels were determined as follows: human BCMA-Fc (Genentech, Inc.) was diluted to 0.5 µg/mL in PBS and coated onto 384 well ELISA plates (Immuno Plate with MaxiSorp surface, Nunc, Neptune, N.J.) by incubating for 12-72 hr at 2-8° C. After blocking with PBS/0.5% BSA, mouse serum samples diluted in sample buffer (PBS/0.5% BSA/0.05% Tween-20/0.25% CHAPS/0.2% bovine gamma globulin/5 mM EDTA/0.35 M NaCl) were added to the plate. The plate was incubated for 2 hr at room temperature with gentle agitation on an orbital plate shaker. The plates were then washed in PBS+0.05% Tween-20 wash buffer at room temperature. A standard curve of mouse BAFF (Genentech, Inc.) diluted in the same buffer was also added (range: 1000-15.6 pg/nL). Plate-bound BAFF was detected with a rat anti-mouse BAFF monoclonal antibody (R&D Systems, Minneapolis, Minn.), and bound anti-BAFF mAb was detected using a goat anti-rat IgG Fc-HRP antibody (Jackson ImmunoResearch, West Grove, Pa.). Color was developed using tetramethyl benzidine (TMB) (Kirkegaard & Perry Laboratories, Gaithersburg, Md.), and the reaction was stopped with 1 M phosphoric acid. Sample BAFF concentrations were interpolated from a 4-parameter fit of the BAFF standard curve. The minimum quantifiable concentration, given a ¼ minimum dilution of the serum samples, was 62.5 pg/mL.

Treatments with either anti-BR3 antibody (Genentech, Inc.) or ant-CD20 antibody (Genentech, Inc.) resulted in >95% blood B cell depletion and >75% spleen and lymph node B cell depletion. At the same time, the levels of serum BAFF increased 10-20 fold after anti-BR3 antibody treatment and 4-10 fold after anti-CD20 treatment. See FIG. 1.

Based on these results, it was hypothesized that there might be a correlation between the levels of serum BAFF and the extent of B cell depletion in tissues. This hypothesis is supported by data in the following four figures. Without being bound by theory, it is likely that levels of BAFF in the serum can be dependent on the levels of its receptors present. In this way, an increase in B cell depletion or BAFF receptor blockade would result in an increase the serum BAFF concentration.

Figure 2:
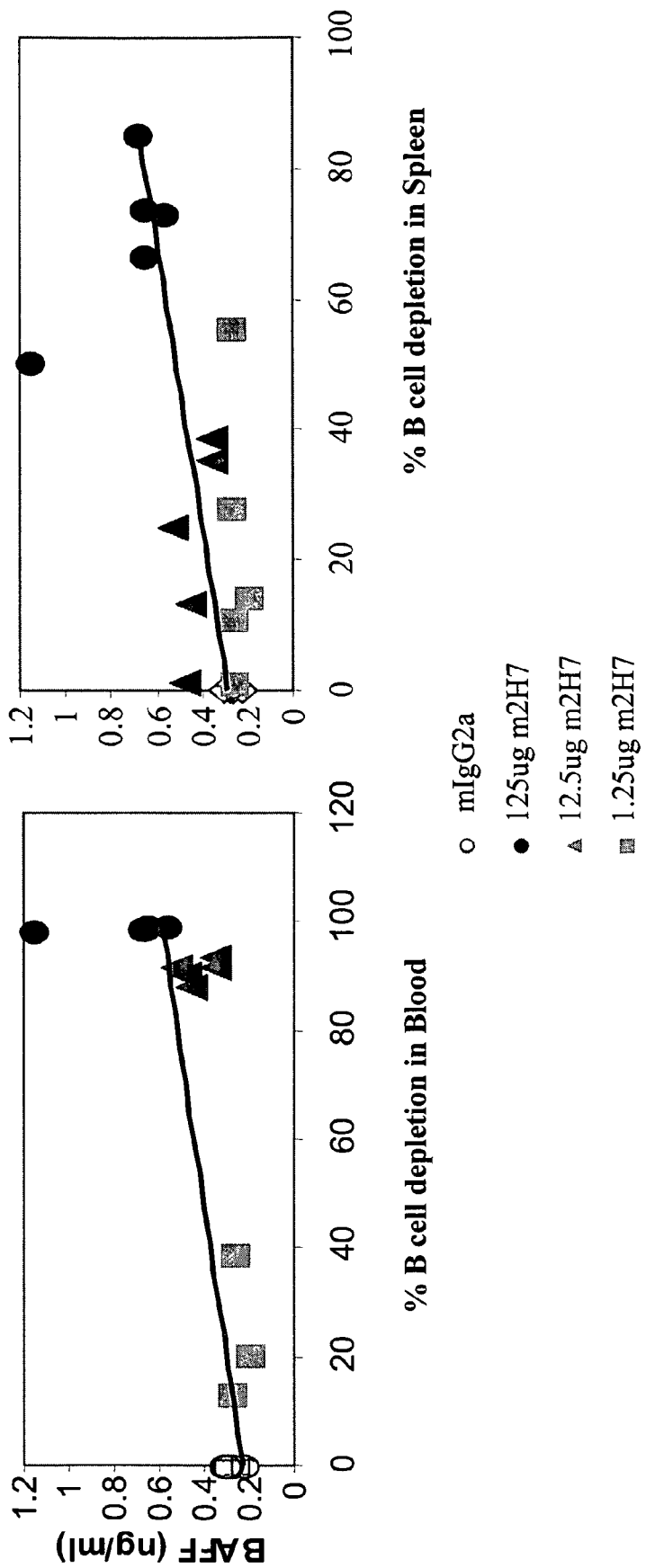
FIG. 2: Serum BAFF upregulation correlates with the extent of anti-CD20 tissue B cell depletion in mice.
Figure 3:
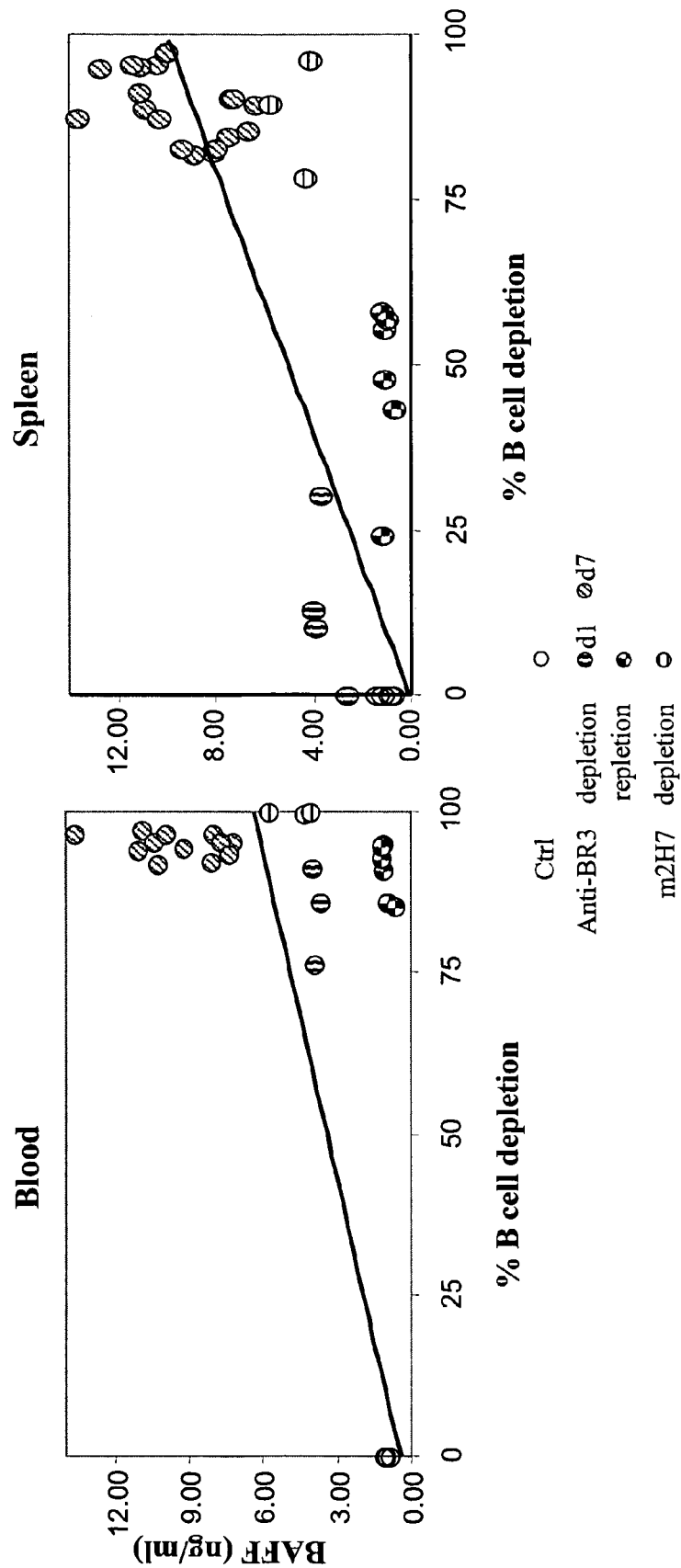
FIG. 3. Serum BAFF is an indicator of anti-BR3 tissue B cell repletion in normal mice.

Example 2—Serum BAFF Upregulation Correlates with the Extent of Anti-CD20 Tissue B Cell Depletion in Mice Five mice/group were treated with control (mIgG2a), 1.25 ug, 12.5 ug or 125 ug anti-CD20 antibody (mouse 2H7). B cell depletion in the blood and spleen were measured by flow cytometry three days later. The levels of serum BAFF are plotted against the % B cell depletion. The control mice were considered to have 0% B cell depletion. FIG. 2 shows that a large number of B cells were depleted from the blood of 12.5 ug and 125 ug treated mice. On the contrary, only the higher dose depleted extensive numbers of B cells in the spleen. There was a good dose dependent correlation between the increased serum BAFF levels and increased tissue B cell depletion (e.g., spleen). See FIG. 2.

Example 3—Serum BAFF is a Predictor of Tissue B Cell Repletion in B Cell Depleted Mice Groups of mice were treated with anti-BR3 antibody or anti-CD20 antibody (200 ug/mouse). B cell depletion was measured using flow cytometry (B220 or CD19 positive cells) with blood and spleen samples at different time points. Samples from control mice treated with mIgG2a were used to as control samples to determine % B cell depletion. After anti-BR3 treatment, there was some blood B cells depletion at day 1 with slightly more blood B cell depletion at day seven. In the spleen, on the other hand, there was only minimal tissue B cell depletion at day one and extensive tissue B cell depletion at day seven. At the same time, serum levels of BAFF were proportionally increasing between day 1 and day 7. Therefore, serum levels of BAFF and levels of B cells in the tissue (e.g., spleen and other lymphoid organs) were inversely related after treatment with the B cell depleting agent. Similarly, anti-CD20 treated mice had high levels of serum BAFF at day 7 post-treatment.

After maximum tissue B cell depletion post-treatment, serum BAFF levels decreased as the B cell levels recovered in the tissue. Only later did B cell levels recover in the blood. This indicates that the serum BAFF levels are early indicators for evaluating B cell repletion in tissues while the B cells are still depleted in the blood.

Example 4—Anti-BR3 Peripheral B Cell Depletion and Soluble BAFF Level in Cyno Blood Similar to mice, treatment of non-human primates (cynomologous monkeys) with anti-BR3 antibody causes B cell depletion in tissues with increased BAFF levels in the sera.

Figure 4:
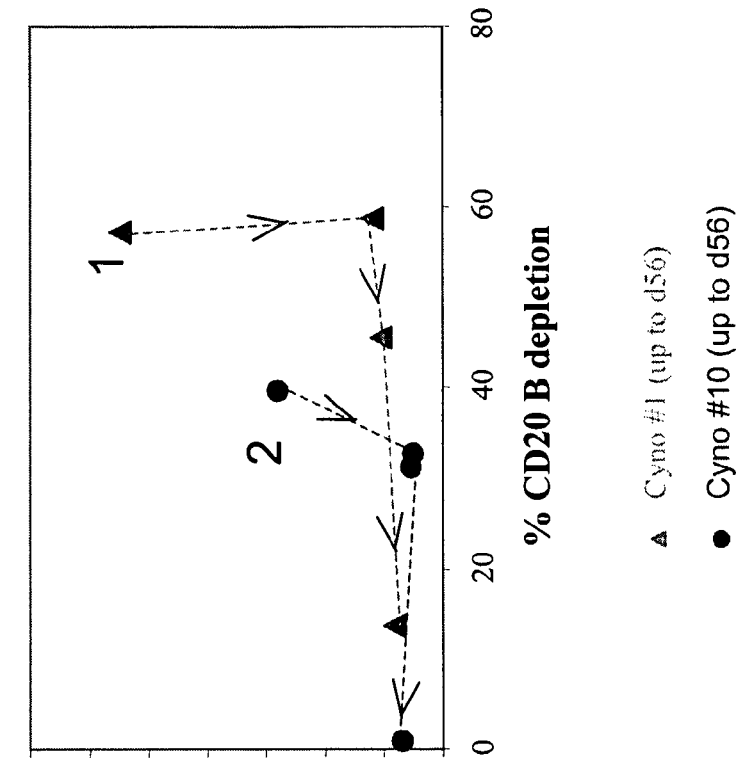
FIG. 4. Anti-BR3 peripheral B cell depletion and soluble BAFF level in cyno blood.
Figure 4:
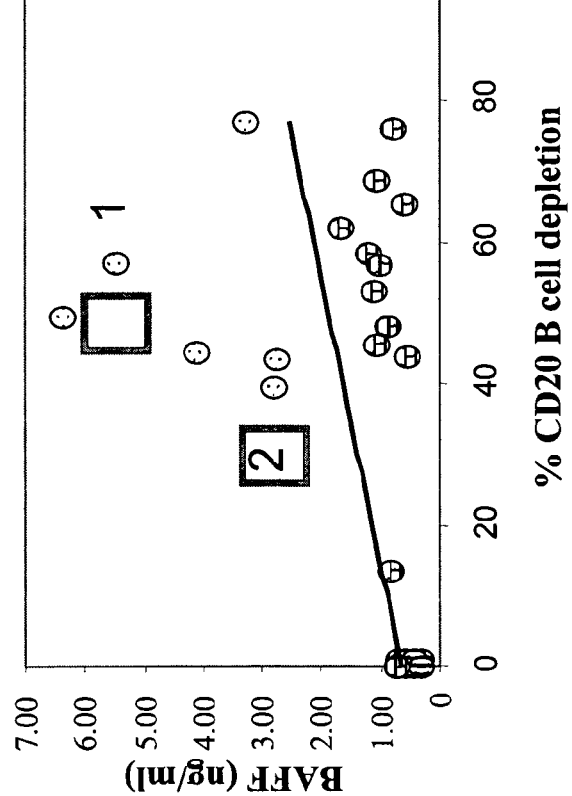

FIG. 4A shows the % CD20 blood B cell depletion and serum BAFF levels in monkeys treated with 20 mg/kg single dose anti-BR3 antibody over a 6 month post-treatment evaluation period. % CD20 blood B cell depletion was calculated by comparing the test samples to samples from the monkeys before treatment with anti-BR3 antibody. The monkeys experienced a maximum blood B cell depletion phase coinciding with elevated serum BAFF levels (delta+) followed subsequently by a drop in serum BAFF levels (delta−) and coinciding with B cell repletion. Two monkeys, labeled 1 and 2 in FIG. 4A, are singled out during depletion and are studied in more detail as described in FIG. 4B. FIG. 4B shows a kinetics depiction of B cell depletion and serum BAFF in monkey 1 and 2. The arrows show that maximum serum BAFF levels coincide with maximum B cell depletion followed by a drop in serum BAFF levels and less B cell depletion (see arrow direction). This suggests that serum BAFF drop to baseline (delta−) is an earlier event than blood B cell recovery.

Figure 5:
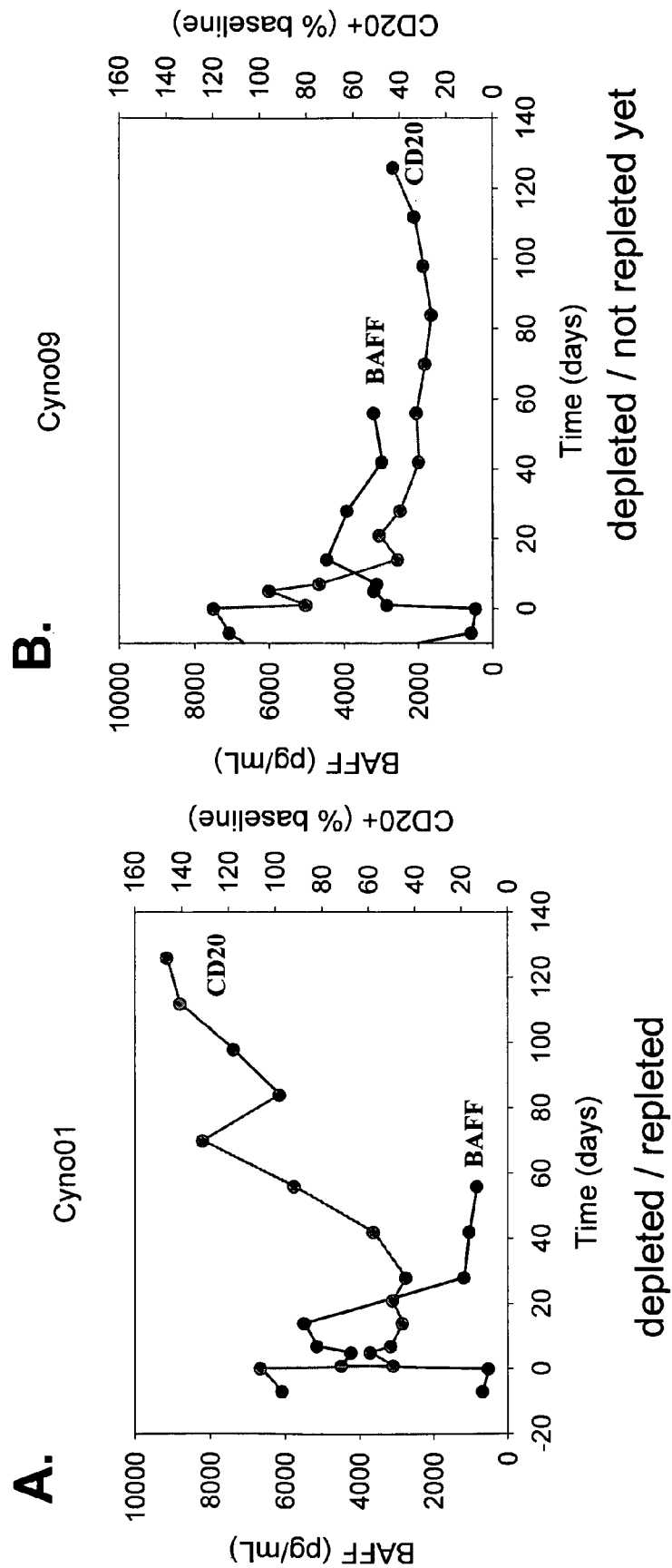
FIG. 5. Anti-BR3 peripheral CD20 B cell depletion and soluble BAFF level in cyno blood—individual kinetics in two representative cyno.
Figure 6:
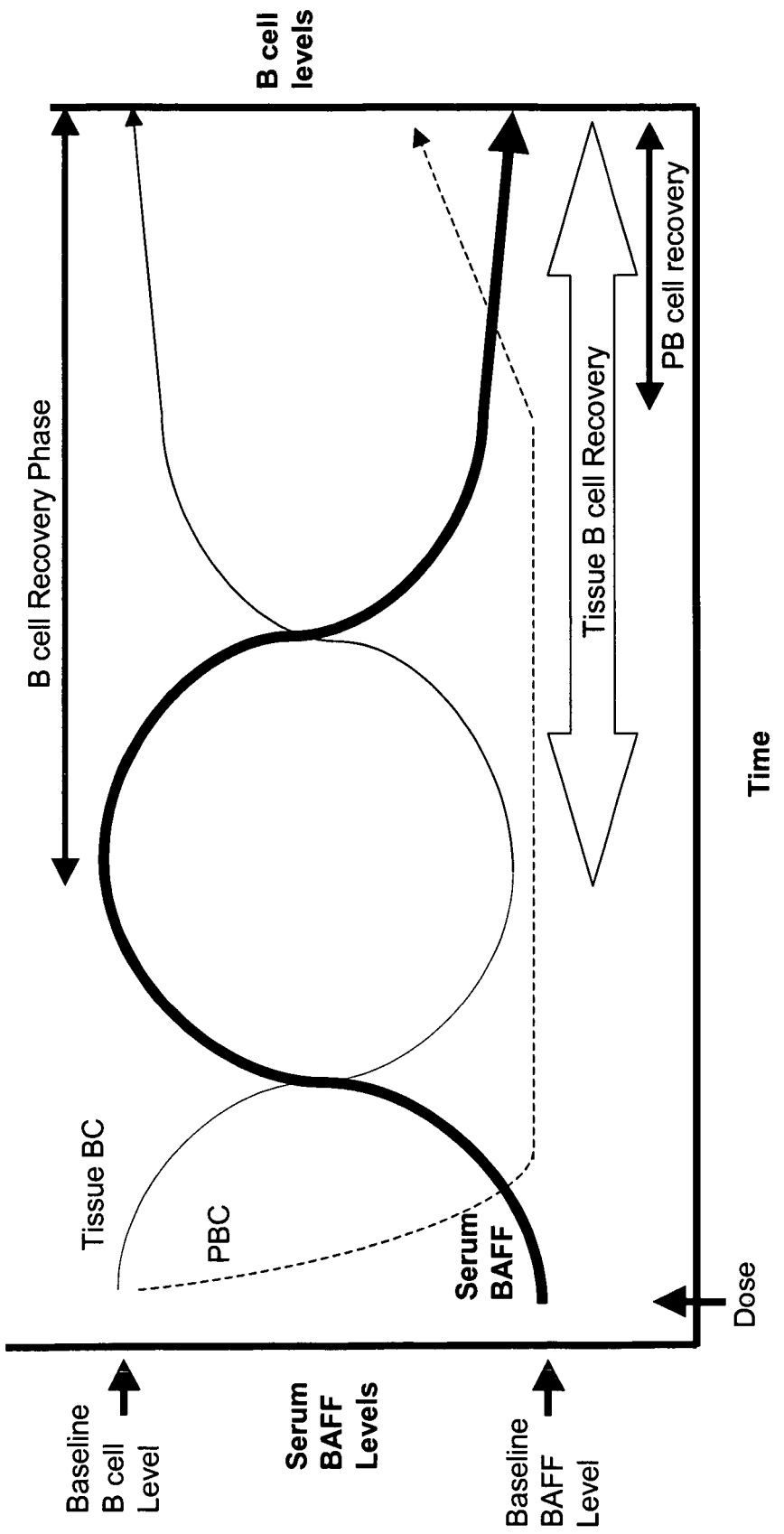
FIG. 6. Schematic diagram illustrating the delay in peripheral B cell recovery compared to tissue B cell recovery.

Example 5—Peripheral CD20 B Cell Depletion and Soluble BAFF Levels in Cyno Blood After Treatment with Anti-BR3 Antibody—Individual Kinetics in Two Representative Cyno The data from the two cyno monkeys studied in Example 4 are represented as full kinetic curves in FIG. 5. Both monkeys show that serum BAFF levels increase (delta+) concomitant with blood B cell depletion. As seen in cyno monkey #01 (FIG. 5A), serum BAFF levels drops at ~day 22 (delta−) and the B cell recovery phase begins and is fully on by ~day 40. In the cyno monkey #09 (FIG. 5B), serum BAFF levels are up while the blood B cells levels are down. Cyno monkey #09 showed little to no blood B cell recovery (see beyond day 50). This study again shows the inverse relationship between serum BAFF levels and B cell levels in the blood of cynos and, it is believed that the lag between B cell depletion and repletion in the blood versus tissue observed in mice translates to primates. Therefore, serum BAFF levels present an excellent early indicator of tissue B cell compartment size (spleen, lymph nodes, etc).

What is claimed:

1. A method for optimizing a B cell depletion therapy in a subject suffering from an immunological disorder comprising the steps of:
   (a) administering a therapeutically effective amount of a B cell depletion agent to the subject;
   (b) determining the serum BAFF level in a test sample from the subject at a first time point;
   (c) determining the serum BAFF level in a test sample from the subject at a second time point;
   (d) comparing the serum BAFF level in the test samples taken at the first and second time points, wherein an increase in the serum BAFF level from the first time point to the second time point is indicative of a decrease in the level of B cells and a decrease in the serum BAFF level from the first time point to the second time point is indicative of an increase in B cells levels in the subject; and
   (e) administering a therapeutically effective amount of the same B cell depletion agent or a different therapeutic agent to the subject whose serum BAFF levels are decreased from the first time point to the second time point, whereby said B cell depletion therapy is optimized wherein the B cell depletion agent is an anti-CD20 antibody or an anti-BR3 antibody.

2. A method of administering a B cell depletion agent to a subject previously treated with a B cell depletion agent for an immunological disorder said method comprising the steps of:
   (a) determining the serum BAFF level in a test sample from the subject at a first time point;
   (b) determining the serum BAFF level in a test sample from the subject at a second time point;
   (c) comparing the serum BAFF level in the test samples taken at the first and second time points, wherein an increase in the serum BAFF level from the first time point to the second time point is indicative of a decrease in the level of B cells and a decrease in the serum BAFF level from the first time point to the second time point is indicative of an increase in B cell levels in the subject; and
   (d) administering a therapeutically effective amount of the B cell depletion agent to the subject whose serum BAFF levels are decreased from the first time point to the second time point wherein the B cell depletion agent is an anti-CD20 antibody or an anti-BR3 antibody.

3. A method for monitoring the treatment of a subject suffering from an immunological disorder, wherein said subject has been previously treated with a B cell depletion agent, said method comprising:
 (a) determining the serum BAFF level in a test sample from the subject at a first time point;
 (b) determining the serum BAFF level in a test sample from the subject at second time point;
 (c) comparing the serum BAFF levels in the test samples taken at the first and second time points, wherein an increase in the serum BAFF level from the first time point to the second time point is indicative of a decrease in B cell levels in the subject and a decrease in the serum BAFF level from the first time point to the second time point is indicative of an increase in B cell levels in the subject; and
 (d) administering at least a second dose of a therapeutically effective amount of the same or different B cell depletion agent to the subject whose serum BAFF levels are decreased from the first time point to the second time point wherein the B cell depletion agent is an anti-CD20 antibody or an anti-BR3 antibody.

4. The method according to any one of claims 1, 2, and 3, wherein the immunological disorder is an immunodeficiency disease.

5. The method according to any one of claims 4, 2, and 3, wherein the immunological disorder is an autoimmune disease elected from the group consisting of rheumatoid arthritis, juvenile rheumatoid arthritis, systemic lupus erythematosus (SLE), Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome, glomerulonephritis, Neuromyelitis Optica (NMO) and IgG neuropathy.

6. The method according to any one of claims 1, 2, and 3, wherein the immunological disorder is a cancer selected from the group consisting of B cell lymphoma, B cell leukemia, and multiple myeloma.

7. The method according to any one of claims 1, 2, and 3, wherein the B cells express CD20.

8. The method according to any one of claims 1, 2, and 3, wherein the subject is a mammal.

9. The method according to claim 8, wherein the mammal is a human.

10. The method according to any one of claims 1, 2 and 3, wherein the antibody is an anti-CD20 antibody.

11. The method according to claim 10, wherein the anti-CD20 antibody is rituximab or 2H7.

12. The method according to claim 1, wherein the different therapeutic agent is selected from the group consisting of a T cell depleting agent, an immunosuppressive agent, a disease-modifying anti-rheumatic drug, and a vaccine.

13. The method according to claim 1, wherein the administering is during tissue B cell recovery that is prior to peripheral blood B cell recovery.

14. The method of any one of claims 1, 6, and 3, wherein the increase in the serum BAFF level is at least 4-fold.

15. The method of claim 14, wherein the increase in the serum BAFF level is at least 10-fold.

16. The method of claim 15, wherein the increase in the serum BAFF level is at least 20-fold.

17. The method of any one of claims 1, 2, and 3, wherein said serum BAFF levels are determined using an immunoassay.

18. The method of claim 3, wherein the first time point and the second time point are after treatment with a B cell depletion agent.

19. The method of claim 3, wherein a decrease in the serum BAFF levels after a prior increase in the serum BAFF levels is indicative of a B cell recovery phase.

20. The method of claim 19, wherein the B cell depletion agent is administered to said subject during said B cell recovery phase.

21. The method according to any one of claims 1, 2 and 3, wherein the antibody is an anti-BR3 antibody.

* * * * *

SEQUENCE LISTING

```
<160> NUMBER OF SEQ ID NOS: 146

<210> SEQ ID NO 1
<211> LENGTH: 108
<212> TYPE: PRT
<213> ORGANISM: Mus sp.

<400> SEQUENCE: 1

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Asn Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Thr Tyr Pro Tyr Thr Phe Gly Gly Gly Thr
            100                 105

<210> SEQ ID NO 2
<211> LENGTH: 123
<212> TYPE: PRT
<213> ORGANISM: Mus sp.

<400> SEQUENCE: 2

Glu Val Lys Leu Val Glu Ser Gly Gly Gly Leu Val Gln Pro Gly Gly
1               5                   10                  15

Ser Leu Arg Leu Ser Cys Ala Ile Ser Gly Phe Thr Val Thr Ala Tyr
            20                  25                  30

Tyr Met Ser Trp Val Arg Gln Pro Pro Gly Lys Ala Leu Glu Trp Leu
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Asn Ser Gln Ser Ile
65                  70                  75                  80

Phe Tyr Leu Gln Met Asn Thr Leu Arg Ala Glu Asp Ser Ala Thr Tyr
                85                  90                  95

Tyr Cys Ala Gln Val Arg Arg Ala Leu Asp Tyr Trp Gly Gln Gly Thr
            100                 105                 110

Thr Val Thr Val Ser Ala Ala Ser Thr Lys Gly
            115                 120
```

```
<210> SEQ ID NO 3
<211> LENGTH: 114
<212> TYPE: PRT
<213> ORGANISM: Artificial Sequence
<220> FEATURE:
<223> OTHER INFORMATION: Synthetic construct

<400> SEQUENCE: 3
```

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Tyr Ser
            20                  25                  30

Ser Asn Gln Asn Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Thr Tyr Pro Tyr Thr Phe Gly Gln Gly Thr Lys Val Glu Ile
            100                 105                 110

Lys Arg

```
<210> SEQ ID NO 4
<211> LENGTH: 118
<212> TYPE: PRT
<213> ORGANISM: Artificial Sequence
<220> FEATURE:
<223> OTHER INFORMATION: Synthetic construct

<400> SEQUENCE: 4
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Thr Ala Tyr
            20                  25                  30

Tyr Met Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Ala Asp Thr Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

```
<210> SEQ ID NO 5
<211> LENGTH: 114
<212> TYPE: PRT
<213> ORGANISM: Artificial Sequence
<220> FEATURE:
<223> OTHER INFORMATION: Synthetic construct

<400> SEQUENCE: 5
```

Asp Ile Gln Met Thr Gln Ser Pro Ser Ser Leu Ser Ala Ser Val Gly

-continued

```
            1               5                  10                 15
          Asp Arg Val Thr Ile Thr Cys Lys Ser Ser Gln Ser Leu Leu Tyr Ser
                          20                 25                 30

Ser Asn Gln Asn Asn Tyr Leu Ala Trp Tyr Gln Gln Lys Pro Gly Lys
                          35                 40                 45

Ala Pro Lys Leu Leu Ile Tyr Trp Ala Gln His Leu Asp Ser Gly Val
                  50                 55                 60

Pro Ser Arg Phe Ser Gly Ser Gly Ser Gly Thr Asp Phe Thr Leu Thr
          65                  70                 75                 80

Ile Ser Ser Leu Gln Pro Glu Asp Phe Ala Thr Tyr Tyr Cys Gln Gln
                          85                 90                 95

Tyr Tyr Thr Tyr Pro Tyr Thr Phe Gly Gln Gly Thr Lys Val Glu Ile
                         100                105                110

Lys Arg

<210> SEQ ID NO 6
<211> LENGTH: 118
<212> TYPE: PRT
<213> ORGANISM: Artificial Sequence
<220> FEATURE:
<223> OTHER INFORMATION: Synthetic construct

<400> SEQUENCE: 6

Glu Val Gln Leu Val Glu Ser Gly Gly Gly Leu Val Gln Pro Gly Gly
          1               5                  10                 15

Ser Leu Arg Leu Ser Cys Ala Ala Ser Gly Leu Pro Met Ala Gly Phe
                          20                 25                 30

Tyr Thr Ser Trp Val Arg Gln Ala Pro Gly Lys Gly Leu Glu Trp Val
                          35                 40                 45

Gly Phe Ile Arg Asp Lys Ala Asn Gly Tyr Thr Thr Glu Tyr Asn Pro
                  50                 55                 60

Ser Val Lys Gly Arg Phe Thr Ile Ser Ala Asp Thr Ser Lys Asn Thr
          65                  70                 75                 80

Ala Tyr Leu Gln Met Asn Ser Leu Arg Ala Glu Asp Thr Ala Val Tyr
                          85                 90                 95

Tyr Cys Ala Gln Val Arg Arg Ala Leu Asp Tyr Trp Gly Gln Gly Thr
                         100                105                110

Leu Val Thr Val Ser Ser
                  115

<210> SEQ ID NO 7
<211> LENGTH: 114
<212> TYPE: PRT
<213> ORGANISM: Artificial Sequence
<220> FEATURE:
<223> OTHER INFORMATION: Synthetic construct

<400> SEQUENCE: 7

Asp Ile Gln Met Thr Gln Ser Pro Ser Ser Leu Ser Ala Ser Val Gly
          1               5                  10                 15

Asp Arg Val Thr Ile Thr Cys Lys Ser Ser Gln Ser Leu Leu Tyr Ser
                          20                 25                 30

Ser Asn Gln Asn Asn Tyr Leu Ala Trp Tyr Gln Gln Lys Pro Gly Lys
                          35                 40                 45

Ala Pro Lys Leu Leu Ile Tyr Trp Ala Ser Ile Arg Asp Ser Gly Val
                  50                 55                 60

Pro Ser Arg Phe Ser Gly Ser Gly Ser Gly Thr Asp Phe Thr Leu Thr
```

```
                65                  70                  75                  80
Ile Ser Ser Leu Gln Pro Glu Asp Phe Ala Thr Tyr Tyr Cys Gln Gln
                    85                  90                  95

Tyr Tyr Thr Tyr Pro Tyr Thr Phe Gly Gln Gly Thr Lys Val Glu Ile
                100                 105                 110

Lys Arg

<210> SEQ ID NO 8
<211> LENGTH: 118
<212> TYPE: PRT
<213> ORGANISM: Artificial Sequence
<220> FEATURE:
<223> OTHER INFORMATION: Synthetic construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Asp Ser Pro Arg Ser Gly Tyr
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Ala Asp Thr Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
                100                 105                 110

Leu Val Thr Val Ser Ser
            115

<210> SEQ ID NO 9
<211> LENGTH: 118
<212> TYPE: PRT
<213> ORGANISM: Artificial Sequence
<220> FEATURE:
<223> OTHER INFORMATION: Synthetic construct

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Ala Trp Pro Val Thr Gly Tyr
            20                  25                  30

Tyr Met Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Ala Asp Thr Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
                100                 105                 110

Leu Val Thr Val Ser Ser
            115
```

<210> SEQ ID NO 10
<211> LENGTH: 118
<212> TYPE: PRT
<213> ORGANISM: Artificial Sequence
<220> FEATURE:
<223> OTHER INFORMATION: Synthetic construct

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Val Ser Ser Tyr
            20                  25                  30

Tyr Phe Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Ala Asp Thr Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115
```

<210> SEQ ID NO 11
<211> LENGTH: 118
<212> TYPE: PRT
<213> ORGANISM: Artificial Sequence
<220> FEATURE:
<223> OTHER INFORMATION: Synthetic construct

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Ser Pro Ala Val Ala Pro His
            20                  25                  30

Tyr Trp Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Ala Asp Thr Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115
```

<210> SEQ ID NO 12
<211> LENGTH: 118
<212> TYPE: PRT
<213> ORGANISM: Artificial Sequence
<220> FEATURE:
<223> OTHER INFORMATION: Synthetic construct

<400> SEQUENCE: 12

```
Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Pro Tyr Thr Ser Tyr
            20                  25                  30

Tyr Ile Thr Trp Val Arg Gln Ala Pro Gly Lys Gly Leu Glu Trp Val
                35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Ala Asp Thr Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 13
<211> LENGTH: 118
<212> TYPE: PRT
<213> ORGANISM: Artificial Sequence
<220> FEATURE:
<223> OTHER INFORMATION: Synthetic construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Gly Gly Ser Tyr
            20                  25                  30

Tyr Ile Gly Trp Val Arg Gln Ala Pro Gly Lys Gly Leu Glu Trp Val
                35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Ala Asp Thr Ser Lys Asn Thr
65                  70                  75                  80

Ala Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 14
<211> LENGTH: 118
<212> TYPE: PRT
<213> ORGANISM: Artificial Sequence
<220> FEATURE:
<223> OTHER INFORMATION: Synthetic construct

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Glu Ser Ala Tyr
            20                  25                  30

Tyr Ile Ser Trp Val Arg Gln Ala Pro Gly Lys Gly Leu Glu Trp Val
                35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Ala Asp Thr Ser Lys Asn Thr

```
                65                  70                  75                  80
Ala Tyr Leu Gln Met Asn Ser Leu Arg Ala Glu Asp Thr Ala Val Tyr
                    85                  90                  95

Tyr Cys Ala Gln Val Arg Arg Ala Leu Asp Tyr Trp Gly Gln Gly Thr
                100                 105                 110

Leu Val Thr Val Ser Ser
        115
```

<210> SEQ ID NO 15
<211> LENGTH: 118
<212> TYPE: PRT
<213> ORGANISM: Artificial Sequence
<220> FEATURE:
<223> OTHER INFORMATION: Synthetic construct

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ala Thr Ala Ala Ala Tyr
                20                  25                  30

Tyr Ile Ser Trp Val Arg Gln Ala Pro Gly Lys Gly Leu Glu Trp Val
                35                  40                  45

Gly Phe Ile Arg Asp Lys Ala Asn Gly Tyr Thr Thr Glu Tyr Asn Pro
        50                  55                  60

Ser Val Lys Gly Arg Phe Thr Ile Ser Ala Asp Thr Ser Lys Asn Thr
65                  70                  75                  80

Ala Tyr Leu Gln Met Asn Ser Leu Arg Ala Glu Asp Thr Ala Val Tyr
                    85                  90                  95

Tyr Cys Ala Gln Val Arg Arg Ala Leu Asp Tyr Trp Gly Gln Gly Thr
                100                 105                 110

Leu Val Thr Val Ser Ser
        115
```

<210> SEQ ID NO 16
<211> LENGTH: 118
<212> TYPE: PRT
<213> ORGANISM: Artificial Sequence
<220> FEATURE:
<223> OTHER INFORMATION: Synthetic construct

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ala Thr Gly Ile Gly Tyr
                20                  25                  30

Tyr Ile Ser Trp Val Arg Gln Ala Pro Gly Lys Gly Leu Glu Trp Val
                35                  40                  45

Gly Phe Ile Arg Asp Lys Ala Asn Gly Tyr Thr Thr Glu Tyr Asn Pro
        50                  55                  60

Ser Val Lys Gly Arg Phe Thr Ile Ser Ala Asp Thr Ser Lys Asn Thr
65                  70                  75                  80

Ala Tyr Leu Gln Met Asn Ser Leu Arg Ala Glu Asp Thr Ala Val Tyr
                    85                  90                  95

Tyr Cys Ala Gln Val Arg Arg Ala Leu Asp Tyr Trp Gly Gln Gly Thr
                100                 105                 110

Leu Val Thr Val Ser Ser
        115
```

```
<210> SEQ ID NO 17
<211> LENGTH: 118
<212> TYPE: PRT
<213> ORGANISM: Artificial Sequence
<220> FEATURE:
<223> OTHER INFORMATION: Synthetic construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Thr Ala Tyr
            20                  25                  30

Tyr Met Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Phe Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 18
<211> LENGTH: 118
<212> TYPE: PRT
<213> ORGANISM: Artificial Sequence
<220> FEATURE:
<223> OTHER INFORMATION: Synthetic construct

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Trp Thr Glu His Gly His
            20                  25                  30

Tyr Met Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Phe Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 19
<211> LENGTH: 118
<212> TYPE: PRT
<213> ORGANISM: Artificial Sequence
<220> FEATURE:
<223> OTHER INFORMATION: Synthetic construct

<400> SEQUENCE: 19

Glu Val Gln Leu Val Glu Ser Gly Gly Gly Leu Val Gln Pro Gly Gly
```

```
                1               5                  10                  15
Ser Leu Arg Leu Ser Cys Ala Ala Ser Gly Phe Thr Val Thr Ala Tyr
            20                  25                  30

Tyr Met Ser Trp Val Arg Gln Ala Pro Gly Lys Gly Leu Glu Trp Val
            35                  40                  45

Gly Phe Ile Arg Asp Lys Ala Asn Gly Tyr Thr Thr Glu Tyr Asn Pro
        50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Gln Val Arg Arg Ala Leu Asp Tyr Trp Gly Gln Gly Thr
            100                 105                 110

Leu Val Thr Val Ser Ser
            115
```

<210> SEQ ID NO 20
<211> LENGTH: 118
<212> TYPE: PRT
<213> ORGANISM: Artificial Sequence
<220> FEATURE:
<223> OTHER INFORMATION: Synthetic construct

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Pro Arg Gly Tyr
            20                  25                  30

Tyr Ile Ser Trp Val Arg Gln Ala Pro Gly Lys Gly Leu Glu Trp Val
            35                  40                  45

Gly Phe Ile Arg Asp Lys Ala Asn Gly Tyr Thr Thr Glu Tyr Asn Pro
        50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Gln Val Arg Arg Ala Leu Asp Tyr Trp Gly Gln Gly Thr
            100                 105                 110

Leu Val Thr Val Ser Ser
            115
```

<210> SEQ ID NO 21
<211> LENGTH: 118
<212> TYPE: PRT
<213> ORGANISM: Artificial Sequence
<220> FEATURE:
<223> OTHER INFORMATION: Synthetic construct

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Val Thr Gly Gly Ser Phe
            20                  25                  30

Tyr Ile Ser Trp Val Arg Gln Ala Pro Gly Lys Gly Leu Glu Trp Val
            35                  40                  45

Gly Phe Ile Arg Asp Lys Ala Asn Gly Tyr Thr Thr Glu Tyr Asn Pro
        50                  55                  60
```

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 22
<211> LENGTH: 118
<212> TYPE: PRT
<213> ORGANISM: Artificial Sequence
<220> FEATURE:
<223> OTHER INFORMATION: Synthetic construct

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Gly Thr Gly Tyr
            20                  25                  30

Tyr Thr Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 23
<211> LENGTH: 118
<212> TYPE: PRT
<213> ORGANISM: Artificial Sequence
<220> FEATURE:
<223> OTHER INFORMATION: Synthetic construct

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Val Thr Gly Ser
            20                  25                  30

Tyr Val Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

```
<210> SEQ ID NO 24
<211> LENGTH: 118
<212> TYPE: PRT
<213> ORGANISM: Artificial Sequence
<220> FEATURE:
<223> OTHER INFORMATION: Synthetic construct

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Thr Thr Ala Arg
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 25
<211> LENGTH: 118
<212> TYPE: PRT
<213> ORGANISM: Artificial Sequence
<220> FEATURE:
<223> OTHER INFORMATION: Synthetic construct

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Thr Ala Ser
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 26
<211> LENGTH: 118
<212> TYPE: PRT
<213> ORGANISM: Artificial Sequence
<220> FEATURE:
<223> OTHER INFORMATION: Synthetic construct

<400> SEQUENCE: 26
```

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Val Thr Ala Ser
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Gln Val Arg Arg Ala Leu Asp Tyr Trp Gly Gln Gly Thr
            100                 105                 110

Leu Val Thr Val Ser Ser
            115

<210> SEQ ID NO 27
<211> LENGTH: 118
<212> TYPE: PRT
<213> ORGANISM: Artificial Sequence
<220> FEATURE:
<223> OTHER INFORMATION: Synthetic construct

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Leu Arg Gly Ser
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Gln Val Arg Arg Ala Leu Asp Tyr Trp Gly Gln Gly Thr
            100                 105                 110

Leu Val Thr Val Ser Ser
            115

<210> SEQ ID NO 28
<211> LENGTH: 118
<212> TYPE: PRT
<213> ORGANISM: Artificial Sequence
<220> FEATURE:
<223> OTHER INFORMATION: Synthetic construct

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Ala Val Thr Gly Ser
            20                  25                  30

Tyr Ile Ala Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 29
<211> LENGTH: 118
<212> TYPE: PRT
<213> ORGANISM: Artificial Sequence
<220> FEATURE:
<223> OTHER INFORMATION: Synthetic construct

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Thr Arg Ala Val Thr Gly Tyr
            20                  25                  30

Tyr Ile Ser Trp Val Arg Gln Ala Pro Gly Lys Gly Leu Glu Trp Val
            35                  40                  45

Gly Phe Ile Arg Asp Lys Ala Asn Gly Tyr Thr Thr Glu Tyr Asn Pro
        50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 30
<211> LENGTH: 118
<212> TYPE: PRT
<213> ORGANISM: Artificial Sequence
<220> FEATURE:
<223> OTHER INFORMATION: Synthetic construct

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Ala Thr Gly His
            20                  25                  30

Tyr Ile Ala Trp Val Arg Gln Ala Pro Gly Lys Gly Leu Glu Trp Val
            35                  40                  45

Gly Phe Ile Arg Asp Lys Ala Asn Gly Tyr Thr Thr Glu Tyr Asn Pro
        50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
            85                  90                  95

Tyr Cys Ala Gln Val Arg Arg Ala Leu Asp Tyr Trp Gly Gln Gly Thr
            100                 105                 110

Leu Val Thr Val Ser Ser

<210> SEQ ID NO 31
<211> LENGTH: 118
<212> TYPE: PRT
<213> ORGANISM: Artificial Sequence
<220> FEATURE:
<223> OTHER INFORMATION: Synthetic construct

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Val Asp Lys Leu Thr Gly Ser
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115
```

<210> SEQ ID NO 32
<211> LENGTH: 118
<212> TYPE: PRT
<213> ORGANISM: Artificial Sequence
<220> FEATURE:
<223> OTHER INFORMATION: Synthetic construct

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Leu Gly Pro Gly Arg
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115
```

<210> SEQ ID NO 33
<211> LENGTH: 118
<212> TYPE: PRT
<213> ORGANISM: Artificial Sequence
<220> FEATURE:
<223> OTHER INFORMATION: Synthetic construct

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Gln Ala Thr Gly Ser
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
            115

<210> SEQ ID NO 34
<211> LENGTH: 118
<212> TYPE: PRT
<213> ORGANISM: Artificial Sequence
<220> FEATURE:
<223> OTHER INFORMATION: Synthetic construct

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Ser Met Thr Gly Val
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
            115

<210> SEQ ID NO 35
<211> LENGTH: 118
<212> TYPE: PRT
<213> ORGANISM: Artificial Sequence
<220> FEATURE:
<223> OTHER INFORMATION: Synthetic construct

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ser Leu Thr Gly Tyr
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro

```
                   50                  55                  60

Ser Val Lys Gly Arg Phe Thr Ile Ser Arg Asp Thr Ser Lys Asn Thr
 65                  70                  75                  80

Leu Tyr Leu Gln Met Asn Ser Leu Arg Ala Glu Asp Thr Ala Val Tyr
                     85                  90                  95

Tyr Cys Ala Gln Val Arg Arg Ala Leu Asp Tyr Trp Gly Gln Gly Thr
                100                 105                 110

Leu Val Thr Val Ser Ser
            115

<210> SEQ ID NO 36
<211> LENGTH: 118
<212> TYPE: PRT
<213> ORGANISM: Artificial Sequence
<220> FEATURE:
<223> OTHER INFORMATION: Synthetic construct

<400> SEQUENCE: 36

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Leu Ala Gly Tyr
                 20                  25                  30

Tyr Ile Ser Trp Val Arg Gln Ala Pro Gly Lys Gly Leu Glu Trp Val
             35                  40                  45

Gly Phe Ile Arg Asp Lys Ala Asn Gly Tyr Thr Thr Glu Tyr Asn Pro
         50                  55                  60

Ser Val Lys Gly Arg Phe Thr Ile Ser Arg Asp Thr Ser Lys Asn Thr
 65                  70                  75                  80

Leu Tyr Leu Gln Met Asn Ser Leu Arg Ala Glu Asp Thr Ala Val Tyr
                     85                  90                  95

Tyr Cys Ala Gln Val Arg Arg Ala Leu Asp Tyr Trp Gly Gln Gly Thr
                100                 105                 110

Leu Val Thr Val Ser Ser
            115

<210> SEQ ID NO 37
<211> LENGTH: 118
<212> TYPE: PRT
<213> ORGANISM: Artificial Sequence
<220> FEATURE:
<223> OTHER INFORMATION: Synthetic construct

<400> SEQUENCE: 37

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Val Asn Gly Arg
                 20                  25                  30

Tyr Ile Ser Trp Val Arg Gln Ala Pro Gly Lys Gly Leu Glu Trp Val
             35                  40                  45

Gly Phe Ile Arg Asp Lys Ala Asn Gly Tyr Thr Thr Glu Tyr Asn Pro
         50                  55                  60

Ser Val Lys Gly Arg Phe Thr Ile Ser Arg Asp Thr Ser Lys Asn Thr
 65                  70                  75                  80

Leu Tyr Leu Gln Met Asn Ser Leu Arg Ala Glu Asp Thr Ala Val Tyr
                     85                  90                  95

Tyr Cys Ala Gln Val Arg Arg Ala Leu Asp Tyr Trp Gly Gln Gly Thr
                100                 105                 110
```

```
Leu Val Thr Val Ser Ser
        115

<210> SEQ ID NO 38
<211> LENGTH: 118
<212> TYPE: PRT
<213> ORGANISM: Artificial Sequence
<220> FEATURE:
<223> OTHER INFORMATION: Synthetic construct

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Asn Gly Arg
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: Synthetic construct

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Trp Thr Gly Arg
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Synthetic construct
```

```
<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Val Thr Gly Ser
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
            115

<210> SEQ ID NO 41
<211> LENGTH: 118
<212> TYPE: PRT
<213> ORGANISM: Artificial Sequence
<220> FEATURE:
<223> OTHER INFORMATION: Synthetic construct

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Pro Tyr
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
            115

<210> SEQ ID NO 42
<211> LENGTH: 118
<212> TYPE: PRT
<213> ORGANISM: Artificial Sequence
<220> FEATURE:
<223> OTHER INFORMATION: Synthetic construct

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Ser Leu Asp Thr Ser
            20                  25                  30

Tyr Ile Ser Trp Val Arg Gln Ala Pro Gly Lys Gly Leu Glu Trp Val
        35                  40                  45
```

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
            115

<210> SEQ ID NO 43
<211> LENGTH: 118
<212> TYPE: PRT
<213> ORGANISM: Artificial Sequence
<220> FEATURE:
<223> OTHER INFORMATION: Synthetic construct

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Thr Asp Gly Thr Tyr
            20                  25                  30

Tyr Ile Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
            115

<210> SEQ ID NO 44
<211> LENGTH: 118
<212> TYPE: PRT
<213> ORGANISM: Artificial Sequence
<220> FEATURE:
<223> OTHER INFORMATION: Synthetic construct

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Val Thr Gly Ser
            20                  25                  30

Tyr Leu Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 45
<211> LENGTH: 118
<212> TYPE: PRT
<213> ORGANISM: Artificial Sequence
<220> FEATURE:
<223> OTHER INFORMATION: Synthetic construct

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Asp Thr Gly His
            20                  25                  30

Tyr Leu Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 46
<211> LENGTH: 118
<212> TYPE: PRT
<213> ORGANISM: Artificial Sequence
<220> FEATURE:
<223> OTHER INFORMATION: Synthetic construct

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Ser Leu Asn Gly Tyr
            20                  25                  30

Tyr Leu Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 47
<211> LENGTH: 118
<212> TYPE: PRT
<213> ORGANISM: Artificial Sequence
<220> FEATURE:
<223> OTHER INFORMATION: Synthetic construct

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Asp Tyr Gly Asn
            20                  25                  30

Tyr Leu Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
            115

<210> SEQ ID NO 48
<211> LENGTH: 118
<212> TYPE: PRT
<213> ORGANISM: Artificial Sequence
<220> FEATURE:
<223> OTHER INFORMATION: Synthetic construct

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Gly Thr Gly Ser
            20                  25                  30

Tyr Met Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
            115

<210> SEQ ID NO 49
<211> LENGTH: 118
<212> TYPE: PRT
<213> ORGANISM: Artificial Sequence
<220> FEATURE:
<223> OTHER INFORMATION: Synthetic construct

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Leu Thr Gly Ser
            20                  25                  30

Tyr Met Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
            50                  55                  60

Ser Val Lys Gly Arg Phe Thr Ile Ser Arg Asp Thr Ser Lys Asn Thr
 65                  70                  75                  80

Leu Tyr Leu Gln Met Asn Ser Leu Arg Ala Glu Asp Thr Ala Val Tyr
                    85                  90                  95

Tyr Cys Ala Gln Val Arg Arg Ala Leu Asp Tyr Trp Gly Gln Gly Thr
                100                 105                 110

Leu Val Thr Val Ser Ser
            115

<210> SEQ ID NO 50
<211> LENGTH: 118
<212> TYPE: PRT
<213> ORGANISM: Artificial Sequence
<220> FEATURE:
<223> OTHER INFORMATION: Synthetic construct

<400> SEQUENCE: 50

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Ile Gly Ser
                20                  25                  30

Tyr Met Ser Trp Val Arg Gln Ala Pro Gly Lys Gly Leu Glu Trp Val
            35                  40                  45

Gly Phe Ile Arg Asp Lys Ala Asn Gly Tyr Thr Thr Glu Tyr Asn Pro
        50                  55                  60

Ser Val Lys Gly Arg Phe Thr Ile Ser Arg Asp Thr Ser Lys Asn Thr
 65                  70                  75                  80

Leu Tyr Leu Gln Met Asn Ser Leu Arg Ala Glu Asp Thr Ala Val Tyr
                    85                  90                  95

Tyr Cys Ala Gln Val Arg Arg Ala Leu Asp Tyr Trp Gly Gln Gly Thr
                100                 105                 110

Leu Val Thr Val Ser Ser
            115

<210> SEQ ID NO 51
<211> LENGTH: 118
<212> TYPE: PRT
<213> ORGANISM: Artificial Sequence
<220> FEATURE:
<223> OTHER INFORMATION: Synthetic construct

<400> SEQUENCE: 51

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Ser Ala His
                20                  25                  30

Tyr Met Ser Trp Val Arg Gln Ala Pro Gly Lys Gly Leu Glu Trp Val
            35                  40                  45

Gly Phe Ile Arg Asp Lys Ala Asn Gly Tyr Thr Thr Glu Tyr Asn Pro
        50                  55                  60

Ser Val Lys Gly Arg Phe Thr Ile Ser Arg Asp Thr Ser Lys Asn Thr
 65                  70                  75                  80

Leu Tyr Leu Gln Met Asn Ser Leu Arg Ala Glu Asp Thr Ala Val Tyr
                    85                  90                  95

Tyr Cys Ala Gln Val Arg Arg Ala Leu Asp Tyr Trp Gly Gln Gly Thr

Leu Val Thr Val Ser Ser
        115

<210> SEQ ID NO 52
<211> LENGTH: 118
<212> TYPE: PRT
<213> ORGANISM: Artificial Sequence
<220> FEATURE:
<223> OTHER INFORMATION: Synthetic construct

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Ser Tyr Thr Glu Asn Gly Tyr
            20                  25                  30

Tyr Met Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 53
<211> LENGTH: 118
<212> TYPE: PRT
<213> ORGANISM: Artificial Sequence
<220> FEATURE:
<223> OTHER INFORMATION: Synthetic construct

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Glu Gly Gly Phe
            20                  25                  30

Tyr Val Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 54
<211> LENGTH: 118
<212> TYPE: PRT
<213> ORGANISM: Artificial Sequence
<220> FEATURE:

<223> OTHER INFORMATION: Synthetic construct

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Glu Asp Ser Tyr
            20                  25                  30

Tyr Val Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 55
<211> LENGTH: 118
<212> TYPE: PRT
<213> ORGANISM: Artificial Sequence
<220> FEATURE:
<223> OTHER INFORMATION: Synthetic construct

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Gly Gly Thr Phe
            20                  25                  30

Tyr Val Ser Trp Val Arg Gln Ala Pro Gly Lys Gly Leu Glu Trp Val
        35                  40                  45

Gly Phe Ile Arg Asp Lys Ala Asn Gly Tyr Thr Thr Glu Tyr Asn Pro
    50                  55                  60

Ser Val Lys Gly Arg Phe Thr Ile Ser Arg Asp Thr Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Gln Val Arg Arg Ala Leu Asp Tyr Trp Gly Gln Gly Thr
            100                 105                 110

Leu Val Thr Val Ser Ser
        115

<210> SEQ ID NO 56
<211> LENGTH: 220
<212> TYPE: PRT
<213> ORGANISM: Artificial Sequence
<220> FEATURE:
<223> OTHER INFORMATION: Synthetic construct

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Ser
            20                  25                  30

Ser Asn Gln Asn Asn Tyr Leu Ala Trp Tyr Gln Gln Lys Pro Gly Lys

```
            35                  40                  45
Ala Pro Lys Leu Leu Ile Tyr Trp Ala Ser Thr Arg Glu Ser Gly Val
    50                  55                  60
Pro Ser Arg Phe Ser Gly Ser Gly Ser Gly Thr Asp Phe Thr Leu Thr
65                  70                  75                  80
Ile Ser Ser Leu Gln Pro Glu Asp Phe Ala Thr Tyr Tyr Cys Gln Gln
                85                  90                  95
Tyr Tyr Thr Tyr Pro Tyr Thr Phe Gly Gln Gly Thr Lys Val Glu Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys
    210                 215                 220

<210> SEQ ID NO 57
<211> LENGTH: 447
<212> TYPE: PRT
<213> ORGANISM: Artificial Sequence
<220> FEATURE:
<223> OTHER INFORMATION: Synthetic construct

<400> SEQUENCE: 57

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Val Thr Ala Tyr
            20                  25                  30
Tyr Met Ser Trp Val Arg Gln Ala Pro Gly Lys Gly Leu Glu Trp Val
        35                  40                  45
Gly Phe Ile Arg Asp Lys Ala Asn Gly Tyr Thr Thr Glu Tyr Asn Pro
    50                  55                  60
Ser Val Lys Gly Arg Phe Thr Ile Ser Arg Asp Thr Ser Lys Asn Thr
65                  70                  75                  80
Phe Tyr Leu Gln Met Asn Ser Leu Arg Ala Glu Asp Thr Ala Val Tyr
                85                  90                  95
Tyr Cys Ala Gln Val Arg Arg Ala Leu Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
```

```
                180                 185                 190
Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 58
<211> LENGTH: 214
<212> TYPE: PRT
<213> ORGANISM: Artificial Sequence
<220> FEATURE:
<223> OTHER INFORMATION: Synthetic construct

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
```

```
                100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 59
<211> LENGTH: 232
<212> TYPE: PRT
<213> ORGANISM: Artificial Sequence
<220> FEATURE:
<223> OTHER INFORMATION: Synthetic construct

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30

Ser Ile His Trp Val Arg Gln Ala Pro Gly Lys Gly Leu Glu Trp Val
        35                  40                  45

Ala Trp Ile Thr Pro Ser Asp Gly Asn Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Cys Tyr Ser Ser Val Arg Gly Cys Ala Gly Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His
225                 230
```

<210> SEQ ID NO 60
<211> LENGTH: 119
<212> TYPE: PRT
<213> ORGANISM: Artificial Sequence
<220> FEATURE:
<223> OTHER INFORMATION: Synthetic construct

<400> SEQUENCE: 60

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Gly Ser
            20                  25                  30

Ser Ile His Trp Val Arg Gln Ala Pro Gly Lys Gly Leu Glu Trp Val
        35                  40                  45

Gly Thr Ile Tyr Pro Tyr Gly Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Ala Phe Val Met Ser Gly Met Asp Tyr Trp Gly Gln Gly
            100                 105                 110

Thr Leu Val Thr Val Ser Ser
        115
```

<210> SEQ ID NO 61
<211> LENGTH: 117
<212> TYPE: PRT
<213> ORGANISM: Artificial Sequence
<220> FEATURE:
<223> OTHER INFORMATION: Synthetic construct

<400> SEQUENCE: 61

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Thr Gly Ser
            20                  25                  30

Tyr Ile His Trp Val Arg Gln Ala Pro Gly Lys Gly Leu Glu Trp Val
        35                  40                  45

Ala Trp Ile Tyr Pro Asp Gly Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Ser Lys Pro Ala Gly Pro Phe Gly Tyr Trp Gly Gln Gly Thr Leu
            100                 105                 110

Val Thr Val Ser Ser
        115
```

<210> SEQ ID NO 62
<211> LENGTH: 119
<212> TYPE: PRT
<213> ORGANISM: Artificial Sequence
<220> FEATURE:
<223> OTHER INFORMATION: Synthetic construct

<400> SEQUENCE: 62

```
Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Ile Thr Gly Tyr
            20                  25                  30

Gly Ile His Trp Val Arg Gln Ala Pro Gly Lys Gly Leu Glu Trp Val
        35                  40                  45

Ala Gly Ile Thr Pro Ala Asn Gly Tyr Thr Asp Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Lys Ser Phe Pro Phe His Tyr Asn Phe Asp Tyr Trp Gly Gln Gly
            100                 105                 110

Thr Leu Val Thr Val Ser Ser
        115

<210> SEQ ID NO 63
<211> LENGTH: 120
<212> TYPE: PRT
<213> ORGANISM: Artificial Sequence
<220> FEATURE:
<223> OTHER INFORMATION: Synthetic construct

<400> SEQUENCE: 63

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ile Asn Ser Ser
            20                  25                  30

Ala Ile His Trp Val Arg Gln Ala Pro Gly Lys Gly Leu Glu Trp Val
        35                  40                  45

Gly Tyr Ile Thr Pro Ala Ser Gly Tyr Thr Asp Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Lys Gly Phe His Trp Tyr Arg Gly Phe Phe Asp Tyr Trp Gly Gln
            100                 105                 110

Gly Thr Leu Val Thr Val Ser Ser
        115                 120

<210> SEQ ID NO 64
<211> LENGTH: 116
<212> TYPE: PRT
<213> ORGANISM: Artificial Sequence
<220> FEATURE:
<223> OTHER INFORMATION: Synthetic construct

<400> SEQUENCE: 64

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ile Thr Gly Ser
            20                  25                  30

Tyr Ile His Trp Val Arg Gln Ala Pro Gly Lys Gly Leu Glu Trp Val
        35                  40                  45

Ala Trp Ile Tyr Pro Asp Gly Gly Tyr Thr Asp Tyr Ala Asp Ser Val
 50                  55                  60

Lys Gly Arg Phe Thr Ile Ser Ala Asp Thr Ser Lys Asn Thr Ala Tyr

```
                65                  70                  75                  80
Leu Gln Met Asn Ser Leu Arg Ala Glu Asp Thr Ala Val Tyr Tyr Cys
                    85                  90                  95

Ala Ser Lys Pro Ala Gly Phe Gly Tyr Trp Gly Gln Gly Thr Leu Val
                100                 105                 110

Thr Val Ser Ser
        115

<210> SEQ ID NO 65
<211> LENGTH: 125
<212> TYPE: PRT
<213> ORGANISM: Artificial Sequence
<220> FEATURE:
<223> OTHER INFORMATION: Synthetic construct

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Thr
            20                  25                  30

Gly Ile His Trp Val Arg Gln Ala Pro Gly Lys Gly Leu Glu Trp Val
        35                  40                  45

Gly Gly Ile Ser Pro Ser Ser Gly Ser Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Lys Val Val Ser Ser His Val Thr Asn Lys Tyr Val Met
                100                 105                 110

Asp Tyr Trp Gly Gln Gly Thr Leu Val Thr Val Ser Ser
            115                 120                 125

<210> SEQ ID NO 66
<211> LENGTH: 121
<212> TYPE: PRT
<213> ORGANISM: Artificial Sequence
<220> FEATURE:
<223> OTHER INFORMATION: Synthetic construct

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Gly Ser
            20                  25                  30

Trp Ile His Trp Val Arg Gln Ala Pro Gly Lys Gly Leu Glu Trp Val
        35                  40                  45

Ala Trp Ile Thr Pro Ser Asn Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Leu Ser Arg Arg Pro Trp Leu Trp Gly Met Asp Tyr Trp Gly
            100                 105                 110

Gln Gly Thr Leu Val Thr Val Ser Ser
        115                 120
```

```
<210> SEQ ID NO 67
<211> LENGTH: 120
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (30)..(33)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (99)..(104)
<223> OTHER INFORMATION: Xaa can be any naturally occurring amino acid

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Xaa Xaa Xaa
            20                  25                  30

Xaa Ile His Trp Val Arg Gln Ala Pro Gly Lys Gly Leu Glu Trp Val
        35                  40                  45

Gly Trp Ile Ser Pro Xaa Xaa Gly Asn Thr Xaa Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Xaa Xaa Xaa Xaa Xaa Xaa Ala Ala Met Asp Tyr Trp Gly Gln
            100                 105                 110

Gly Thr Leu Val Thr Val Ser Ser
        115                 120

<210> SEQ ID NO 68
<211> LENGTH: 120
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (30)..(33)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (104)..(105)
<223> OTHER INFORMATION: Xaa can be any naturally occurring amino acid

<400> SEQUENCE: 68

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Ile Xaa Xaa Xaa
            20                  25                  30

Xaa Ile His Trp Val Arg Gln Ala Pro Gly Lys Gly Leu Glu Trp Val
        35                  40                  45

Gly Xaa Ile Ser Pro Xaa Xaa Gly Asp Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ala Leu Cys Ala Pro Xaa Xaa Ala Met Asp Tyr Trp Gly Gln
            100                 105                 110

Gly Thr Leu Val Thr Val Ser Ser
            115                 120

<210> SEQ ID NO 69
<211> LENGTH: 108
<212> TYPE: PRT
<213> ORGANISM: Artificial Sequence
<220> FEATURE:
<223> OTHER INFORMATION: Synthetic construct

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Ile Thr Pro Pro
                85                  90                  95

Thr Phe Gly Gln Gly Thr Lys Val Glu Ile Lys Arg
            100                 105

<210> SEQ ID NO 70
<211> LENGTH: 125
<212> TYPE: PRT
<213> ORGANISM: Artificial Sequence
<220> FEATURE:
<223> OTHER INFORMATION: Synthetic construct

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30

Ser Ile His Trp Val Arg Gln Ala Pro Gly Lys Gly Leu Glu Trp Val
        35                  40                  45

Ala Trp Ile Thr Pro Ser Asp Gly Asn Thr Asp Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Arg Val Cys Tyr Asn Arg Leu Gly Val Cys Ala Gly Gly Met
            100                 105                 110

Asp Tyr Trp Gly Gln Gly Thr Leu Val Thr Val Ser Ser
            115                 120                 125

<210> SEQ ID NO 71
<211> LENGTH: 108
<212> TYPE: PRT
<213> ORGANISM: Artificial Sequence
<220> FEATURE:
<223> OTHER INFORMATION: Synthetic construct

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Ser Thr Ser Pro Pro
                85                  90                  95

Thr Phe Gly Gln Gly Thr Lys Val Glu Ile Lys Arg
            100                 105

<210> SEQ ID NO 72
<211> LENGTH: 125
<212> TYPE: PRT
<213> ORGANISM: Artificial Sequence
<220> FEATURE:
<223> OTHER INFORMATION: Synthetic construct

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30

Ser Ile His Trp Val Arg Gln Ala Pro Gly Lys Gly Leu Glu Trp Val
        35                  40                  45

Ala Trp Ile Thr Pro Ser Asp Gly Asn Thr Asp Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Cys Tyr Asn Asn Leu Gly Val Cys Ala Gly Ala Met
            100                 105                 110

Asp Tyr Trp Gly Gln Gly Thr Leu Val Thr Val Ser Ser
            115                 120                 125

<210> SEQ ID NO 73
<211> LENGTH: 108
<212> TYPE: PRT
<213> ORGANISM: Artificial Sequence
<220> FEATURE:
<223> OTHER INFORMATION: Synthetic construct

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg
            100                 105

<210> SEQ ID NO 74
<211> LENGTH: 125
<212> TYPE: PRT
<213> ORGANISM: Artificial Sequence
<220> FEATURE:
<223> OTHER INFORMATION: Synthetic construct

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30

Ser Ile His Trp Val Arg Gln Ala Pro Gly Lys Gly Leu Glu Trp Val
        35                  40                  45

Ala Trp Ile Thr Pro Ser Asp Gly Asn Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Cys Tyr Asp Arg Ala Arg Val Cys Ala Gly Ala Met
            100                 105                 110

Asp Tyr Trp Gly Gln Gly Thr Leu Val Thr Val Ser Ser
        115                 120                 125

<210> SEQ ID NO 75
<211> LENGTH: 108
<212> TYPE: PRT
<213> ORGANISM: Artificial Sequence
<220> FEATURE:
<223> OTHER INFORMATION: Synthetic construct

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Gly Ala Ser Asn Leu Tyr Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser His Ala Ser Pro Pro
             85                  90                  95

Thr Phe Gly Gln Gly Thr Lys Val Glu Ile Lys Arg
            100                 105

<210> SEQ ID NO 76
<211> LENGTH: 125
<212> TYPE: PRT
<213> ORGANISM: Artificial Sequence
<220> FEATURE:
<223> OTHER INFORMATION: Synthetic construct

<400> SEQUENCE: 76

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Ile Ser Arg Arg
             20                  25                  30

Ser Ile His Trp Val Arg Gln Ala Pro Gly Lys Gly Leu Glu Trp Val
         35                  40                  45

Ala Trp Ile Thr Pro Ser Asp Gly Asn Thr Asp Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ala Arg Arg Val Cys Tyr Ser Ser Val Arg Gly Cys Ala Gly Ala Met
            100                 105                 110

Asp Tyr Trp Gly Gln Gly Thr Leu Val Thr Val Ser Ser
            115                 120                 125

<210> SEQ ID NO 77
<211> LENGTH: 108
<212> TYPE: PRT
<213> ORGANISM: Artificial Sequence
<220> FEATURE:
<223> OTHER INFORMATION: Synthetic construct

<400> SEQUENCE: 77

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Arg Ile Ser Pro Pro
             85                  90                  95

Thr Phe Gly Gln Gly Thr Lys Val Glu Ile Lys Arg
            100                 105

<210> SEQ ID NO 78
<211> LENGTH: 125
<212> TYPE: PRT
```

<213> ORGANISM: Artificial Sequence
<220> FEATURE:
<223> OTHER INFORMATION: Synthetic construct

<400> SEQUENCE: 78

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30

Ser Ile His Trp Val Arg Gln Ala Pro Gly Lys Gly Leu Glu Trp Val
        35                  40                  45

Ala Trp Val Thr Pro Ser Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Cys Tyr Asn Arg Leu Gly Val Cys Ala Gly Gly Met
            100                 105                 110

Asp Tyr Trp Gly Gln Gly Thr Leu Val Thr Val Ser Ser
        115                 120                 125
```

<210> SEQ ID NO 79
<211> LENGTH: 125
<212> TYPE: PRT
<213> ORGANISM: Artificial Sequence
<220> FEATURE:
<223> OTHER INFORMATION: Synthetic construct

<400> SEQUENCE: 79

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Ser
            20                  25                  30

Ser Ile His Trp Val Arg Gln Ala Pro Gly Lys Gly Leu Glu Trp Val
        35                  40                  45

Ala Trp Ile Thr Pro Gly His Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Cys Tyr Asn Arg Leu Gly Val Cys Ala Gly Gly Met
            100                 105                 110

Asp Tyr Trp Gly Gln Gly Thr Leu Val Thr Val Ser Ser
        115                 120                 125
```

<210> SEQ ID NO 80
<211> LENGTH: 108
<212> TYPE: PRT
<213> ORGANISM: Artificial Sequence
<220> FEATURE:
<223> OTHER INFORMATION: Synthetic construct

<400> SEQUENCE: 80

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30
```

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Asn Thr Pro Pro
                85                  90                  95

Thr Phe Gly Gln Gly Thr Lys Val Glu Ile Lys Arg
            100                 105

<210> SEQ ID NO 81
<211> LENGTH: 125
<212> TYPE: PRT
<213> ORGANISM: Artificial Sequence
<220> FEATURE:
<223> OTHER INFORMATION: Synthetic construct

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Ser Ser Asn
            20                  25                  30

Ser Ile His Trp Val Arg Gln Ala Pro Gly Lys Gly Leu Glu Trp Val
        35                  40                  45

Ala Trp Ile Thr Pro Thr His Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Cys Tyr Asn Arg Leu Gly Val Cys Ala Gly Gly Met
            100                 105                 110

Asp Tyr Trp Gly Gln Gly Thr Leu Val Thr Val Ser Ser
        115                 120                 125

<210> SEQ ID NO 82
<211> LENGTH: 125
<212> TYPE: PRT
<213> ORGANISM: Artificial Sequence
<220> FEATURE:
<223> OTHER INFORMATION: Synthetic construct

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Ala Arg Ser
            20                  25                  30

Ser Ile His Trp Val Arg Gln Ala Pro Gly Lys Gly Leu Glu Trp Val
        35                  40                  45

Ala Trp Ile Leu Pro Ser Ala Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Cys Tyr Asn Arg Leu Gly Val Cys Ala Gly Gly Met

```
              100               105               110
Asp Tyr Trp Gly Gln Gly Thr Leu Val Thr Val Ser Ser
        115               120               125
```

<210> SEQ ID NO 83
<211> LENGTH: 108
<212> TYPE: PRT
<213> ORGANISM: Artificial Sequence
<220> FEATURE:
<223> OTHER INFORMATION: Synthetic construct

<400> SEQUENCE: 83

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Ile Thr Pro Pro
                85                  90                  95

Thr Phe Gly Gln Gly Thr Lys Val Glu Ile Lys Arg
            100                 105
```

<210> SEQ ID NO 84
<211> LENGTH: 125
<212> TYPE: PRT
<213> ORGANISM: Artificial Sequence
<220> FEATURE:
<223> OTHER INFORMATION: Synthetic construct

<400> SEQUENCE: 84

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Arg Ser Ile
            20                  25                  30

Ser Ile His Trp Val Arg Gln Ala Pro Gly Lys Gly Leu Glu Trp Val
        35                  40                  45

Ala Trp Ile Thr Pro Phe Asn Gly Thr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Cys Tyr Asn Arg Leu Gly Val Cys Ala Gly Gly Met
            100                 105                 110

Asp Tyr Trp Gly Gln Gly Thr Leu Val Thr Val Ser Ser
        115                 120                 125
```

<210> SEQ ID NO 85
<211> LENGTH: 108
<212> TYPE: PRT
<213> ORGANISM: Artificial Sequence
<220> FEATURE:
<223> OTHER INFORMATION: Synthetic construct

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Met Ser Pro Pro
                85                  90                  95

Thr Phe Gly Gln Gly Thr Lys Val Glu Ile Lys Arg
            100                 105

<210> SEQ ID NO 86
<211> LENGTH: 125
<212> TYPE: PRT
<213> ORGANISM: Artificial Sequence
<220> FEATURE:
<223> OTHER INFORMATION: Synthetic construct

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30

Ser Ile His Trp Val Arg Gln Ala Pro Gly Lys Gly Leu Glu Trp Val
        35                  40                  45

Ala Trp Ile Thr Pro Ser Asp Gly Asn Thr Asp Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Cys Tyr Asn His Leu Gly Val Cys Ala Gly Gly Met
            100                 105                 110

Asp Tyr Trp Gly Gln Gly Thr Leu Val Thr Val Ser Ser
        115                 120                 125

<210> SEQ ID NO 87
<211> LENGTH: 108
<212> TYPE: PRT
<213> ORGANISM: Artificial Sequence
<220> FEATURE:
<223> OTHER INFORMATION: Synthetic construct

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Ser Arg Thr Thr Pro Pro
                    85                  90                  95

Thr Phe Gly Gln Gly Thr Lys Val Glu Ile Lys Arg
                100                 105
```

<210> SEQ ID NO 88
<211> LENGTH: 125
<212> TYPE: PRT
<213> ORGANISM: Artificial Sequence
<220> FEATURE:
<223> OTHER INFORMATION: Synthetic construct

<400> SEQUENCE: 88

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Ser Asn His
                20                  25                  30

Ser Ile His Trp Val Arg Gln Ala Pro Gly Lys Gly Leu Glu Trp Val
                35                  40                  45

Ala Trp Val Thr Pro Ser Tyr Gly Ile Thr Asp Tyr Ala Asp Ser Val
            50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Cys Tyr Asn Arg Leu Gly Val Cys Ala Gly Gly Met
                100                 105                 110

Asp Tyr Trp Gly Gln Gly Thr Leu Val Thr Val Ser Ser
            115                 120                 125
```

<210> SEQ ID NO 89
<211> LENGTH: 108
<212> TYPE: PRT
<213> ORGANISM: Artificial Sequence
<220> FEATURE:
<223> OTHER INFORMATION: Synthetic construct

<400> SEQUENCE: 89

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Met Thr Pro Pro
                85                  90                  95

Thr Phe Gly Gln Gly Thr Lys Val Glu Ile Lys Arg
                100                 105
```

<210> SEQ ID NO 90
<211> LENGTH: 125
<212> TYPE: PRT
<213> ORGANISM: Artificial Sequence
<220> FEATURE:

<223> OTHER INFORMATION: Synthetic construct

<400> SEQUENCE: 90

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30

Ser Ile His Trp Val Arg Gln Ala Pro Gly Lys Gly Leu Glu Trp Val
        35                  40                  45

Ala Trp Val Thr Pro Gly Val Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Cys Tyr Asn Arg Leu Gly Val Cys Ala Gly Gly Met
            100                 105                 110

Asp Tyr Trp Gly Gln Gly Thr Leu Val Thr Val Ser Ser
        115                 120                 125
```

<210> SEQ ID NO 91
<211> LENGTH: 108
<212> TYPE: PRT
<213> ORGANISM: Artificial Sequence
<220> FEATURE:
<223> OTHER INFORMATION: Synthetic construct

<400> SEQUENCE: 91

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Ile Ser Pro Pro
                85                  90                  95

Thr Phe Gly Gln Gly Thr Lys Val Glu Ile Lys Arg
            100                 105
```

<210> SEQ ID NO 92
<211> LENGTH: 125
<212> TYPE: PRT
<213> ORGANISM: Artificial Sequence
<220> FEATURE:
<223> OTHER INFORMATION: Synthetic construct

<400> SEQUENCE: 92

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Ser Arg Arg
            20                  25                  30

Ser Ile His Trp Val Arg Gln Ala Pro Gly Lys Gly Leu Glu Trp Val
        35                  40                  45

Ala Trp Ile Thr Pro Leu Tyr Gly Ser Thr His Tyr Ala Asp Ser Val
```

```
            50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg Val Cys Tyr Asn Arg Leu Gly Val Cys Ala Gly Gly Met
            100                 105                 110

Asp Tyr Trp Gly Gln Gly Thr Leu Val Thr Val Ser Ser
        115                 120                 125

<210> SEQ ID NO 93
<211> LENGTH: 108
<212> TYPE: PRT
<213> ORGANISM: Artificial Sequence
<220> FEATURE:
<223> OTHER INFORMATION: Synthetic construct

<400> SEQUENCE: 93

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Gly Ile Ser Pro Pro
                 85                  90                  95

Thr Phe Gly Gln Gly Thr Lys Val Glu Ile Lys Arg
            100                 105

<210> SEQ ID NO 94
<211> LENGTH: 125
<212> TYPE: PRT
<213> ORGANISM: Artificial Sequence
<220> FEATURE:
<223> OTHER INFORMATION: Synthetic construct

<400> SEQUENCE: 94

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Ile Arg Asn Asn
            20                  25                  30

Ser Ile His Trp Val Arg Gln Ala Pro Gly Lys Gly Leu Glu Trp Val
         35                  40                  45

Ala Trp Val Leu Pro Ser Asn Gly Val Thr Asp Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Arg Val Cys Tyr Asn Arg Leu Gly Val Cys Ala Gly Gly Met
            100                 105                 110

Asp Tyr Trp Gly Gln Gly Thr Leu Val Thr Val Ser Ser
        115                 120                 125
```

<210> SEQ ID NO 95
<211> LENGTH: 108
<212> TYPE: PRT
<213> ORGANISM: Artificial Sequence
<220> FEATURE:
<223> OTHER INFORMATION: Synthetic construct

<400> SEQUENCE: 95

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gln Ile Ser Pro Pro
                85                  90                  95

Thr Phe Gly Gln Gly Thr Lys Val Glu Ile Lys Arg
            100                 105
```

<210> SEQ ID NO 96
<211> LENGTH: 125
<212> TYPE: PRT
<213> ORGANISM: Artificial Sequence
<220> FEATURE:
<223> OTHER INFORMATION: Synthetic construct

<400> SEQUENCE: 96

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asn Ser
            20                  25                  30

Ser Ile His Trp Val Arg Gln Ala Pro Gly Lys Gly Leu Glu Trp Val
        35                  40                  45

Ala Trp Val Leu Pro Ser Val Gly Phe Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Cys Tyr Asn Arg Leu Gly Val Cys Ala Gly Gly Met
            100                 105                 110

Asp Tyr Trp Gly Gln Gly Thr Leu Val Thr Val Ser Ser
        115                 120                 125
```

<210> SEQ ID NO 97
<211> LENGTH: 125
<212> TYPE: PRT
<213> ORGANISM: Artificial Sequence
<220> FEATURE:
<223> OTHER INFORMATION: Synthetic construct

<400> SEQUENCE: 97

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ala Ser
```

```
                    20                  25                  30
Ser Ile His Trp Val Arg Gln Ala Pro Gly Lys Gly Leu Glu Trp Val
            35                  40                  45
Ala Trp Val Leu Pro Ser Val Gly Phe Thr Asp Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Arg Val Cys Tyr Asn Arg Leu Gly Val Cys Ala Gly Gly Met
            100                 105                 110
Asp Tyr Trp Gly Gln Gly Thr Leu Val Thr Val Ser Ser
            115                 120                 125

<210> SEQ ID NO 98
<211> LENGTH: 125
<212> TYPE: PRT
<213> ORGANISM: Artificial Sequence
<220> FEATURE:
<223> OTHER INFORMATION: Synthetic construct

<400> SEQUENCE: 98

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Ile Ser Gln Ser
            20                  25                  30
Ser Ile His Trp Val Arg Gln Ala Pro Gly Lys Gly Leu Glu Trp Val
            35                  40                  45
Ala Trp Val Leu Pro Ser Val Gly Phe Thr Asp Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Arg Val Cys Tyr Asn Arg Leu Gly Val Cys Ala Gly Gly Met
            100                 105                 110
Asp Tyr Trp Gly Gln Gly Thr Leu Val Thr Val Ser Ser
            115                 120                 125

<210> SEQ ID NO 99
<211> LENGTH: 125
<212> TYPE: PRT
<213> ORGANISM: Artificial Sequence
<220> FEATURE:
<223> OTHER INFORMATION: Synthetic construct

<400> SEQUENCE: 99

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Ile Ser Ser Ser
            20                  25                  30
Ser Ile His Trp Val Arg Gln Ala Pro Gly Lys Gly Leu Glu Trp Val
            35                  40                  45
Ala Trp Val Leu Pro Ser Val Gly Phe Thr Asp Tyr Ala Asp Ser Val
    50                  55                  60
Lys Gly Arg Phe Thr Ile Ser Ala Asp Thr Ser Lys Asn Thr Ala Tyr
65                  70                  75                  80
```

Leu Gln Met Asn Ser Leu Arg Ala Glu Asp Thr Ala Val Tyr Tyr Cys
                85                  90                  95

Ala Arg Arg Val Cys Tyr Asn Arg Leu Gly Val Cys Ala Gly Gly Met
            100                 105                 110

Asp Tyr Trp Gly Gln Gly Thr Leu Val Thr Val Ser Ser
        115                 120                 125

<210> SEQ ID NO 100
<211> LENGTH: 214
<212> TYPE: PRT
<213> ORGANISM: Artificial Sequence
<220> FEATURE:
<223> OTHER INFORMATION: Synthetic construct

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gln Ile Ser Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 101
<211> LENGTH: 232
<212> TYPE: PRT
<213> ORGANISM: Artificial Sequence
<220> FEATURE:
<223> OTHER INFORMATION: Synthetic construct

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Ser
            20                  25                  30

Ser Ile His Trp Val Arg Gln Ala Pro Gly Lys Gly Leu Glu Trp Val
        35                  40                  45

```
Ala Trp Val Leu Pro Ser Val Gly Phe Thr Asp Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Arg Val Cys Tyr Asn Arg Leu Gly Val Cys Ala Gly Gly Met
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His
225                 230

<210> SEQ ID NO 102
<211> LENGTH: 285
<212> TYPE: PRT
<213> ORGANISM: Homo sapiens

<400> SEQUENCE: 102

Met Asp Asp Ser Thr Glu Arg Glu Gln Ser Arg Leu Thr Ser Cys Leu
  1               5                  10                  15

Lys Lys Arg Glu Glu Met Lys Leu Lys Glu Cys Val Ser Ile Leu Pro
             20                  25                  30

Arg Lys Glu Ser Pro Ser Val Arg Ser Ser Lys Asp Gly Lys Leu Leu
         35                  40                  45

Ala Ala Thr Leu Leu Leu Ala Leu Leu Ser Cys Cys Leu Thr Val Val
     50                  55                  60

Ser Phe Tyr Gln Val Ala Ala Leu Gln Gly Asp Leu Ala Ser Leu Arg
 65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
            115                 120                 125

Ser Arg Asn Lys Arg Ala Val Gln Gly Pro Glu Glu Thr Val Thr Gln
130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
```

```
              180                 185                 190
Phe Phe Ile Tyr Gly Gln Val Leu Tyr Thr Asp Lys Thr Tyr Ala Met
            195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 103
<211> LENGTH: 184
<212> TYPE: PRT
<213> ORGANISM: Homo sapiens

<400> SEQUENCE: 103

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
        35                  40                  45

Ser Ser Pro Ala Pro Arg Thr Ala Leu Gln Pro Gln Glu Ser Val Gly
    50                  55                  60

Ala Gly Ala Gly Glu Ala Ala Leu Pro Leu Pro Gly Leu Leu Phe Gly
65                  70                  75                  80

Ala Pro Ala Leu Leu Gly Leu Ala Leu Val Leu Ala Leu Val Leu Val
                85                  90                  95

Gly Leu Val Ser Trp Arg Arg Arg Gln Arg Arg Leu Arg Gly Ala Ser
            100                 105                 110

Ser Ala Glu Ala Pro Asp Gly Asp Lys Asp Ala Pro Glu Pro Leu Asp
        115                 120                 125

Lys Val Ile Ile Leu Ser Pro Gly Ile Ser Asp Ala Thr Ala Pro Ala
    130                 135                 140

Trp Pro Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
            180

<210> SEQ ID NO 104
<211> LENGTH: 61
<212> TYPE: PRT
<213> ORGANISM: Homo sapiens

<400> SEQUENCE: 104

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
```

```
                35                  40                  45
Ser Ser Pro Ala Pro Arg Thr Ala Leu Gln Pro Gln Glu
    50                  55                  60

<210> SEQ ID NO 105
<211> LENGTH: 64
<212> TYPE: PRT
<213> ORGANISM: Mus sp.

<400> SEQUENCE: 105

Met Gly Ala Arg Arg Leu Arg Val Arg Ser Gln Arg Ser Arg Asp Ser
1               5                   10                  15

Ser Val Pro Thr Gln Cys Asn Gln Thr Glu Cys Phe Asp Pro Leu Val
            20                  25                  30

Arg Asn Cys Val Ser Cys Glu Leu Phe His Thr Pro Asp Thr Gly His
        35                  40                  45

Thr Ser Ser Leu Glu Pro Gly Thr Ala Leu Gln Pro Gln Glu Gly Ser
    50                  55                  60

<210> SEQ ID NO 106
<211> LENGTH: 314
<212> TYPE: PRT
<213> ORGANISM: Artificial Sequence
<220> FEATURE:
<223> OTHER INFORMATION: Synthetic construct

<400> SEQUENCE: 106

Met Ser Ala Leu Leu Ile Leu Ala Leu Val Gly Ala Ala Val Ala Ser
1               5                   10                  15

Thr Gly Ala Arg Arg Leu Arg Val Arg Ser Gln Arg Ser Arg Asp Ser
            20                  25                  30

Ser Val Pro Thr Gln Cys Asn Gln Thr Glu Cys Phe Asp Pro Leu Val
        35                  40                  45

Arg Asn Cys Val Ser Cys Glu Leu Phe His Thr Pro Asp Thr Gly His
    50                  55                  60

Thr Ser Ser Leu Glu Pro Gly Thr Ala Leu Gln Pro Gln Glu Gly Gln
65                  70                  75                  80

Val Thr Gly Asp Lys Lys Ile Val Pro Arg Asp Cys Gly Cys Lys Pro
                85                  90                  95

Cys Ile Cys Thr Val Pro Glu Val Ser Ser Val Phe Ile Phe Pro Pro
            100                 105                 110

Lys Pro Lys Asp Val Leu Thr Ile Thr Leu Thr Pro Lys Val Thr Cys
        115                 120                 125

Val Val Val Asp Ile Ser Lys Asp Asp Pro Glu Val Gln Phe Ser Trp
    130                 135                 140

Phe Val Asp Asp Val Glu Val His Thr Ala Gln Thr Gln Pro Arg Glu
145                 150                 155                 160

Glu Gln Phe Asn Ser Thr Phe Arg Ser Val Ser Glu Leu Pro Ile Met
                165                 170                 175

His Gln Asp Trp Leu Asn Gly Lys Glu Phe Lys Cys Arg Val Asn Ser
            180                 185                 190

Ala Ala Phe Pro Ala Pro Ile Glu Lys Thr Ile Ser Lys Thr Lys Gly
        195                 200                 205

Arg Pro Lys Ala Pro Gln Val Tyr Thr Ile Pro Pro Pro Lys Glu Gln
    210                 215                 220

Met Ala Lys Asp Lys Val Ser Leu Thr Cys Met Ile Thr Asp Phe Phe
225                 230                 235                 240
```

```
Pro Glu Asp Ile Thr Val Glu Trp Gln Trp Asn Gly Gln Pro Ala Glu
            245                 250                 255

Asn Tyr Lys Asn Thr Gln Pro Ile Met Asn Thr Asn Gly Ser Tyr Phe
            260                 265                 270

Val Tyr Ser Lys Leu Asn Val Gln Lys Ser Asn Trp Glu Ala Gly Asn
            275                 280                 285

Thr Phe Thr Cys Ser Val Leu His Glu Gly Leu His Asn His His Thr
            290                 295                 300

Glu Lys Ser Leu Ser His Ser Pro Gly Lys
305                 310
```

<210> SEQ ID NO 107
<211> LENGTH: 125
<212> TYPE: PRT
<213> ORGANISM: Artificial Sequence
<220> FEATURE:
<223> OTHER INFORMATION: Synthetic construct

<400> SEQUENCE: 107

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ala Ser Ser
            20                  25                  30

Ser Ile His Trp Val Arg Gln Ala Pro Gly Lys Gly Leu Glu Trp Val
            35                  40                  45

Ala Trp Val Leu Pro Ser Val Gly Phe Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Val Cys Tyr Asn Arg Leu Gly Val Cys Ala Gly Gly Met
            100                 105                 110

Asp Tyr Trp Gly Gln Gly Thr Leu Val Thr Val Ser Ser
        115                 120                 125
```

<210> SEQ ID NO 108
<211> LENGTH: 107
<212> TYPE: PRT
<213> ORGANISM: Artificial Sequence
<220> FEATURE:
<223> OTHER INFORMATION: Synthetic construct

<400> SEQUENCE: 108

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Ala Thr Ser
            20                  25                  30

Val Ala Trp Tyr Gln Gln Lys Pro Gly Lys Ala Pro Lys Leu Leu Ile
            35                  40                  45

Phe Ala Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gln Ile Ser Pro Pro
                85                  90                  95

Thr Phe Gly Gln Gly Thr Lys Val Glu Ile Lys
            100                 105
```

<210> SEQ ID NO 109
<211> LENGTH: 107
<212> TYPE: PRT
<213> ORGANISM: Artificial Sequence
<220> FEATURE:
<223> OTHER INFORMATION: Synthetic construct

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Ser Ser Ser
            20                  25                  30

Val Ala Trp Tyr Gln Gln Lys Pro Gly Lys Ala Pro Lys Leu Leu Ile
        35                  40                  45

Phe Ser Ala Ser Phe Leu Phe Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Val Ser Pro Pro
                85                  90                  95

Thr Phe Gly Gln Gly Thr Lys Val Glu Ile Lys
            100                 105

<210> SEQ ID NO 110
<211> LENGTH: 107
<212> TYPE: PRT
<213> ORGANISM: Artificial Sequence
<220> FEATURE:
<223> OTHER INFORMATION: Synthetic construct

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Ser Thr Ala
            20                  25                  30

Val Ala Trp Tyr Gln Gln Lys Pro Gly Lys Ala Pro Lys Leu Leu Ile
        35                  40                  45

Phe Ala Ala Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gln Ile Ser Pro Pro
                85                  90                  95

Thr Phe Gly Gln Gly Thr Lys Val Glu Ile Lys
            100                 105

<210> SEQ ID NO 111
<211> LENGTH: 107
<212> TYPE: PRT
<213> ORGANISM: Artificial Sequence
<220> FEATURE:
<223> OTHER INFORMATION: Synthetic construct

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Ser Ser Ala
            20                  25                  30

Val Ala Trp Tyr Gln Gln Lys Pro Gly Lys Ala Pro Lys Leu Leu Ile
            35                  40                  45

Phe Ala Ala Ser Tyr Leu Phe Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gln Val Ser Pro Pro
                85                  90                  95

Thr Phe Gly Gln Gly Thr Lys Val Glu Ile Lys
            100                 105

<210> SEQ ID NO 112
<211> LENGTH: 107
<212> TYPE: PRT
<213> ORGANISM: Artificial Sequence
<220> FEATURE:
<223> OTHER INFORMATION: Synthetic construct

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Ser Ser Ala
            20                  25                  30

Val Ala Trp Tyr Gln Gln Lys Pro Gly Lys Ala Pro Lys Leu Leu Ile
            35                  40                  45

Phe Ala Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gln Ile Ser Pro Pro
                85                  90                  95

Thr Phe Gly Gln Gly Thr Lys Val Glu Ile Lys
            100                 105

<210> SEQ ID NO 113
<211> LENGTH: 107
<212> TYPE: PRT
<213> ORGANISM: Artificial Sequence
<220> FEATURE:
<223> OTHER INFORMATION: Synthetic construct

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Glu Ile Ala Thr Ala
            20                  25                  30

Val Ala Trp Tyr Gln Gln Lys Pro Gly Lys Ala Pro Lys Leu Leu Ile
            35                  40                  45

Phe Ala Ala Ser Tyr Leu Phe Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gln Val Ala Pro Pro
                85                  90                  95

Thr Phe Gly Gln Gly Thr Lys Val Glu Ile Lys
            100                 105

```
<210> SEQ ID NO 114
<211> LENGTH: 107
<212> TYPE: PRT
<213> ORGANISM: Artificial Sequence
<220> FEATURE:
<223> OTHER INFORMATION: Synthetic construct

<400> SEQUENCE: 114
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Glu Ile Ala Thr Ala
            20                  25                  30

Val Ala Trp Tyr Gln Gln Lys Pro Gly Lys Ala Pro Lys Leu Leu Ile
        35                  40                  45

Phe Ala Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Val Ser Pro Pro
                85                  90                  95

Thr Phe Gly Gln Gly Thr Lys Val Glu Ile Lys
            100                 105

```
<210> SEQ ID NO 115
<211> LENGTH: 107
<212> TYPE: PRT
<213> ORGANISM: Artificial Sequence
<220> FEATURE:
<223> OTHER INFORMATION: Synthetic construct

<400> SEQUENCE: 115
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ala Thr Ser
            20                  25                  30

Val Ala Trp Tyr Gln Gln Lys Pro Gly Lys Ala Pro Lys Leu Leu Ile
        35                  40                  45

Phe Ala Ala Ser Tyr Leu Phe Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gln Val Ser Pro Pro
                85                  90                  95

Thr Phe Gly Gln Gly Thr Lys Val Glu Ile Lys
            100                 105

```
<210> SEQ ID NO 116
<211> LENGTH: 107
<212> TYPE: PRT
<213> ORGANISM: Artificial Sequence
<220> FEATURE:
<223> OTHER INFORMATION: Synthetic construct

<400> SEQUENCE: 116
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Glu Ile Ser Thr Ala
            20                  25                  30

Val Ala Trp Tyr Gln Gln Lys Pro Gly Lys Ala Pro Lys Leu Leu Ile
        35                  40                  45

```
Phe Ser Ala Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Glu Val Ser Pro Pro
                 85                  90                  95

Thr Phe Gly Gln Gly Thr Lys Val Glu Ile Lys
            100                 105

<210> SEQ ID NO 117
<211> LENGTH: 107
<212> TYPE: PRT
<213> ORGANISM: Artificial Sequence
<220> FEATURE:
<223> OTHER INFORMATION: Synthetic construct

<400> SEQUENCE: 117

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Asp Ile Ser Ser Ala
                 20                  25                  30

Val Ala Trp Tyr Gln Gln Lys Pro Gly Lys Ala Pro Lys Leu Leu Ile
             35                  40                  45

Phe Ser Ala Ser Phe Leu Phe Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Gln Val Ser Pro Pro
                 85                  90                  95

Thr Phe Gly Gln Gly Thr Lys Val Glu Ile Lys
            100                 105

<210> SEQ ID NO 118
<211> LENGTH: 107
<212> TYPE: PRT
<213> ORGANISM: Artificial Sequence
<220> FEATURE:
<223> OTHER INFORMATION: Synthetic construct

<400> SEQUENCE: 118

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ala Thr Ala
                 20                  25                  30

Val Ala Trp Tyr Gln Gln Lys Pro Gly Lys Ala Pro Lys Leu Leu Ile
             35                  40                  45

Phe Ala Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Gln Ile Ser Pro Pro
                 85                  90                  95

Thr Phe Gly Gln Gly Thr Lys Val Glu Ile Lys
            100                 105

<210> SEQ ID NO 119
<211> LENGTH: 107
<212> TYPE: PRT
```

```
<213> ORGANISM: Artificial Sequence
<220> FEATURE:
<223> OTHER INFORMATION: Synthetic construct

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Glu Ile Ala Thr Ser
            20                  25                  30

Val Ala Trp Tyr Gln Gln Lys Pro Gly Lys Ala Pro Lys Leu Leu Ile
        35                  40                  45

Phe Ser Ala Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gln Val Ser Pro Pro
                85                  90                  95

Thr Phe Gly Gln Gly Thr Lys Val Glu Ile Lys
            100                 105

<210> SEQ ID NO 120
<211> LENGTH: 107
<212> TYPE: PRT
<213> ORGANISM: Artificial Sequence
<220> FEATURE:
<223> OTHER INFORMATION: Synthetic construct

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Ser Thr Ala
            20                  25                  30

Val Ala Trp Tyr Gln Gln Lys Pro Gly Lys Ala Pro Lys Leu Leu Ile
        35                  40                  45

Tyr Ala Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Gln Ile Ser Pro Pro
                85                  90                  95

Thr Phe Gly Gln Gly Thr Lys Val Glu Ile Lys
            100                 105

<210> SEQ ID NO 121
<211> LENGTH: 107
<212> TYPE: PRT
<213> ORGANISM: Artificial Sequence
<220> FEATURE:
<223> OTHER INFORMATION: Synthetic construct

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Val Ser Ser Ala
            20                  25                  30

Val Ala Trp Tyr Gln Gln Lys Pro Gly Lys Ala Pro Lys Leu Leu Ile
        35                  40                  45

Phe Ala Ala Ser Tyr Leu Phe Ser Gly Val Pro Ser Arg Phe Ser Gly
    50                  55                  60
```

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Ser Gln Val Ser Pro Pro
                 85                  90                  95

Thr Phe Gly Gln Gly Thr Lys Val Glu Ile Lys
            100                 105

<210> SEQ ID NO 122
<211> LENGTH: 8
<212> TYPE: PRT
<213> ORGANISM: Mus sp.

<400> SEQUENCE: 122

Gln Val Arg Arg Ala Leu Asp Tyr
1               5

<210> SEQ ID NO 123
<211> LENGTH: 20
<212> TYPE: PRT
<213> ORGANISM: Mus sp.

<400> SEQUENCE: 123

Gly Phe Ile Arg Asp Lys Ala Asn Gly Tyr Thr Thr Glu Tyr Asn Pro
1               5                   10                  15

Ser Val Lys Gly
            20

<210> SEQ ID NO 124
<211> LENGTH: 10
<212> TYPE: PRT
<213> ORGANISM: Mus sp.

<400> SEQUENCE: 124

Gly Phe Thr Val Thr Ala Tyr Tyr Met Ser
1               5                   10

<210> SEQ ID NO 125
<211> LENGTH: 16
<212> TYPE: PRT
<213> ORGANISM: Artificial Sequence
<220> FEATURE:
<223> OTHER INFORMATION: Synthetic peptide

<400> SEQUENCE: 125

Arg Val Cys Tyr Asn Arg Leu Gly Val Cys Ala Gly Gly Met Asp Tyr
1               5                   10                  15

<210> SEQ ID NO 126
<211> LENGTH: 10
<212> TYPE: PRT
<213> ORGANISM: Artificial Sequence
<220> FEATURE:
<223> OTHER INFORMATION: Synthetic peptide

<400> SEQUENCE: 126

Gly Phe Thr Ile Ser Ser Asn Ser Ile His
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Synthetic peptide

```
<400> SEQUENCE: 127

Ala Trp Ile Thr Pro Ser Asp Gly Asn Thr Asp
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Synthetic peptide

<400> SEQUENCE: 128

Gly Phe Thr Ile Ser Ser Ser Ser Ile His
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Synthetic peptide

<400> SEQUENCE: 129

Ala Trp Val Leu Pro Ser Val Gly Phe Thr Asp
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Synthetic peptide

<400> SEQUENCE: 130

Arg Ala Ser Glu Asp Ile Ser Thr Ala Val Ala
1               5                   10

<210> SEQ ID NO 131
<211> LENGTH: 8
<212> TYPE: PRT
<213> ORGANISM: Artificial Sequence
<220> FEATURE:
<223> OTHER INFORMATION: Synthetic peptide

<400> SEQUENCE: 131

Tyr Ala Ala Ser Phe Leu Tyr Ser
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic peptide

<400> SEQUENCE: 132

Gln Gln Ser Gln Ile Ser Pro Pro Thr
1               5

<210> SEQ ID NO 133
<211> LENGTH: 17
<212> TYPE: PRT
<213> ORGANISM: Mus sp.

<400> SEQUENCE: 133
```

```
Lys Ser Ser Gln Ser Leu Leu Tyr Ser Ser Asn Gln Asn Asn Tyr Leu
1               5                   10                  15
Ala

<210> SEQ ID NO 134
<211> LENGTH: 7
<212> TYPE: PRT
<213> ORGANISM: Mus sp.

<400> SEQUENCE: 134

Trp Ala Ser Thr Arg Glu Ser
1               5

<210> SEQ ID NO 135
<211> LENGTH: 9
<212> TYPE: PRT
<213> ORGANISM: Mus sp.

<400> SEQUENCE: 135

Gln Gln Tyr Tyr Thr Tyr Pro Tyr Thr
1               5

<210> SEQ ID NO 136
<211> LENGTH: 107
<212> TYPE: PRT
<213> ORGANISM: Artificial sequence
<220> FEATURE:
<223> OTHER INFORMATION: sequence is synthesized

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys Arg
            100                 105

<210> SEQ ID NO 137
<211> LENGTH: 122
<212> TYPE: PRT
<213> ORGANISM: Artificial sequence
<220> FEATURE:
<223> OTHER INFORMATION: sequence is synthesized

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Asp Thr Ser Tyr Asn Gln Lys Phe
    50                  55                  60
```

```
Lys Gly Arg Phe Thr Ile Ser Val Asp Lys Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser
        115                 120

<210> SEQ ID NO 138
<211> LENGTH: 213
<212> TYPE: PRT
<213> ORGANISM: Artificial sequence
<220> FEATURE:
<223> OTHER INFORMATION: sequence is synthesized

<400> SEQUENCE: 138

Asp Ile Gln Met Thr Gln Ser Pro Ser Ser Leu Ser Ala Ser Val Gly
 1               5                  10                  15

Asp Arg Val Thr Ile Thr Cys Arg Ala Ser Ser Ser Val Ser Tyr Met
             20                  25                  30

His Trp Tyr Gln Gln Lys Pro Gly Lys Ala Pro Lys Pro Leu Ile Tyr
         35                  40                  45

Ala Pro Ser Asn Leu Ala Ser Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Phe Asn Pro Pro Thr
                 85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 139
<211> LENGTH: 451
<212> TYPE: PRT
<213> ORGANISM: Artificial sequence
<220> FEATURE:
<223> OTHER INFORMATION: sequence is synthesized

<400> SEQUENCE: 139

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Ser Tyr
```

-continued

```
                20                  25                  30
        Asn Met His Trp Val Arg Gln Ala Pro Gly Lys Gly Leu Glu Trp Val
                     35                  40                  45
        Gly Ala Ile Tyr Pro Gly Asn Gly Asp Thr Ser Tyr Asn Gln Lys Phe
                 50                  55                  60
        Lys Gly Arg Phe Thr Ile Ser Val Asp Lys Ser Lys Asn Thr Leu Tyr
         65                  70                  75                  80
        Leu Gln Met Asn Ser Leu Arg Ala Glu Asp Thr Ala Val Tyr Tyr Cys
                         85                  90                  95
        Ala Arg Val Val Tyr Tyr Ser Asn Ser Tyr Trp Tyr Phe Asp Val Trp
                        100                 105                 110
        Gly Gln Gly Thr Leu Val Thr Val Ser Ser Ala Ser Thr Lys Gly Pro
                    115                 120                 125
        Ser Val Phe Pro Leu Ala Pro Ser Ser Lys Ser Thr Ser Gly Gly Thr
                    130                 135                 140
        Ala Ala Leu Gly Cys Leu Val Lys Asp Tyr Phe Pro Glu Pro Val Thr
        145                 150                 155                 160
        Val Ser Trp Asn Ser Gly Ala Leu Thr Ser Gly Val His Thr Phe Pro
                        165                 170                 175
        Ala Val Leu Gln Ser Ser Gly Leu Tyr Ser Leu Ser Ser Val Val Thr
                    180                 185                 190
        Val Pro Ser Ser Ser Leu Gly Thr Gln Thr Tyr Ile Cys Asn Val Asn
                    195                 200                 205
        His Lys Pro Ser Asn Thr Lys Val Asp Lys Lys Val Glu Pro Lys Ser
                210                 215                 220
        Cys Asp Lys Thr His Thr Cys Pro Pro Cys Pro Ala Pro Glu Leu Leu
        225                 230                 235                 240
        Gly Gly Pro Ser Val Phe Leu Phe Pro Pro Lys Pro Lys Asp Thr Leu
                        245                 250                 255
        Met Ile Ser Arg Thr Pro Glu Val Thr Cys Val Val Val Asp Val Ser
                    260                 265                 270
        His Glu Asp Pro Glu Val Lys Phe Asn Trp Tyr Val Asp Gly Val Glu
                    275                 280                 285
        Val His Asn Ala Lys Thr Lys Pro Arg Glu Glu Gln Tyr Asn Ser Thr
                290                 295                 300
        Tyr Arg Val Val Ser Val Leu Thr Val Leu His Gln Asp Trp Leu Asn
        305                 310                 315                 320
        Gly Lys Glu Tyr Lys Cys Lys Val Ser Asn Lys Ala Leu Pro Ala Pro
                        325                 330                 335
        Ile Glu Lys Thr Ile Ser Lys Ala Lys Gly Gln Pro Arg Glu Pro Gln
                    340                 345                 350
        Val Tyr Thr Leu Pro Pro Ser Arg Glu Glu Met Thr Lys Asn Gln Val
                    355                 360                 365
        Ser Leu Thr Cys Leu Val Lys Gly Phe Tyr Pro Ser Asp Ile Ala Val
                370                 375                 380
        Glu Trp Glu Ser Asn Gly Gln Pro Glu Asn Asn Tyr Lys Thr Thr Pro
        385                 390                 395                 400
        Pro Val Leu Asp Ser Asp Gly Ser Phe Phe Leu Tyr Ser Lys Leu Thr
                        405                 410                 415
        Val Asp Lys Ser Arg Trp Gln Gln Gly Asn Val Phe Ser Cys Ser Val
                    420                 425                 430
        Met His Glu Ala Leu His Asn His Tyr Thr Gln Lys Ser Leu Ser Leu
                435                 440                 445
```

```
Ser Pro Gly
    450

<210> SEQ ID NO 140
<211> LENGTH: 213
<212> TYPE: PRT
<213> ORGANISM: Artificial sequence
<220> FEATURE:
<223> OTHER INFORMATION: sequence is synthesized

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Leu
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ala Phe Asn Pro Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 141
<211> LENGTH: 451
<212> TYPE: PRT
<213> ORGANISM: Artificial sequence
<220> FEATURE:
<223> OTHER INFORMATION: sequence is synthesized

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Ala Thr Ser Tyr Asn Gln Lys Phe
    50                  55                  60

Lys Gly Arg Phe Thr Ile Ser Val Asp Lys Ser Lys Asn Thr Leu Tyr
```

```
            65                  70                  75                  80
Leu Gln Met Asn Ser Leu Arg Ala Glu Asp Thr Ala Val Tyr Tyr Cys
                    85                  90                  95

Ala Arg Val Val Tyr Ser Ala Ser Tyr Trp Tyr Phe Asp Val Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ala Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Ala Ala Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 142
<211> LENGTH: 451
<212> TYPE: PRT
<213> ORGANISM: Artificial sequence
```

<220> FEATURE:
<223> OTHER INFORMATION: sequence is synthesized

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Ala Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Ala Ser Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ala Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Ala Ala Leu Pro Ala Pro
                325                 330                 335

Ile Ala Ala Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

```
Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 143
<211> LENGTH: 451
<212> TYPE: PRT
<213> ORGANISM: Artificial sequence
<220> FEATURE:
<223> OTHER INFORMATION: sequence is synthesized

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Ala Thr Ser Tyr Asn Gln Lys Phe
    50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Tyr Arg Tyr Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ala Thr
    290                 295                 300
```

Tyr Arg Val Val Ser Val Leu Thr Val Leu His Gln Asp Trp Leu Asn
305                 310                 315                 320

Gly Lys Glu Tyr Lys Cys Lys Val Ser Asn Ala Ala Leu Pro Ala Pro
            325                 330                 335

Ile Ala Ala Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 144
<211> LENGTH: 107
<212> TYPE: PRT
<213> ORGANISM: Artificial sequence
<220> FEATURE:
<223> OTHER INFORMATION: sequence is synthesized

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Leu
            20                  25                  30

His Trp Tyr Gln Gln Lys Pro Gly Lys Ala Pro Lys Pro Leu Ile Tyr
        35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ala Phe Asn Pro Pro Thr
                85                  90                  95

Phe Gly Gln Gly Thr Lys Val Glu Ile Lys Arg
            100                 105

<210> SEQ ID NO 145
<211> LENGTH: 122
<212> TYPE: PRT
<213> ORGANISM: Artificial sequence
<220> FEATURE:
<223> OTHER INFORMATION: sequence is synthesized

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val

```
                      35                  40                  45
Gly Ala Ile Tyr Pro Gly Asn Gly Ala Thr Ser Tyr Asn Gln Lys Phe
        50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Ala Ser Tyr Trp Tyr Phe Asp Val Trp
            100                 105                 110

Gly Gln Gly Thr Leu Val Thr Val Ser Ser
        115                 120

<210> SEQ ID NO 146
<211> LENGTH: 122
<212> TYPE: PRT
<213> ORGANISM: Artificial sequence
<220> FEATURE:
<223> OTHER INFORMATION: sequence is synthesized

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
        35                  40                  45

Gly Ala Ile Tyr Pro Gly Asn Gly Ala Thr Ser Tyr Asn Gln Lys Phe
        50                  55                  60

Lys Gly Arg Phe Thr Ile Ser Val Asp Lys Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Tyr Arg Tyr Trp Tyr Phe Asp Val Trp
            100                 105                 110

Gly Gln Gly Thr Leu Val Thr Val Ser Ser
        115                 120
```